(12) United States Patent
Lee et al.

(10) Patent No.: US 11,268,102 B2
(45) Date of Patent: Mar. 8, 2022

(54) COMPOSITIONS AND METHODS FOR IDENTIFYING AND SELECTING BRACHYTIC LOCUS IN SOLANACEAE

(71) Applicant: University of Florida Research Foundation, Inc., Gainesville, FL (US)

(72) Inventors: Tong Geon Lee, Lithia, FL (US); Samuel Forrest Hutton, Tampa, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 105 days.

(21) Appl. No.: 16/412,901

(22) Filed: May 15, 2019

(65) Prior Publication Data

US 2020/0045901 A1 Feb. 13, 2020

Related U.S. Application Data

(60) Provisional application No. 62/672,092, filed on May 16, 2018.

(51) Int. Cl.
*C12N 15/82* (2006.01)
*A01H 1/04* (2006.01)

(52) U.S. Cl.
CPC ........... *C12N 15/8213* (2013.01); *A01H 1/04* (2013.01)

(58) Field of Classification Search
None
See application file for complete search history.

(56) References Cited

U.S. PATENT DOCUMENTS

| | | | |
|---|---|---|---|
| 5,210,015 A | 5/1993 | Gelfand et al. |
| 5,217,863 A | 6/1993 | Cotton et al. |
| 5,468,613 A | 11/1995 | Erlich et al. |
| 5,595,890 A | 1/1997 | Newton et al. |
| 5,616,464 A | 4/1997 | Albagli et al. |
| 5,762,876 A | 6/1998 | Lincoln et al. |
| 5,800,944 A | 9/1998 | Blonsky et al. |
| 5,876,930 A | 3/1999 | Livak et al. |
| 5,945,283 A | 8/1999 | Kwok et al. |
| 6,004,744 A | 12/1999 | Goelet et al. |
| 6,013,431 A | 1/2000 | Söderlund et al. |
| 6,030,787 A | 2/2000 | Livak et al. |
| 6,090,558 A | 7/2000 | Butler et al. |
| 6,503,710 B2 | 1/2003 | Gut et al. |
| 6,613,509 B1 | 9/2003 | Chen |
| 6,799,122 B2 | 9/2004 | Benson |
| 6,913,879 B1 | 7/2005 | Schena |
| 6,996,476 B2 | 2/2006 | Najarian |
| 7,238,476 B2 | 7/2007 | McKeown et al. |
| 7,250,252 B2 | 7/2007 | Katz et al. |
| 7,270,981 B2 | 9/2007 | Armes et al. |
| 7,282,355 B2 | 10/2007 | Shi |
| 7,297,485 B2 | 11/2007 | Bornarth et al. |
| 7,312,039 B2 | 12/2007 | Barany et al. |
| 2020/0140874 A1* | 5/2020 | Barten ................. C07K 14/415 |

OTHER PUBLICATIONS

Gebhardt. The historical role of species from the Solanaceae plant family in genetic research. Theor. Appl. Genet. Dec. 2016;129(12):2281-2294. Epub Oct. 15, 2016. (Year: 2016).*
Sjolander Phylogenomic inference of protein molecular function: advances and challenges. Bioinformatics. Jan. 22, 2004;20(2):170-9. (Year: 2004).*
Shattuck-Eidens et al. DNA sequence variation within maize and melon: observations from polymerase chain reaction amplification and direct sequencing. Genetics. Sep. 1990;126(1):207-17 (Year: 1990).*
NCBI Reference Sequence No. XP_006342791, "Predicted: flowering-promoting factor 1-like protein 3 [Solanum tuberosum]," Jan. 5, 2016. [Retrieved from the Internet Aug. 14, 2019: <URL: https://www.ncbi.nlm.nih.gov/protein/XP_006342791>].
NCBI Reference Sequence No. XP_015086900, "flowering-promoting factor 1-like protein 3 [Solanum pennellii]," Jan. 28, 2019. [Retrieved from the Internet Aug. 14, 2019: <URL: https://www.ncbi.nlm.nih.gov/protein/XP_015086900>].
NCBI Reference Sequence No. XP_016557588.1, "Predicted: flowering-promoting factor 1-like protein 3 [Capsicum annuum]," May 5, 2016 [Retrieved from the Internet Aug. 15, 2019: <URL: https://www.ncbi.nlm.nih.gov/protein/XP_016557588.1>].

* cited by examiner

*Primary Examiner* — Cynthia E Collins
(74) *Attorney, Agent, or Firm* — Alston & Bird LLP

(57) ABSTRACT

Molecular markers associated with Solanaceae brachytic locus, methods of their use, and compositions having one or more marker loci are provided. Methods comprising detecting at least one marker locus, detecting a haplotype, and/or detecting a marker profile are provided. Methods and compositions are described for breeding tomato plants containing quantitative trait loci that are associated with brachytic phenotype and monitoring introgression of brachytic locus. Methods and compositions are also described for modifying a brachytic locus using CRISPR/Cas.

19 Claims, 11 Drawing Sheets

Specification includes a Sequence Listing.

SEQUENCE ALIGNMENT

Solyc01g066970.2ch01_75101399  SEQ ID NO: 4
Solyc01g066950.1ch01_75049083  SEQ ID NO: 3
Solyc01g066980.2ch01_75108781  SEQ ID NO: 2
Solyc01g066980_brachytic       SEQ ID NO: 48

```
Solyc01g066970.2ch01_75101399  TGCCTCACAAATTAAAATTTTTCAAATATCATTAACCAGATTTAATAAAG
Solyc01g066950.1ch01_75049083  -----TATATATATATATTCTTGACATCTTACTTTATTTTTTTAAAACAG
Solyc01g066980.2ch01_75108781  -----GATATAAGGAATTCTTGTTTTTTTTTATTTTTTTATTTTTGAAAA-
Solyc01g066980_brachytic       -----GATATAAGGAATTCTTGTTTTTTTTTATTTTTTTATTTTTGAAAA-
                                     *   *    *  *  *       **  **    * ***  *  *

Solyc01g066970.2ch01_75101399  C--AGAATTTGTAATTGAAAAGTAGCGCTAAATTAATTACGTGGAAAGCT
Solyc01g066950.1ch01_75049083  TGAAGAATTCGAATTTGAGGTAAAGCCTTTGAATTTATAGTCAAAGACTT
Solyc01g066980.2ch01_75108781  ---AGGATGAGCCTTCTTGGGAT-GCGTGCACTTTCGAAGTCATTAAAGT
Solyc01g066980_brachytic       ---AGGATGAGCCTTCTTGGGAT-GCGTGCACTTTCGAAGTCATTAAAGT
                                  ** **   *    *       **     *       *   *   *

Solyc01g066970.2ch01_75101399  AAAGTTAAAATGTAACCAAAAAAAAAGTCATTCT-TTTATATAAAAAAAA
Solyc01g066950.1ch01_75049083  CTTGATGAAATAAATGGGAAAATACCATTTTGTC-TTTATTCAAAATAAG
Solyc01g066980.2ch01_75108781  CGAA-TAAGAAGAAAGAAATATCTTCGTCATTTTGTTTCTTCTTAAAACA
Solyc01g066980_brachytic       CGAA-TAAGAAGAAAGAAATATCTTCGTCATTTTGTTTCTTCTTAAAACA
                                *     *     *      *      *    * *** *   ** *

Solyc01g066970.2ch01_75101399  A--AACTAAAAAGGAAAGAAGATTATTCTTTTTTAAACGGGGAAAAAAAA
Solyc01g066950.1ch01_75049083  ACCAAAAAAAAAAGAGAAAAGAAAAGATATTTCCATA----AAAAAAAAT
Solyc01g066980.2ch01_75108781  AGCTACGAAAAAGTTTTTGAGGTTATAAGTTTCAGAG-----TATTAATT
Solyc01g066980_brachytic       AGCTACGAAAAAGTTTTTGAGGTTATAAGTTTCAGAG-----TATTAATT
                                *   *****     **    ***      *           *  **

Solyc01g066970.2ch01_75101399  AACTAAAAAGGAAAGAAGATTATTCTTTTTTTAAACGGGGAAGTATATATA
Solyc01g066950.1ch01_75049083  ATATCAATCACATATCCACCTATCATCGTTGGCTTAATGATAAAAATATA
Solyc01g066980.2ch01_75108781  TTTATAGTATTAGAGTAATTCAACATTTATAAAAGGTCAATACTAAATTA
Solyc01g066980_brachytic       TTTATAGTATTAGAGTAATTCAACATTTATAAAAGGTCAATACTAAATTA
                                *    *  **    * *    *         *           * **

Solyc01g066970.2ch01_75101399  TATATATATATATATATATAT--ATATATATATATATATATATATATATG
Solyc01g066950.1ch01_75049083  ATCGGTTTGACTTGATACAAA----ATTTAAGTAAATAAAGA-AGACTTT
Solyc01g066980.2ch01_75108781  GATATCTATAATTACATTTTGATTCATTGACTTAATGATATAAATATGTG
Solyc01g066980_brachytic       GATATCTATAATTACATTTTGATTCATTGACTTAATGATATAAA------
                                **   *  **    *   **   *   **   * * *   *

Solyc01g066970.2ch01_75101399  CGCGTGTGTGAGAGACTCAAAATTGAAG-TATTTGATAGTAAGAATTTAT
Solyc01g066950.1ch01_75049083  TAAATATATATGACTAAAAATTTAAG-TATTTGATAGTACAAATTTAT
Solyc01g066980.2ch01_75108781  TACATAGATTTTAAGCGCAAAAGGAAAAATATTTTGTGGAATAAGCACTC
Solyc01g066980_brachytic       --------------------------------------------------
                                  *   *    *  ****   **   ***** *   *   *

Solyc01g066970.2ch01_75101399  TTCAGTATATAGATAAAATTTTC-AAGCCAAACCAAGTTTTTTTATTGCC
Solyc01g066950.1ch01_75049083  TTAAGTATATAGATAAAAGTTTCGAAGCGAAACCAAGTTTT---ATTGCC
Solyc01g066980.2ch01_75108781  TTATATATATATATATCATATAATAAAACACATTCACTTGT---AATAAT
Solyc01g066980_brachytic       --------------------------------------------------
                                **  ****** ***   *   **    *  *   * **    *  *
```

FIG. 3

```
Solyc01g066970.2ch01_75101399  ATAAAAC-TTCACTCTTACACACAATTAC---AAGTAATAA--TTAGCTT
Solyc01g066950.1ch01_75049083  ATAAA-C-TTCACTCTTACACACCATTACAACAAGTAATAA--TTAGCTT
Solyc01g066980.2ch01_75108781  ATACAACATTTCCCCTCTTACAACTTTCC---AAATTACAACCTTAGCAA
Solyc01g066980_brachytic       --------------------------------------------------
                               *** * * ** *  * **    ***    ** *   ** * * ** *****

Solyc01g066970.2ch01_75101399  CCTCACCCAAAAGAAACTAAAACACCCCCCTTAAACCTAAATTACACAAA
Solyc01g066950.1ch01_75049083  CCTCACCCAAAAGAAACTAAAACACCCCCCTTTGACCTAAATTACACAAA
Solyc01g066980.2ch01_75108781  CATTGTG-AAACAAATCACAAATTAAACGATAGAAACTTAATTACA----
Solyc01g066980_brachytic       --------------------------------------------------
                               *  *   *** ** *  *** *       *   *  ** *******

Solyc01g066970.2ch01_75101399  CCAAACATTAAGTTAAAACAAGAAACAACCTAATTTAAATCAAACAACAT
Solyc01g066950.1ch01_75049083  CCAAACCTTAAGTTAAAAGAAGAAACAACCTAATTTAAATTAAACAACAT
Solyc01g066980.2ch01_75108781  --ACACACTTGACCAAAA--AAAAGCAAAAAAAAGAAAAAAAAAACACATT
Solyc01g066980_brachytic       --------------------------------------------------
                                 * **   *    ****  * ** ***    **   ***  *****  *

Solyc01g066970.2ch01_75101399  TAATTAATTTGAGAAAAATATCTCAAATCAACTAATTATTAATTAGTAGT
Solyc01g066950.1ch01_75049083  TAATTAATTTGAGAAAAAT--CTCAAATCAACTAATGATTA-TTAGTAAT
Solyc01g066980.2ch01_75108781  CAAATGATC------AACTCCTTCCCTTTTTTCCCCCATATTTTGT---
Solyc01g066980_brachytic       --------------------------------------------------
                                ** * **       **        **    **    *     ** ** **

Solyc01g066970.2ch01_75101399  ACTACATATCCCTAACTGTAAACTCATTACGATTCTTAACAACAATATCA
Solyc01g066950.1ch01_75049083  ACTACATATCCCTAACAGCAAACTCATTACGATTCTTAACAACAATATCA
Solyc01g066980.2ch01_75108781  -TTACATATCTCTAACCTCAAATTCATTGCGATTCTTGACGACGATATCG
Solyc01g066980_brachytic       --------------------------------------------------
                                ******** *****   ***  ***** ***** ** ** ** *****

Solyc01g066970.2ch01_75101399  TACATGTGCATGGACTTGAGGTTGTTGAAGTCCTTTGGTAGAGAAATAAG
Solyc01g066950.1ch01_75049083  TACATGTGCATGGACCTGAGGTTGTTGAAGTCGTTTGGTAGAGAAATAAG
Solyc01g066980.2ch01_75108781  AACATATGCATGGATTTGAACCTGTTGAAATCCTTTGGTAGAGAAATAAG
Solyc01g066980_brachytic       --------------------------------------------------
                                **** ********    ***    ******* ** ******************

Solyc01g066970.2ch01_75101399  ATGAACAGTTGATCTTTTATGGAATTGAAGAAGGTCAGGGTCATCATAGT
Solyc01g066950.1ch01_75049083  ATGAACAGTTGATCTTTTATGGTACTGAAGAAGGTCAGGGTCATCATAGT
Solyc01g066980.2ch01_75108781  ATGAACGGTTGATCTTTTGTGGTATTGAAGAAGTTCAGGTTCATCATAGT
Solyc01g066980_brachytic       --------------------------------------------------
                               ****** *********** ***  * ******* ***** **********

Solyc01g066970.2ch01_75101399  ACCTCTCCCATCCAAGAGAGTACAGTTTCCTTTCAAGTACTGCATATGAT
Solyc01g066950.1ch01_75049083  ACCTCTCCCATCCAAGAGAGTACAGTTTCCTTTCAAGTACTGCATATGAT
Solyc01g066980.2ch01_75108781  ACCTCTCCCATCCAAGAGAGTACAGTTTCCTTTCAAGTACTGCATATGAT
Solyc01g066980_brachytic       --------------------------------------------------
                               **************************************************

Solyc01g066970.2ch01_75101399  GTTATTACTTCATTACTAGAAAGGTGCACAAGCACTTTACGACGACCCGT
Solyc01g066950.1ch01_75049083  GTTATTACTTCATTACTAGAAAGGTGCACAAGCACTTTACGACGACCCGT
Solyc01g066980.2ch01_75108781  GTGATGACTTCATTACTAGGAAGATGTACAAGAACTTTTCGGAGTCCGTT
Solyc01g066980_brachytic       --------------------------------------------------
                               ** ** ************* *** ** ***** *****  *  *  ** *

Solyc01g066970.2ch01_75101399  CGCACCGTGGAAGTCACCGGGGTTCTCAACTAGCCTCACTACTCCATTCT
Solyc01g066950.1ch01_75049083  CGCACCGTGAAAGTCACCGAGGTTCTCAACTAGCCTCACTACTCCATTCT
Solyc01g066980.2ch01_75108781  CGCCCCGTGGCAAT---CGGAGTTCTCCACTAGACGGACAACACCATTCT
Solyc01g066980_brachytic       --------------------------------------------------
                               *** *****    *   ** ****** * ****   ** ** *******
```

FIG. 3 cont.

```
Solyc01g066970.2ch01_75101399   TGAATACCCAAACACCAGACATGTTT-CAAAAAATATATGAATATGAAAA
Solyc01g066950.1ch01_75049083   TGATTTTCCAAACACCAGACATGTTT-CAAAAAATAT--GAATATGAAAC
Solyc01g066980.2ch01_75108781   TGAATACCCAAACTCCAGACATGATTGTTGAAGATGT--TGTTATGTTTT
Solyc01g066980_brachytic        -------------------------------GATGT--TGTTATGTTTT
                                 *** *  ******  ********* **     **  **  *    ****

Solyc01g066970.2ch01_75101399   TAGTAAGTGAGTATTGTGTGTGAGT-TTGAACATAAGTGTGAGTGGGTTT
Solyc01g066950.1ch01_75049083   TAGTGAGTGAGTATTGTGTGTGAGT-TTGAAGATAAGTGTGAAGGGGTTT
Solyc01g066980.2ch01_75108781   TTGTAGAGGAAAGGTGAATGAGAATGTTTTTTGTATGTGTTTGTAGTTTA
Solyc01g066980_brachytic        TTGTAGAGGAAAGGTGAATGAGAATGTTTTTTGTATGTGTTTGTAGTTTA
                                * **    **      **    **   **  **    **  ****    *  **

Solyc01g066970.2ch01_75101399   TTATAGG--GGTTTCTATGTAGTGTGTAATAAAAAAATACATAAGGTGGC
Solyc01g066950.1ch01_75049083   TTATACG--GGTTTCTATGTAAT--------AAAAAATACATTAGGTGGC
Solyc01g066980.2ch01_75108781   TGATGAGATGGTTTGGATGTAAGAGGGTGT-GAGGGGTTTATATAGAGGG
Solyc01g066980_brachytic        TGATGAGATGGTTTGGATGTAAGAGGGTGT-GAGGGGTTTATATAGAGGG
                                * **   *   *****  *****         *      *  **  * **

Solyc01g066970.2ch01_75101399   AAAAAGTAATCTTTTTTCTTATTTAATAAAATTGATAATAGGTAGGATTT
Solyc01g066950.1ch01_75049083   AAAAAGTA-TTTTCTTTCTTATTTAATAAAATTGATGAT------GATT-
Solyc01g066980.2ch01_75108781   TTTTGGATGCTTACAATTATATTGTGTGAGTTTGATAGA------GGTCT
Solyc01g066980_brachytic        TTTTGGATGCTTACAATTATATTGTGTGAGTTTGATAGA------GGTCT
                                        *        *    ****   *  *  *****         *  *

Solyc01g066970.2ch01_75101399   TGGAATGTGGCTGCTTATAGGATTTAGAAATATACTAACTTATCGTACGT
Solyc01g066950.1ch01_75049083   ---AATAGG--------TAGGATTTAGAATTATACTAACTTATCGTACGC
Solyc01g066980.2ch01_75108781   TAAAGTG------------GATAGTGGGGTAGTCTCCCCCGTTTCTGGC
Solyc01g066980_brachytic        TAAAGTG------------GATAGTGGGGTAGTCTCCCCCGTTTCTGGC
                                  * *                ***    *  **  **    *    *     *

Solyc01g066970.2ch01_75101399   TTATTAAGATTAAAGAAAAAGAAAGGGAGAATATTTAAATGGCCACAAGA
Solyc01g066950.1ch01_75049083   TCAT-AAGATTAAAGAAAAAGAAAGGGAGAATATTTATATGGCCACAAGA
Solyc01g066980.2ch01_75108781   ATCTTTAGAATTTCGAGATTCAAACG-AGTATTTTTTTATCACGATTAAT
Solyc01g066980_brachytic        ATCTTTAGAATTTCGAGATTCAAACG-AGTATTTTTTTATCACGATTAAT
                                  *  ****  *     **  *      ***  *  **  **  ***   **     *  *    *

Solyc01g066970.2ch01_75101399   TGCCCTAATTTGCCCTACTGAAATTAGAATCTTCTCCTAAACAATCACTA
Solyc01g066950.1ch01_75049083   TACCCTAATTTACCTGTCACGACCCAAAACGGACCGCGAGTGGCACCCAC
Solyc01g066980.2ch01_75108781   T------ATATATTTTGTATTATTTTAAATAATCTGTTACAGTAATTTAT
Solyc01g066980_brachytic        T------ATATATTTTGTATTATTTTAAATAATCTGTTACAGTAATTTAT
                                *         **  *        *       **       *   *       *

Solyc01g066970.2ch01_75101399   ATTAATGATCTTATG-CTCATAAG---ATGAACCTAATTCTTTTGGTT-A
Solyc01g066950.1ch01_75049083   ATTTATCTTCCTATG-TGAGCGAACCAACCAATCTAAACCCAACATTTCA
Solyc01g066980.2ch01_75108781   AGCAGTTTTTACATAATTTCTATATATACTAATTTTATCTCAAAAATTTG
Solyc01g066980_brachytic        AGCAGTTTTTACATAATTTCTATATATACTAATTTTATCTCAAAAATTTG
                                 *      *       ***             *   **  *   *    **

Solyc01g066970.2ch01_75101399   ---ATGGGTT--CCAAGCATAATTC------TTTAATTTTTTTAGTGCTA
Solyc01g066950.1ch01_75049083   ---ATATAATGACGGAATATAATGCGGAAGACTTAACCTCATTAATG--A
Solyc01g066980.2ch01_75108781   TGTGTATGAATACACAAGAAAATCAAAAGTTTAATTTCTGAAAAAC-A
Solyc01g066980_brachytic        TGTGTATGAATACACAAGAAAATCAAAAGTTTAATTTCTGAAAAAC-A
                                       *            *  **  *       ****  *      *

Solyc01g066970.2ch01_75101399   AGAACAATCTTCTATTCTTATATCCATTGCTTGATC---AGCCCT-TCAC
Solyc01g066950.1ch01_75049083   AAATCAATTAAATAA-CTTCTAAAAACTCAACAACT---ATTATTATCCC
Solyc01g066980.2ch01_75108781   AATTATATTGCATAAATTGAAATAAAGAAAATAATTTTAAGGTTAATTAT
Solyc01g066980_brachytic        AATTATATTGCATAAATTGAAATAAAGAAAATAATTTTAAGGTTAATTAT
                                 *    **   **    *   *    *     *    *      *    *
```

FIG. 3 cont.

```
Solyc01g066970.2ch01_75101399  AAAAAGGAAGAATTAAATAAATTAAAAGATATT---TCGGGGAAGATTAA
Solyc01g066950.1ch01_75049083  CAAAATCTGGAAGTCATCATCATAAGA-ACATC---TATCCTCAAATTAC
Solyc01g066980.2ch01_75108781  TACCACTTAAATATGTTGATAGTGAAGAAAATTCTTTACGTTTAGAATGT
Solyc01g066980_brachytic       TACCACTTAAATATGTTGATAGTGAAGAAAATTCTTTACGTTTAGAATGT
                                    *    *       *  * *   * **    *    *  *   *

Solyc01g066970.2ch01_75101399  TTTGTCCCATCTCATGTTGATGA-TGTTTCTTTTAATCCTTAATTAATGT
Solyc01g066950.1ch01_75049083  TAAAGCTAAGAGTATCTAGAAAGCTAGAATAAATAAAAGCTAGTTCATGC
Solyc01g066980.2ch01_75108781  GTGTATCAAAATTGTGTAGCAAGTGAAAAGTTTTGAGGGGTATTTTACAA
Solyc01g066980_brachytic       GTGTATCAAAATTGTGTAGCAAGTGAAAAGTTTTGAGGGGTATTTTACAA
                                       *   * *               * *    ** **  *

Solyc01g066970.2ch01_75101399  CT-AATAACAATTTTTT----TTTAAAAAAAAAAAATTACTCCAAATCAA
Solyc01g066950.1ch01_75049083  CGGAACTTCAAGGCATCGAGACATGAAGAAGAAGATCCAGTCCAAGCTAG
Solyc01g066980.2ch01_75108781  CTAATGTACGAGAAGATT--GTAGGAGAAACATATTCTTGTACCCTTAAA
Solyc01g066980_brachytic       CTAATGTACGAGAAGATT--GTAGGAGAAACATATTCTTGTACCCTTAAA
                                *  *   *                *  **  *        *  *    *

Solyc01g066970.2ch01_75101399  TGAGA--AATTTGTGTTATGATACGTGATATTCCCACCCATT-TCCTATT
Solyc01g066950.1ch01_75049083  AAGCGTTAGCTCACCCTGAAATCCGGTGTAATGAAGATCGGC-TAGAGTT
Solyc01g066980.2ch01_75108781  GAATATAATATACCCTTGTTACTATTATCAAAGTGGACGAATATGACATT
Solyc01g066980_brachytic       GAATATAATATACCCTTGTTACTATTATCAAAGTGGACGAATATGACATT
                                      *        *             *             *   **

Solyc01g066970.2ch01_75101399  -TAACTAGGT-CAATAAAAACGTATGGTGAGAAACAAATTCTCACTAAAA
Solyc01g066950.1ch01_75049083  GCGGTTGAGT-TAAAGACGACGGCACGTTTGCTGCACTCCACAAATAACA
Solyc01g066980.2ch01_75108781  TTGTTTGCATATATAAGTGATGAAAATTTCCCAACTTTATAAGGACGTTG
Solyc01g066980_brachytic       TTGTTTGCATATATAAGTGATGAAAATTTCCCAACTTTATAAGGACGTTG
                                    *      *   *     *  *            *

Solyc01g066970.2ch01_75101399  TACCAAGAGTTTTTTTTTTTAATTTTGTTGTGTAATTTAAACATTAGTG-
Solyc01g066950.1ch01_75049083  AGGAAAGAAACATACAAGTAGGGGTCAGTACAAAACACGATCATCGGCCA
Solyc01g066980.2ch01_75108781  TTCATGAAAGCAAAAAATTAAA----ATTATAAAATTTTACCATCAAAGG
Solyc01g066980_brachytic       TTCATGAAAGCAAAAAATTAAA----ATTATAAAATTTTACCATCAAAGG
                                     *         *         *    *  **  *  ***

Solyc01g066970.2ch01_75101399  --TGAGTATAGC---CACTGGACATTTTTCAATAGGAAAATTTCAATGGG
Solyc01g066950.1ch01_75049083  ACTCAAAATAGAAAGCAATATATATCAAGTAATAATATGAAATCAACTAC
Solyc01g066980.2ch01_75108781  AAATAAGATTAT---TGGAGTAAAAAGTGTATATATATATATATATATTG
Solyc01g066980_brachytic       AAATAAGATTAT---TGGAGTAAAAAGTGTATATATATATATATATATTG
                                   *  **          *      *     *       *       *

Solyc01g066970.2ch01_75101399  AT-----AGTGTCT-GTTCCAATTTGTTTATCTAGTTTTAGTT--TGACA
Solyc01g066950.1ch01_75049083  ATTACTCAACATGTAGCAACAACAAGTACTATGATCGTTAATAAGTACCG
Solyc01g066980.2ch01_75108781  ATTATTGATCAT---GCAAGTAGAGAATTGACACGTGTTTGAGAACATT-
Solyc01g066980_brachytic       ATTATTGATCAT---GCAAGTAGAGAATTGACACGTGTTTGAGAACATT-
                               **     *    *     *    *       *              **
```

FIG. 3 cont.

SEQUENCE LISTING

<160> NUMBER OF SEQ ID NOS: 67

<210> SEQ ID NO 1
<211> LENGTH: 825
<212> TYPE: DNA
<213> ORGANISM: Solanum lycopersicum

<400> SEQUENCE: 1
gatgttgtta tgttttttgt agaggaaagg tgaatgagaa tgttttttgt atgtgtttgt    60
agtttatgat gagatggttt ggatgtaaga gggtgtgagg ggtttatata gagggttttg   120
gatgcttaca attatattgt gtgagtttga tagaggtctt aaagtggata gtggggtagt   180
ctcccccgtt tctggcatct ttagaatttc gagattcaaa cgagtatttt tttatcacga   240
ttaattatat attttgtatt attttaaata atctgttaca gtaatttata gcagttttta   300
cataatttct atatatacta attttatctc aaaaatttgt gtgtatgaat acacaagaaa   360
aatcaaaaag tttaatttct gaaaaacaaa ttatattgca taaattgaaa taagaaaat   420 aattttaagg ttaattatta ccacttaaat atgttgatag tgaagaaaat tctttacgtt   480
tagaatgtgt gtatcaaaat tgtgtagcaa gtgaaaagtt ttgaggggta ttttacaact   540
aatgtacgag aagattgtag gagaaacata ttccttgtacc cttaaagaat ataatatacc   600
cttgttacta ttatcaaagt ggacgaatat gacattttgt ttgcatatat aagtgatgaa   660
aatttcccaa ctttataagg acgttgttca tgaaagcaaa aaattaaaat tataaaattt   720
taccatcaaa ggaaataaga ttattggagt aaaaagtgta tatatatata tatatattga   780
ttattgatca tgcaagtaga gaattgacac gtgtttgaga acatt            825

<210> SEQ ID NO 2
<211> LENGTH: 1712
<212> TYPE: DNA
<213> ORGANISM: Solanum lycopersicum

<400> SEQUENCE: 2
gatataagga attcttgttt tttttatttt tttattttg aaaaaggatg agccttcttg    60
ggatgcgtgc actttcgaag tcattaaagt cgaataagaa gaaagaaata tcttcgtcat   120
tttgtttctt cttaaaacaa gctacgaaaa agttttgag gttataagtt tcagagtatt   180
aatttttata gtattagagt aattcaacat ttataaaagg tcaatactaa attagatatc   240

```
tataattaca ttttgattca ttgacttaat gatataaata tgtgtacata gattttaagc      300
gcaaaaggaa aaatattttg tggaataagc actcttatat atatatatat catataataa      360
aacacattca cttgtaataa tatacaacat ttcccctctt acaactttcc aaattacaac      420
cttagcaaca ttgtgaaaca aatcacaaat taaacgatag aaacttaatt acaacacact      480
tgaccaaaaa aaagcaaaaa aagaaaaaa aaacacattc aaatgatcaa ctccttccct       540
tttttccccc atattttgtt tacatatctc taacctcaaa ttcattgcga ttcttgacga      600
cgatatcgaa catatgcatg gatttgaacc tgttgaaatc ctttggtaga gaaataagat      660
gaacggttga tcttttgtgg tattgaagaa gttcaggttc atcatagtac ctctcccatc      720
caagagagta cagtttcctt tcaagtactg catatgatgt gatgacttca ttactaggaa      780
gatgtacaag aacttttcgg agtccgttcg ccccgtggca atcggagttc tccactagac      840
ggacaacacc attcttgaat acccaaactc cagacatgat tgttgaagat gttgttatgt      900
tttttgtaga ggaaaggtga atgagaatgt ttttgtatg tgtttgtagt ttatgatgag        960
atggtttgga tgtaagaggg tgtgaggggt ttatatagag ggttttggat gcttacaatt     1020
atattgtgtg agtttgatag aggtcttaaa gtggatagtg gggtagtctc ccccgttttct    1080 ggcatcttta gaatttcgag attcaaacga gtatttttt atcacgatta attatatatt      1140
ttgtattatt ttaaataatc tgttacagta atttatagca gttttacat aatttctata      1200 tatactaatt ttatctcaaa aatttgtgtg tatgaataca caagaaaaat caaaaagttt     1260
aatttctgaa aaacaaatta tattgcataa attgaaataa agaaaataat tttaaggtta     1320
attattacca cttaaatatg ttgatagtga agaaaattct ttacgtttag aatgtgtgta     1380
tcaaaattgt gtagcaagtg aaaagttttg agggggtattt tacaactaat gtacgagaag    1440
attgtaggag aaacatattc ttgtaccctt aaagaatata atatacccctt gttactatta   1500 tcaaagtgga cgaatatgac attttgtttg catatataag tgatgaaaat ttcccaactt    1560
tataaggacg ttgttcatga aagcaaaaaa ttaaaattat aaaattttac catcaaagga    1620
aataagatta ttggagtaaa aagtgtatat atatatatat atattgatta ttgatcatgc    1680
aagtagagaa ttgacacgtg tttgagaaca tt                                    1712
```

<210> SEQ ID NO 3
<211> LENGTH: 1725
<212> TYPE: DNA
<213> ORGANISM: Solanum lycopersicum

<400> SEQUENCE: 3

```
tatatatata tattcttgac atcttacttt attttttaa aacagtgaag aattcgaatt       60
tgaggtaaag cctttgaatt tatagtcaaa gacttcttga tgaaataaat gggaaaatac     120
cattttgtct ttattcaaaa taagaccaaa aaaaaagag aaaagaaaag atatttccat     180
aaaaaaaaat atatcaatca catatccacc tatcatcgtt ggcttaatga taaaaatata     240
atctggtttg acttgataca aaatttaagt aaataaagaa gacttttaaa tatatatatg     300
actaaaaatt taagtatttg atagtacaaa tttatttaag tatatagata aaagtttcga     360
agcgaaacca agttttattg ccataaactt cactcttaca caccattaca acaagtaata     420
attagcttcc tcacccaaaa gaaactaaaa cacccccctt tgacctaaat tacacaaacc     480
aaaccttaag ttaaagaag aaacaaccta atttaaatta aacaacatta attaatttga      540
gaaaaatctc aaatcaacta atgattatta gtaatactac atatccctaa cagcaaactc    600
```

```
attacgattc ttaacaacaa tatcatacat gtgcatggac ctgaggttgt tgaagtcgtt       660
tggtagagaa ataagatgaa cagttgatct tttatggtac tgaagaaggt cagggtcatc       720
atagtacctc tcccatccaa gagagtacag tttcctttca agtactgcat atgatgttat       780
tacttcatta ctagaaaggt gcacaagcac tttacgacga cccgtcgcac cgtgaaagtc       840
accgaggttc tcaactagcc tcactactcc attcttgatt ttccaaacac cagacatgtt       900
tcaaaaaata tgaatatgaa actagtgagt gagtattgtg tgtgagtttg aagataagtg       960
tgaaggggtt tttatacggg tttctatgta ataaaaaata cattaggtgg caaaaagtat      1020
tttctttctt atttaataaa attgatgatg attaataggt aggatttaga attatactaa      1080
cttatcgtac gctcataaga ttaaagaaaa agaaagggag aatatttata tggccacaag      1140
ataccctaat ttacctgtca cgacccaaaa cggaccgcga gtggcaccca catttatctt      1200
cctatgtgag cgaaccaacc aatctaaacc caacatttca atataatgac ggaatataat      1260
gcggaagact taacctcatt aatgaaaatc aattaaataa cttctaaaaa ctcaacaact      1320
attattatcc ccaaaatctg gaagtcatca tcataagaac atctatcctc aaattactaa      1380
agctaagagt atctagaaag ctagaataaa taaaagctag ttcatgccgg aacttcaagg      1440
catcgagaca tgaagaagaa gatccagtcc aagctagaag cgttagctca ccctgaaatc      1500
cggtgtaatg aagatcggct agagttgcgg ttgagttaaa gacgacggca cgtttgctgc      1560
actccacaaa taacaaggaa agaaacatac aagtaggggt cagtacaaaa cacgatcatc      1620
ggccaactca aaatagaaag caatatatat caagtaataa tatgaaatca actacattac      1680
tcaacatgta gcaacaacaa gtactatgat cgttaataag taccg                     1725

<210> SEQ ID NO 4
<211> LENGTH: 1733
<212> TYPE: DNA
<213> ORGANISM: Solanum lycopersicum

<400> SEQUENCE: 4
tgcctcacaa attaaaattt ttcaaatatc attaaccaga tttaataaag cagaatttgt        60
aattgaaaag tagcgctaaa ttaattacgt ggaaagctaa agttaaaatg taaccaaaaa       120
aaaagtcatt cttttatata aaaaaaaaaa ctaaaaagga agaagattta ttctttttta       180
aacggggaaa aaaaaaacta aaaaggaaag aagattattc ttttttaaac ggggaagtat       240
atatatatat atatatatat atatatatat atatatatat atatatatat atgcgcgtgt       300
gtgagagact caaaattgaa gtatttgata gtaagaattt atttcagtat atagataaaa       360
ttttcaagcc aaaccaagtt ttttttattgc cataaaactt cactcttaca cacaattaca       420
agtaataatt agcttcctca cccaaaagaa actaaaacac cccccttaaa cctaaattac       480
acaaaccaaa cattaagtta aaacaagaaa caacctaatt taaatcaaac aacattaatt       540
aatttgagaa aaatatctca aatcaactaa ttattaatta gtagtactac atatccctaa       600
ctgtaaactc attacgattc ttaacaacaa tatcatacat gtgcatggac ttgaggttgt       660
tgaagtcctt tggtagagaa ataagatgaa cagttgatct tttatggaat tgaagaaggt       720
cagggtcatc atagtacctc tcccatccaa gagagtacag tttcctttca agtactgcat       780
atgatgttat tacttcatta ctagaaaggt gcacaagcac tttacgacga cccgtcgcac       840
cgtggaagtc accgggggttc tcaactagcc tcactactcc attcttgaat acccaaacac       900
cagacatgtt tcaaaaaata tatgaatatg aaaatagtaa gtgagtattg tgtgtgagtt       960
tgaacataag tgtgagtggg ttttttatagg ggtttctatg tagtgtgtaa taaaaaaata      1020
```

```
cataaggtgg caaaaagtaa tctttttct tatttaataa aattgataat aggtaggatt    1080
ttggaatgtg gctgcttata ggatttagaa atatactaac ttatcgtacg tttattaaga    1140
ttaaagaaaa agaaagggag aatatttaaa tggccacaag atgccctaat ttgccctact    1200
gaaattagaa tcttctccta aacaatcact aattaatgat cttatgctca taagatgaac    1260
ctaattcttt tggttaatgg gttccaagca taattcttta attttttag tgctaagaac     1320 aatcttctat tcttatatcc attgcttgat cagcccttca caaaaggaa gaattaaata     1380 aattaaaaga tatttcgggg aagattaatt tgtcccatct catgttgatg atgtttcttt    1440
taatccttaa ttaatgtcta ataacaattt ttttttaaaa aaaaaaaatt actccaaatc    1500
aatgagaaat ttgtgttatg atacgtgata ttcccaccca tttcctattt aactaggtca    1560
ataaaaacgt atggtgagaa acaaattctc actaaaatac caagagtttt ttttttttaat   1620 tttgttgtgt aatttaaaca ttagtgtgag tatagccact ggacattttt caataggaaa    1680
atttcaatgg gatagtgtct gttccaattt gtttatctag ttttagtttg aca            1733
```

<210> SEQ ID NO 5
<211> LENGTH: 76
<212> TYPE: DNA
<213> ORGANISM: Solanum lycopersicum

<400> SEQUENCE: 5

```
catctcatca taaactacaa acacatacaa aaaacattct cattcacctt tcctctacaa     60
aaaacataac aacatc                                                     76
```

<210> SEQ ID NO 6
<211> LENGTH: 632
<212> TYPE: DNA
<213> ORGANISM: Solanum lycopersicum

<400> SEQUENCE: 6

```
catctcatca taaactacaa acacatacaa aaaacattct cattcacctt tcctctacaa     60
aaaacataac aacatcttca acaatcatgt ctggagtttg ggtattcaag aatggtgttg     120
tccgtctagt ggagaactcc gattgccacg gggcgaacgg actccgaaaa gttcttgtac    180
atcttcctag taatgaagtc atcacatcat atgcagtact tgaaaggaaa ctgtactctc    240
ttggatggga gaggtactat gatgaacctg aacttcttca ataccacaaa agatcaaccg    300
ttcatcttat ttctctacca aaggatttca acaggttcaa atccatgcat atgttcgata    360
tcgtcgtcaa gaatcgcaat gaatttgagg ttagagatat gtaaacaaaa tatgggggaa    420
aaaagggaag gagttgatca tttgaatgtg ttttttttc tttttttgc ttttttttgg      480 tcaagtgtgt tgtaattaag tttctatcgt ttaatttgtg atttgtttca caatgttgct    540
aaggttgtaa tttggaaagt tgtaagaggg gaaatgttgt atattattac aagtgaatgt    600
gttttattat atgatatata tatatataag ag                                  632
```

<210> SEQ ID NO 7
<211> LENGTH: 321
<212> TYPE: DNA
<213> ORGANISM: Solanum lycopersicum

<400> SEQUENCE: 7

```
atgtctggtg tttggaaaat caagaatgga gtagtgaggc tagttgagaa cctcggtgac     60
tttcacggtg cgacgggtcg tcgtaaagtg cttgtgcacc tttctagtaa tgaagtaata    120
```

```
acatcatatg cagtacttga aaggaaactg tactctcttg gatgggagag gtactatgat    180
gaccctgacc ttcttcagta ccataaaaga tcaactgttc atcttatttc tctaccaaac    240
gacttcaaca acctcaggtc catgcacatg tatgatattg ttgttaagaa tcgtaatgag    300
tttgctgtta gggatatgta g                                              321
```

<210> SEQ ID NO 8
<211> LENGTH: 606
<212> TYPE: DNA
<213> ORGANISM: Solanum lycopersicum

<400> SEQUENCE: 8

```
ctcacacaca atactcactt actattttca tattcatata ttttttgaaa catgtctggt     60
gtttgggtat tcaagaatgg agtagtgagg ctagttgaga accccggtga cttccacggt    120
gcgacgggtc gtcgtaaagt gcttgtgcac cttttctagta atgaagtaat aacatcatat    180
gcagtacttg aaaggaaact gtactctctt ggatgggaga ggtactatga tgaccctgac    240
cttcttcaat tccataaaag atcaactgtt catcttattt tctaccaaa ggacttcaac     300 aacctcaagt ccatgcacat gtatgatatt gttgttaaga atcgtaatga gtttacagtt    360
agggatatgt agtactacta attaataatt agttgatttg agatatttt ctcaaattaa     420 ttaatgttgt ttgatttaaa ttaggttgtt tcttgtttta acttaatgtt tggtttgtgt    480
aatttaggtt taagggggt gttttagttt cttttgggtg aggaagctaa ttattacttg     540
taattgtgtg taagagtgaa gttttatggc aataaaaaaa cttggtttgg cttgaaaatt    600
ttatct                                                              606
```

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9

```
aaaggatgag ccttcttggg                                                20
```

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10

```
ccactatcca ctttaagacc tctatc                                         26
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
aaacacttcc agtcagta                                                  18
```

<210> SEQ ID NO 12
<211> LENGTH: 20
<212> TYPE: DNA
<213> ORGANISM: Artificial Sequence

```
<220> FEATURE:
<223> OTHER INFORMATION: Synthetic

<400> SEQUENCE: 12
ttgttgacaa tctaaggaag                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cttgggatgc gtgcactttc                                              20

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
gaacttttcg gagtccgttc g                                            21

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
acccctcaca ccctcttaca                                              20

<210> SEQ ID NO 16
<211> LENGTH: 23
<212> TYPE: DNA
<213> ORGANISM: Artificial Sequence
<220> FEATURE:
<223> OTHER INFORMATION: Synthetic

<400> SEQUENCE: 16
tcaaaactca aataacaaga atg                                          23

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
tcatgaatag gcaccaataa                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ggatttcaaa gtcatgacaa                                              20
```

```
<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
tacgtacatg tggcattt                                                   18

<210> SEQ ID NO 20
<211> LENGTH: 25
<212> TYPE: DNA
<213> ORGANISM: Artificial Sequence
<220> FEATURE:
<223> OTHER INFORMATION: Synthetic

<400> SEQUENCE: 20
tcaaatttta gacctctaag taaaa                                           25

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gtcgtggcta aacttaattc                                                 20

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
aagaagctcg agaactaatt t                                               21

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ccattgtgga cactcaattt                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
tgtcacagtg aacatgtatt                                                 20

<210> SEQ ID NO 25
<211> LENGTH: 23
<212> TYPE: DNA
<213> ORGANISM: Artificial Sequence
<220> FEATURE:
<223> OTHER INFORMATION: Synthetic
```

<400> SEQUENCE: 25
cttgatgaat tgactttcaa atg                                                    23

<210> SEQ ID NO 26
<211> LENGTH: 23
<212> TYPE: DNA
<213> ORGANISM: Artificial Sequence
<220> FEATURE:
<223> OTHER INFORMATION: Synthetic

<400> SEQUENCE: 26
cccttgttat ttaacattga ttt                                                    23

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
gcagtaataa agatctgaac aa                                                     22

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gtgtttctaa cattcaagca                                                        20

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
tcaaattgtc ctgtgcaa                                                          18

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
ggataaagat tctccaggtt                                                        20

<210> SEQ ID NO 31
<211> LENGTH: 17
<212> TYPE: DNA
<213> ORGANISM: Artificial Sequence
<220> FEATURE:
<223> OTHER INFORMATION: Synthetic

<400> SEQUENCE: 31
ttgagctcat catgcta                                                           17

<210> SEQ ID NO 32

```
<211> LENGTH: 32
<212> TYPE: DNA
<213> ORGANISM: Artificial Sequence
<220> FEATURE:
<223> OTHER INFORMATION: Synthetic

<400> SEQUENCE: 32
ccacattttt tattagatta cccagaatat ct                          32

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
gcccctgggt ttttggtttt                                        20

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
atacttgttg ttgggcaggg g                                      21

<210> SEQ ID NO 35
<211> LENGTH: 25
<212> TYPE: DNA
<213> ORGANISM: Artificial Sequence
<220> FEATURE:
<223> OTHER INFORMATION: Synthetic

<400> SEQUENCE: 35
ccataaattg ttgtccactc atcca                                  25

<210> SEQ ID NO 36
<211> LENGTH: 22
<212> TYPE: DNA
<213> ORGANISM: Artificial Sequence
<220> FEATURE:
<223> OTHER INFORMATION: Synthetic

<400> SEQUENCE: 36
agccattatg ttgtacctgt ca                                     22

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
tgggtttgga tgggttcagg                                        20

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
``` tcttctttt cttagctcct ccacc                                    25

<210> SEQ ID NO 39
<211> LENGTH: 22
<212> TYPE: DNA
<213> ORGANISM: Artificial Sequence
<220> FEATURE:
<223> OTHER INFORMATION: Synthetic

<400> SEQUENCE: 39
aaatgttgaa gctgaaactt tg                                      22

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
aagaagctcg agaactaatt t                                       21

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
ccattgtgga cactcaattt                                         20

<210> SEQ ID NO 42
<211> LENGTH: 22
<212> TYPE: DNA
<213> ORGANISM: Artificial Sequence
<220> FEATURE:
<223> OTHER INFORMATION: Synthetic

<400> SEQUENCE: 42
tcccactcaa ggtaaatgtc ta                                      22

<210> SEQ ID NO 43
<211> LENGTH: 23
<212> TYPE: DNA
<213> ORGANISM: Artificial Sequence
<220> FEATURE:
<223> OTHER INFORMATION: Synthetic

<400> SEQUENCE: 43
aggaatgggt gtatcaacaa ctg                                     23

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
cccaacccca cgaatagagg                                         20

<210> SEQ ID NO 45
<211> LENGTH: 20
<212> TYPE: DNA

```
<213> ORGANISM: Artificial Sequence
<220> FEATURE:
<223> OTHER INFORMATION: Synthetic

<400> SEQUENCE: 45
gacctggggc ctaactcaac                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
gactgcagta tccttccgca                                                    20

<210> SEQ ID NO 47
<211> LENGTH: 21
<212> TYPE: DNA
<213> ORGANISM: Artificial Sequence
<220> FEATURE:
<223> OTHER INFORMATION: Synthetic

<400> SEQUENCE: 47
gatgctagga cagccatgtg a                                                  21

<210> SEQ ID NO 48
<211> LENGTH: 1103
<212> TYPE: DNA
<213> ORGANISM: Solanum lycopersicum

<400> SEQUENCE: 48
gatataagga attcttgttt tttttatttt tttattttg aaaaaggatg agccttcttg           60
ggatgcgtgc actttcgaag tcattaaagt cgaataagaa gaaagaaata tcttcgtcat         120
tttgtttctt cttaaaacaa gctacgaaaa agttttgag gttataagtt tcagagtatt         180 aattttata gtattagagt aattcaacat ttataaaagg tcaatactaa attagatatc         240
tataattaca ttttgattca ttgacttaat gatataaga tgttgttatg tttttgtag          300 aggaaaggtg aatgagaatg ttttttgtat gtgtttgtag tttatgatga gatggtttgg        360
atgtaagagg gtgtgagggg tttatataga gggttttgga tgcttacaat tatattgtgt        420
gagtttgata gaggtcttaa agtggatagt ggggtagtct cccccgtttc tggcatcttt        480
agaatttcga gattcaaacg agtatttttt tatcacgatt aattatatat tttgtattat        540
tttaaataat ctgttacagt aatttatagc agttttttaca taatttctat atatactaat       600
tttatctcaa aaatttgtgt gtatgaatac acaagaaaaa tcaaaaagtt taatttctga        660
aaaacaaatt atattgcata aattgaaata agaaaataa ttttaaggtt aattattacc         720
acttaaatat gttgatagtg aagaaaattc tttacgttta gaatgtgtgt atcaaaattg        780
tgtagcaagt gaaaagtttt gagggtatt ttacaactaa tgtacgagaa gattgtagga        840
gaaacatatt cttgtaccct taagaatat aatatacct tgttactatt atcaaagtgg         900
acgaatatga cattttgttt gcatatataa gtgatgaaaa tttcccaact ttataaggac        960
gttgttcatg aaagcaaaaa attaaaatta taaaatttta ccatcaaagg aaataagatt      1020
attggagtaa aaagtgtata tatatatata tatattgatt attgatcatg caagtagaga      1080
attgacacgt gtttgagaac att                                              1103
```

```
<210> SEQ ID NO 49
<211> LENGTH: 631
<212> TYPE: DNA
<213> ORGANISM: Solanum lycopersicum

<400> SEQUENCE: 49
atctcatcat aaactacaaa cacatacaaa aaacattctc attcaccttt cctctacaaa      60
aaacataaca acatcttcaa caatcatgtc tggagtttgg gtattcaaga atggtgttgt     120
ccgtctagtg agaactccg attgccacgg ggcgaacgga ctccgaaaag ttcttgtaca     180
tcttcctagt aatgaagtca tcacatcata tgcagtactt gaaggaaac tgtactctct     240 tggatgggag aggtactatg atgaacctga acttcttcaa taccacaaaa gatcaaccgt     300
tcatcttatt tctctaccaa aggatttcaa caggttcaaa tccatgcata tgttcgatat     360
cgtcgtcaag aatcgcaatg aatttgaggt tagagatatg taaacaaaat atggggggaaa   420 aaagggaagg agttgatcat ttgaatgtgt tttttttct tttttttgct ttttttggt      480 caagtgtgtt gtaattaagt ttctatcgtt taatttgtga tttgtttcac aatgttgcta    540
aggttgtaat ttggaaagtt gtaagagggg aaatgttgta tattattaca agtgaatgtg    600
ttttattata tgatatatat atatataaga g                                  631

<210> SEQ ID NO 50
<211> LENGTH: 19
<212> TYPE: DNA
<213> ORGANISM: Artificial Sequence
<220> FEATURE:
<223> OTHER INFORMATION: synthetic nucleotide

<400> SEQUENCE: 50
tctagtggag aactccgat                                                 19

<210> SEQ ID NO 51
<211> LENGTH: 20
<212> TYPE: DNA
<213> ORGANISM: Artificial Sequence
<220> FEATURE:
<223> OTHER INFORMATION: Synthetic sequence

<400> SEQUENCE: 51
aaaagttctt gtacatcttc                                                20

<210> SEQ ID NO 52
<211> LENGTH: 20
<212> TYPE: DNA
<213> ORGANISM: Artificial Sequence
<220> FEATURE:
<223> OTHER INFORMATION: Synthetic sequence

<400> SEQUENCE: 52
ccagattcat ctcggggagc                                                20

<210> SEQ ID NO 53
<211> LENGTH: 20
<212> TYPE: DNA
<213> ORGANISM: Artificial Sequence
<220> FEATURE:
<223> OTHER INFORMATION: Synthetic sequence

<400> SEQUENCE: 53
gagctgctta accgtgacct                                                20

<210> SEQ ID NO 54
```

```
<211> LENGTH: 20
<212> TYPE: DNA
<213> ORGANISM: Artificial Sequence
<220> FEATURE:
<223> OTHER INFORMATION: Synthetic sequence

<400> SEQUENCE: 54
gagctgctta accgtgacct                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic sequence

<400> SEQUENCE: 55
cgtgagttct tctggccctt                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic sequence

<400> SEQUENCE: 56
gagggcgtgg atatgtcctg                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic sequence

<400> SEQUENCE: 57
ggcgacctcg tattgggaat                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic sequence

<400> SEQUENCE: 58
gctctcgatg agctgatgct                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic sequence

<400> SEQUENCE: 59
atttgtgtac gcccgacagt                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic sequence

<400> SEQUENCE: 60
```

```
taaatagctg cgccgatggt                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic sequence

<400> SEQUENCE: 61
ggcgacctcg tattgggaat                                               20

<210> SEQ ID NO 62
<211> LENGTH: 22
<212> TYPE: DNA
<213> ORGANISM: Artificial Sequence
<220> FEATURE:
<223> OTHER INFORMATION: Synthetic sequence

<400> SEQUENCE: 62
ttcccctctt acaactttcc aa                                            22

<210> SEQ ID NO 63
<211> LENGTH: 20
<212> TYPE: DNA
<213> ORGANISM: Artificial Sequence
<220> FEATURE:
<223> OTHER INFORMATION: Synthetic sequence

<400> SEQUENCE: 63
ccagaaacgg gggagactac                                               20

<210> SEQ ID NO 64
<211> LENGTH: 29135
<212> TYPE: DNA
<213> ORGANISM: Solanum lycopersicum

<400> SEQUENCE: 64
ctataatgct tcaatccctt tagtaattag atagtatcaa taagttcagt gtaattagaa    60
tacttcaata agttcattga acaaattgaa gatacctgga taggatttca ttatcacatt   120
acaaattgct ggtccttgaa gcataatatt taatctagag aagatgacct cttgtttgtt   180
gaatgtgcta ccattgaaat ttgattgttt ggtttaaatg tgctactttt gaaatctgag   240
tagtctagtg aagcaaggtt taagttgtgg ctgcctgttt atgttgttaa gttactttac   300
attttccttg tttgttcaga ataatcgat gctgctagct ttcccattat gcttaaaaat    360
atgtttattt ttctatttta ctacctactc aattgttcag atctttctaa tttcactctg   420
aggctttaag ttttgtttta attttgttag tttgatgatc tgaaaagtct ttctctatta   480
aatatatttc tctgttaatt gttatatgac ttgcattgtt ttttcaccct attttaagta   540
tgaactcata tctttctttt ttgacctaaa gttatgtaac ataattagtc tatttcatgt   600
gtataatatg ttttaaatga atccaaggtc agggtatcct gctacatatt gtgtcgatga   660 cacttttttgt ctttgaatcc agaaaaaatg agtataacgg aagttctgga tgttgagatt   720
aactcatgag ttgtgttgat aacaatatat tagttttta attcaactca tatagttaac    780
aattgataaa tttgtaaatc agtaatataa gtattctttc tgcaagaact tataaattta   840
atgtcagata cttatattac ttttgattta tgatatccct cctaacaacc tcttcaaatt   900
tatacaggct aaaaccttct aaaatataac gtgatttctt ttgtatagac tattgaaaaa   960
```

```
gtttgagatt caacatcaag tgatttatat cgacatgttc atatgaaaaa tcatttgttg    1020
gtgaacgttc tcgaaatgtc catgtaagtc taaaagttgg aggtgttttg gttctgtcat    1080
actgtagagt gtatctgtga ctgttgtttg gtataactct aataattttt tgagactttt    1140
cgatgcaatt ttagtgtcgt ttagatgcga ttctagtgtc gttttttgtgt gactctagtg    1200 caattgtttt tggtgcaatt ataattttgt tttagagaga aactaatgct actgttttttg    1260 tgtaattcga ttgttctttt aagacttatc ctgtgcaatt ttagtgttgt tttagtgtga    1320
ttctagtatt gttttacttt gaccctagtg tagttaattt tggtgcaact ctagtcctgt    1380
tttagtgaaa atttgttgtt gttgtttcag tgtactttag gtgttgtttg aggctcttca    1440
ctcgagcatg aacttcttct tattgctaca tcgaccacat tcactccatt gcctgtcatg    1500
cttacttgca actagtacat caaataacaa gaagagatta atgagccaga actctgaaga    1560
taagtaatat aatttgcatt tgtaataacct caaaatcatg aataggcacc aataatgaca    1620
tagcattctt gttatttgag ttttgataga ttactttaca gttttttcat atagaagaaa    1680
tgaatgatcg gtaaattta gtctttgtag ttttctggat gtgcattgta ttgcagtatt    1740
catagaattg atttatacta tctgctttga ttagacagtt attagtatac acctctggtt    1800
ataaccaact gaagaagttt gatagtactc ctgtcaatat gcataagtta gtattgtggc    1860
atatatataa actactttag ttggtatgag tagaagaatg acataaactt taataagttg    1920
gtaatcacac gtttcctata tcctccaaga gaatagacag attgtagcta ctaattttgg    1980
ggacaagttt ctgatctaga aaaatatcgg ttatctttca gattattcga aaagaggccg    2040
agaatatctc attatgcgta aagtactgta gtctagcagt tgctatactt tgtgtcaggc    2100
ttttgttgcg attcttatgt cattttagtg tgaatctagt gcagttgttt tcatgtaatt    2160
ctgatgttgg ttggctaatt tttgagtgtt tctggtgttg tttgataaca gaaatcagtt    2220
tgttttgagg ttcatctatt ctagaaatgt gcgagttcaa gtatgatctt tattctgcaa    2280
tacaaaggag ttcaaaatta tatgtctaag ttaattacta caactttataa atgcatttc    2340 atggaccaac taatataagt tgcactgtca ccatttcatt gaattttcct tgcaacaatt    2400
atcaactaat actatgcgct agagtattat atgcacatgg aaatcagata gcctattttg    2460
ctatagcaac acagttcttt ccttggaaga taatagagat gtcttttaag cttaaaagct    2520 tgtgtgttttt tatgcatttt ccttaaaaaa ttattttgtt ccctatcttt taatgctttc    2580
tcattttctc tagttattat aggaaaaata tgaagaaata ttacggaaaa acagtgtatc    2640
aatctgatat tgatattgat caatgtgaag catattatca agttgcgggg agagaaaaga    2700
aaagaagaat atacggtctt ggatttgaag caagaattta ttaggggcaa aatctttatg    2760
gttcataatc attaccacct tcattttctc aatcaacatc gataacaaat atggatgagt    2820
ttgtaaagca aatgatgtct gcactaacta gtcatcttgt tcctattatt gttgagcagg    2880
tgcaagcatc gattactcca tccggcaatc catcgattgt gacacccata gtgcctgttg    2940
ttactaatgt ggacgaggtt gataccttaa tttcaagtga agatcgtatc ccttagtctc    3000
ccacaacttt agttttttgat gatgtcatat ttttttgaac gaattgcgta gcaatatttt    3060
gatgaacgta ggttcattta atagcacttg atatatttct ttggatatat ttaacaaaaa    3120
aatatgtggt tttgaagttt tctatttata tattatgaat tggctatgag tattatatta    3180
tatgaatgtt tagtcattgt tatgaaagaa tgttgggatg gatcaacaac gaattattga    3240
aggcctgata tgttgtatgt tgtgacggaa atttcatcgc aaatttatcc aaaatgatga    3300
aatgaattat taaattagcg acaaaactat ataaatataa tgacaaaatta ctccgtttct    3360
```

```
aacatgtgtg aacgaaaata tttcgtcact atgacgtcgc taaacttgtg acggaactta    3420
tttttcatcg tagaatcatg aaattagcaa caaaattata taaatataat gacgactgcg    3480
acgaaaatgt ttcatcacta tgacgttgct aaacttgtga cggaactcat ttttcgtcac    3540
taagagctta ctaacgagcg ttatagcaac agtcaatact ccattgctaa tctgtcacta    3600
atcatgatta gtgacgaatt ttcattatat agtgagggat tgtgtccgtt gctaaacgtt    3660 gttttttag tagtgttagt ttggccactt tggtaactaa caaactatat aaaatacaaa    3720
acacacataa tatcataaaa ctttatgcat gtgcataatt ttaaatattt tagtttgacc    3780
actttggtga gtaacaaact ataaaaacat tatatatgca tcaagtgatc ataaacatga    3840
tgtgtgtaga cgttaatttt ctctagtttg gccactttgg tgactaacaa actatataca    3900
tacaaagcac acctaatatc ataaaatttt gtgcatgtgc ataatgttaa aaattttagt    3960
ttgtccattt tggagactaa caaactatag aaacataata catggatcaa gtgaacataa    4020
atatgatatg tctagacatt aattttttt taatttgac cactttaatg actaacaaaa    4080
tatatttcac taaatataca catattattt attacataat gaccacttta atttattaca    4140
caatctaaaa taaatataat tattacatta ggaaaatatc aagattgttc agaatttctg    4200
catcaattta tgaaaaacaa cctacataat tatatattta caatgttttt aataaagtca    4260
ctaaaagaaa aaatcttttg tctagtctca aacatcatct tgagtttccc ttcacttata    4320
tttcatttct tcgagatatt ttttttaaat atcctttgtt taggtcagaa aaacatatgc    4380
tataatatgc aaacatatgt taataataag ttataacatt agaaaatatt tgtttcatac    4440
ataattgata attaatgtta ctccattatt taaataaatc aacagatttt tgatacaata    4500
agaaaataat ttgtataaag aatctgtggt aagtttcgtc accaatacat gcaatcaagc    4560
aataacatag gacgaaatag atatttttt tatctctttt atatacgaag gttatccgtt    4620
caaataattc tcactccgat gccacatgca agattaaata ttttataata taatattagg    4680
atcttgaaca caataatctt acataaaaat tgatagggac acatacctga ttaagaaaac    4740
attatcagac agaaaagtgg aatcgttagt cgtaatatgg tttctaccct acttaccctg    4800
actttatgtt accacaaccg tcagcgatga aattattgtt gaaaatatgt aataaccctg    4860
atgggtggag ggaggaccaa tttatagagg ttatgattta atctggtatg tctatgaagt    4920
aatcaatcta cggacgagat ctactatttg tggtattact tgaattacaa gtaaacttga    4980
atcataaata aaaataatt aataataatt aaataataat tcttacatct tcaccttcaa    5040
gcttcaaatt caatgatttt ggtatgtgag atttttattaa tgaatattct ttcaaccatt    5100
gagtccttaa aaaacctata ttttcatata ttaaattata tagaaatcta ggattattat    5160
gatcatcata gatttaatgg aaaagggtct aaaatagtct cgaagtattg gaaatggtac    5220
aaaattaccc tccatctacc tattggctcc aaaatgtcct tctcatctat ctattggctc    5280
caaaatactc ttgtcatcca cctttgagtt caaaattgac cacttattta actattttaa    5340
aattaaacta tttaaatatt ttttaaaata cttggcgctc aactattagt tataatttaa    5400
tttattaata taatttataa accaactcac tagcgactca ttattaacta aaccccaccg    5460
aattaataaa ccaattataa tatcaaaatt gtcataaaca gtactactaa aacacgacga    5520
aattatagat tcctgaaaat gacatccaaa attattcgac tctgaatcaa agccccaatt    5580
aaatttaggt tgaacccctta tttaggagga aactttttaat aggaatttat atcaagcttg    5640
aaatcaaaat ctatgattaa agttaaagaa gtagtacatc cgaattaatt catgcacttt    5700
```

```
tttaaatata ttttttataaa tatttatggt ttgttttaaa accttaatat attattttt     5760
taaaaaaatt atctatgaag taacatcaca taattgagac gaacgaataa ttaagatgaa     5820
catagtcata cttttaagtt tatcattaat ttttatttag acacttgaat gtatgataat     5880
ttacttccat agatattttc gcctcaaatt ttcaaaaact ctcattggaa gtagctttct     5940
tgttgttgca ttagtaacgt gacgggttta ttatttcggt gaggtttaat tagtaatggg     6000
tgggtagtga attgatttat aaattatatt aataatttaa attataacaa atagttgagt     6060
gcaacgtatt taaaaaagta tttaaatagt ttaaatctaa aaccgttaaa taagtggtca     6120
attttgaatc caaaggtgga tgacaagggt attttggaga caataggttg gtggggaggg     6180
tattttggag ccataggtg gatgaagagt aattttatac cattttcaat acttcaaggg      6240
tattttaggc cctttccgta gatttaaatg gtgattata gtttctcttt gttactaacc      6300
taaatacatg tttcccctta aatattagca taaattatgt acggagttag gagtattatt     6360
tgagactgag caaatataag gatgaagggt catccgtcaa tttaggacaa aagcatttac     6420
actatgtttg gatcatttt attcattgta ttgtattgta ttgtattgtt actataccta      6480
caatgtttgt tttaattgtt acttaaaatg cattgtattg tattgttaaa tttcgttgtt     6540
acgaaacaat gcaaacccct attttgtgga acaaccaatt cgatgtgttc ccgttgttac     6600
ttagtttctt tttccaatta tatctttaca taatatttta aaatactatt ttactcttta     6660
ccttaattat ttaaacatag tcaaacctcc tattctagaa taattaagga tatttaagta     6720
aatttataaa ttacaataca gtacgataca atcaaaccaa acaattaaaa tgttactaaa     6780
caacaacaaa caatacaatc tagccaaaca ttgtatctac catacaatac agtacaatac     6840
attatgaaat aatgggtaac aatgatccaa acaaagtgtt aataacaatc tctaagttgt     6900
agaacaacct tcaccagcaa tcaaatttt taagttgttt agataaagat ttgacttgat      6960
gttcattaaa atccgtcatt gagaagtttg aaaactcaaa ttttgatact caatttacca     7020
taaacgtgaa tcatttcaaa tgaataaatat attgaaagaa ttgagagaag ctcatatcta     7080
aaatttgagt agtttagaag aaggtttgag ttgatgtaca ttgaaatctt tcaacaaaga     7140
gcttggaagc tcaaatttaa aactcaccct accaaatatg agttatttcg agagaataat     7200
atattaaaat attaaaacat caatctcaaa ttgatcaagt gggctttcta agagatccgc     7260
attcgtattc actgcattat tcgtattcac tgcattggaa taggctgaac cccctacaat     7320
ctcgttaaat tgttttaggg caaagtcata gtgctcaccc tgtttgtctt ttaaatgttc     7380
taaaatttct aagaggagtt catatctata atttaggact actaagagga atttgaattg     7440
gtcgggattt taaaaaaagt caacttattg aaaaaaatgt attgctttaa tgtataaata     7500
ttgtataaca atgtatatta tatatatatg tgtgtgtgtg tgtgagtgtg tgttttata      7560
tatttactag taatatatta ttattttttct agagatagca attttgtctc tatatccata    7620
cacacaaata tttaaatttg aaaaatcaat ctaaatactg aatttgcagc tataaatatt     7680
tgaagcaata gattgaaggt ttggagtttt aaatgtttaa aagttcgaaa atttgacagt     7740
ttgaaggccc gaaattttaa aatatttgaa gatgcaatca acaattgcta ttttatcat     7800
acatgaactt ctaagaaata gatgagcaca tccatatatg ctgatatata tgcatcatat    7860
aataatcttg aaactgtcat acagattgat agatattaat catcaaccaa acacaaatac     7920
acaaatatat atatatatat atatatatat atatatatat gtatgtatgt atgtatgtat    7980
gtatgtatgt atgtatatgt atatatataa tctaatagag gcagagttag gtggggttc      8040
gtgggttcga acgaaaccat tagctttct gaagatatca tagatcatta aaaaaattaa     8100
```

```
tcgaccgttc taaagaaaat ttagagttcc aaactcttaa ttgtggctct tccccggtcc   8160
ataaacattt tcagactgag acatgaatgc tacaaaacta tagctttaaa taaatacata   8220
gatacttggt ataacaagag tataaaacag aactacaaca catgtatact tgtatatcat   8280
atactttaat gttactaaaa tttgaacttg taaaaaaata aacaagtatc atatctaaaa   8340
ctttaaaaca catataaaaa tcttttggtt ttttccctct tcatagacgt taaaggagag   8400
agagccaatt ttttatgctc tattttttt attagaaata ggtagtattc taaaaatgca    8460
caatttatga tttcagcagt tttgtatatg ttgaaactat caccagacta ggtgattcag   8520
ccctgtgata taatattcat ttcgtttcaa aataaataaa ttacacagat gttagttcaa   8580
tattactttt catttcgttt caaaataaat aaattacaca gatgttagtt caatattact   8640
ttctgttttt agcttttaa ttgtcaatac ttcaatgcaa taaaaacttc ttaaattcat    8700
aagacaaaaa attcaaatga aggataaaat agaagaaaat actaattatt cctatagatt   8760
gactaattaa ttaatttgac tatgaaaaag gtcttactaa gccacttatt ttgaaatgat   8820
cggagtaact atacaagtat tttggtaaac tacacaaatt ggatccatta ggcaaagtgt   8880
tttctcatat cggacgcaag ccaaactatt taccctaatt gaatccccgg tccaaactat   8940
tcacctgact atcctttgtt ctattcattg aactattgct tcttcattct tgataccgtc   9000
aaaagtgaat tatgtatgtt atatacatgt tttataacta ttttaaaata tgttatgttt   9060
gtttggtgag aaattaacac attttattaa aatgtgcgat aaattatatt atccaccaat   9120
aaaacttgta ttacatgtgt tttatgaatt gttctattta atatgtatca ataataaatc   9180
ataaatgtat taaataatc aaataaaaaa aattgttatt tctataaatg ataaatattt    9240
ttcttgctta tgtaaatttc cctttttaaga ttgtataggt attacataaa gtattcatac  9300
cccaatccaa tcatttgagc ccatggacta gagaaatggg ctgaggatcc tatgtgatgt   9360
caacctttct tcttggattt cgatagacca gaaagagaat attaggccta aattcaccat   9420
ataatatcac tttcgttttg atttatgtga aaatatttgc ttagacatag aattttttcc   9480
cctgaaattt atggtctata aggaatcata ctttttttt tgaaagattg tccattctgt    9540
tggaaggaga atatataaat tatatgtgca agaataaatg agtttaaatt attatattag   9600
tacgtagttg tatggatgcc catggaatga acaatttgaa gatctttgtt atgaagaaac   9660
tatttctgtt gagatggcta tacgcttcaa gatatcaact aaaacaactc gttacaaaag   9720
tatatatatc cttttctttt aattggatcg atatttaat tgtgtaaata atatattata    9780
ttgtatgcaa ttgagaggac taatagaaaa atgaaaatg attgtgagaa attgcataaa    9840
gcttttgtga tttgaataat taaaacttgg attttttat atttttttt gcttctttac     9900 aaaaagtatg atttggttcg gtagatataa tctttggttt gagtatggtt aatagaatgt   9960
atggtttgat tcctttgcca cttttaact ggatcatatt tgattggata taaaatatga    10020
atttacgtaa atgagttaca aaggtctatt atttgaagaa aaaaaagaa tttcaatgac    10080 atgacatgtc ttttattaga gaataacact tttgacgtgt ttagtagttg catagtatga   10140
aaataatttc tatcaaaata taagtgatca tccaggaaac aagtcgaata taaatgaaaa   10200
ggatttgtag tatcaacgtt tagctttat aaccactata taattctttt aaattaggta    10260
aagagttatt ttacgtaata taattctcat ctccactttg ttatgacata atcaagagag   10320
tcattatcaa tatattaaga atgtaacgga tatgacaatt ccagcttctt attgtgttcg   10380
tgtgtaatga atggaataga tccttaattc cataatttt accactttat tctaaagttt    10440
```

```
tatatacata tatgcatagt tggcctaatt ccatcaattt ttcatgacat attttaggag    10500
aataaaccta aggccctaga aaaaaaataa tcatagttta gcctttaacc taccttattc    10560
ccttttatag ccaaacatac attactttgc aagggaaaat ctcaaataag tttattggaa    10620
atataccaat ttgaagaagc tagccctcac tttttgtata tccaatgaga tttatattgt    10680
ataaacttaa ataatattgt ggagaataga ttcatatttg taaaagggac cataattgat    10740
aaattaatat gaatgatacc attctttaat taagatagac taaggatgct taaaaatgcc    10800
actttattag agaaattcca tatgataact aaaatagcat aattggctaa aaaaaagttc    10860
aagtattggg gatcgtaaaa ttcttttttac acaattcaaa aagtaattag cttgtgaatc    10920
aagccttcta atatttgatt agagtatgta atcatcatct ttatactcaa gaaccattta    10980
gctgacgaaa aaaatgtaa atattccttc atttcaagaa accatgcaaa ataatttatt    11040
gatcatttgt tattctttat tttacataat ctactagttg cacaaccttt ttaaaagaca    11100 aagtttacc aactttgtgt gcatgtagtt ttccaaaggg taccaaaaat cttttttttt    11160
ttttgataaa gatggattgg tccttttgat tagcatgcaa aagataaact taatacaaaa    11220
tttgaaggca caagtgtgac atatatatgt agtgcaagaa tattgtctag tttcacattg    11280
ttgggcttag ggttttggct ttccttttttt atgggagagg gtgttcttca catgggtgtt    11340 ccgaatata atatatgtaa aagagatgga ggagagtgac aacttatata tttgctcgtg    11400
gagaaaaata tgttactccc tccgtttcaa atttgtttgt ctgatttga tttgatacat    11460 agtttctaat aagtaaaaaa gattttgaa ctatcaaaaa ctaaaaatat gaagaatata    11520
ccaagttacc ttgcatctta ttgtattaaa tacgttttgt gaaaaaaaat taaaattaaa    11580
gagtttgcag aaaagaagaa gaacgagaca ttcttttga cacaggttga aggaatcagt    11640
aagacaaata aattaaaatg aaatgagcat gttattctca ttaatatgcc tcatgcatta    11700
ttgttaaagc aaaggatgtc ttgaaataag gtaattggta ggtataacat tgttttcttg    11760
aacaaagttt gtatatggat cctgcattgt atgaaggacc ataaagaaaa gaagcaagag    11820
agtgacatgg catatagatt atagtggcac cacataaata ataggcgcat atgtatatat    11880
atatataaaa taaagaatca aaggatcttc aaggtggcaa atgagaggtt tgtaaagaaa    11940
aaaccagctc atgcaatatg gttccacttg aaagtttgaa ctttcacgtg tgcattgccc    12000
atataccata tgtcaactag tgcttagaa gaatagtaag acacttctag cttgttcttt    12060
tgattccatt ccaagaaagt ttattcaatt catgccaatg gactgatatt gacttatcca    12120
atcaatcttt taggatcaag tctataagga tttagagaat ttgaaagagg cggaattaaa    12180
atttaaaatt tatagattca ttatgtaaga catgatatag acatttaaac tccaaatgct    12240
aggtgaacta attaaacata atactatcta ataaaataga acactcttag ggataatagg    12300
aatcaatggc attgtgaaca gccaaacaac tcactattaa tatcctagag atggattcta    12360
cacactgatc tagggcattt ttgtatatcc ttttatccat gttttgagaa tcaattcacg    12420
tgcataatct catatatatg cctcatgcgt tattattaat gccaaggttg tcttgaaagg    12480
aggtaattgg taggggttagc ttgttttctt gaacaaacac tgtatataga tcctgcattg    12540 catgaccat aaaggaaaga agtagagagt gacatagagt ggcaccacat aaaatagtag    12600
gcgcatatgt atatatcaaa ataaagaatc aaaggatgtc caaggtggaa aatgagaggt    12660
ttgaaagaaa atcaactaat acaaatggtt ccacttgaaa ttttgaactt tcacatgtg    12720 tattgcctat ataccatatg acaatagtgc tttcgaggaa tagaaagaca cttctaagtt    12780
gttcttttga ttccggtcca agtttgttca attcatgcca atggattgat actgactcat    12840
```

```
ccatatcaat ttattctaaa tattagagtt ggaatccaca aatttaatgt tttgttttac   12900
cattttcaag gaattgttgt tgtttacttg tagcaaggag agagggcctc taatctacct   12960
ctaacatgat gtgattatta atccaaccag atggcatcta aggaaaaatg acaatgttcc   13020
tattactttc atcaaaatct tgatcatcta tatcaacaat aatatattta gtaaaatctt   13080
actaagcggg ggtctagaga gaatagagtg tatgcaaatt ttaccactat ctcgtggacg   13140
taaagaggtt atttatgaaa gaaccccaat ttaagtgtat caaactcaaa taaagaaaa    13200 agaaaacaac gaagaaaata taaaaaaaag aaaatcaata ttaagtgtac aagatcaata   13260
gcaataataa aatagtgtga tgattaaaac acaataaaaa catatcactg ttgaaagaaa   13320
ggaaagctaa agaccaggaa caagttgcgc aacatggtac aatcaacgtg tacaactggt   13380
atctgttaaa gagagttaaa gtcacactaa aaatgagcta ttgtgttagt tgatgtagac   13440
aagactctat gtcttatgtt agctcaagat gactaggata aattataatt gcattactag   13500
ttaacctcta ctcttgtaag ttgtgtaatt gtattgtagt ataactctaa gtgtagcaag   13560
gtcggaactc taaaattcac tcatatataa aatcatgtgc tcgatagttc taatcatcaa   13620
tataatcttt gatttctctc attttttctac gtgagattct acatagtatc agagcatata   13680
aactcttcca cacattaaat ctaatatgac aacatgacaa attgcaatgg atccccgtac   13740
caatacttgt ccacgctttc cttcaccacc tcatttcctc ttgttacatt aagcttaagc   13800
ctacaaacta tctcatatga agaacataaa tgatgcaatt gattcaggtg atataattta   13860
cctatgttat tcaggagaat gaaccaatta aagataattg ttccattgaa aaggctactg   13920
aaaaagttac agctattaat gttgagaaaa atgcaaagat agtaacaaca ttgatgattg   13980
ggaggagata aatgtatttc taaaaagttg gatgatcagg cgagcatgta cctgattgtg   14040
gattgataaa atgtcaaaaa agatgtgaac ttgcttaaaa taaacctatt ttcaagcaag   14100
aaaagataaa aaatttcatc ttaaacaaca atataaaatg ttaagttagg aagcaagaag   14160
attgatgaat acattaagaa agtaaaaggt atatggcatg gtcttgcaac cattcataaa   14220
catatggatg aagatagaag agtaatcaat ttttataaag gcttatgtct caagtacaag   14280
accttcaata ctatcatgct agataaaaca ccatatccca acttcaatca attttttttaa   14340 tgctctcaga gattttgata taagggagga tgaagaaaaa gtactataac aaaactctaa   14400
cacgacattc tccgaacaaa aggtagggaa agagaaaatt attctcataa aagaagaaat   14460
aacaactcca gagaaaaatt ctttaagctt gatagacaaa aagaatgttc tcaaaataat   14520
caaagtttct taagtggcaa taaggaaaag aacattacaa aatcatgcca aatctgtggt   14580
agaaataatc ataccgttct taaatatttt tacaggtggg gctactctta tgaatttaca   14640
aatgaactac cataagcatt aggtgttgcc aatatgcagg atacatctgc tactgatgac   14700
attttgtatg tggactcagg atccagtagt catttgaaaa gtaacttagg tattccatct   14760
accttaaaca ctacgttaaa cctaataaat cattattaaa aatggttcac aattagacat   14820
aatatatgtt gaaaataacc tacattaggt ctaaaattat aaaaggtctt cgtagtccct   14880
aagattacta aaacctactc tcagttaata tacttgaaaa agacattgca ctcttaaact   14940
taatgaaact aattttgttg taaaaaaaag acgacaaggg cattactaga caaagaatct   15000
aagagaagtg gactctatgt tttagaagat agtaatttct atgctctaac tgttatacaa   15060
gtcttgaaga catcagaaaa cttttaacat tctagattat gacatcttag tttgacgtta   15120
taaacttcat gaaataagca taatatccaa atctaaccaa catgcatgtt atatcttcac   15180
```

```
attaggacac aatcaacata taaatcattt ccttcacatt aagccttcac ctcaagtaac    15240
cctcaagcta tactttgtgc tatgtatgaa tagcgtctca taccaccatc cacacgtcat    15300
agaacttctc aagaaaccat tatttacatc tcacatgata ggaataaacg tttataccga    15360
catagaccat gaaagctaga tcatgaaatc cgatgtcata taaccccaca ccgtaaaaag    15420
gtggtttact tgcctaaggt agactagata atatcttagc tttggtagaa aaccgttgta    15480
acatatatcc tatgtagcca cataggtata ggataggaag atgtttattg gaaccctagc    15540
ctaacgttgg gagagttttc atcttactat attcactcgg tgattagcct acattcccgt    15600
agagtagtcc attcatatta ttgtacttga gagggctacc tatactgggt ctaccgactc    15660
taaatacatt acaaaagaaa ggttcaccaa tactaggtct gacgatttaa ggtacattaa    15720
agataactca ttgacttccc aagaagggta ccctcaacat tgggtctacc gatacaaggt    15780
tcatcatgta acacatggaa gggttaccaa tacttgatct accggtccaa ggtttatcat    15840
tcattagttt ttacactcat cataaagggt gccattaaca tcgggtctac cagttcaaga    15900
cataacctag aatactttac catttattca tgaaaggtct accaacatta ggtctatcga    15960
ttcataatca ttacattcat tcattcaaga agaggatgcc taaatttatc aattcaaagt    16020
gtacaataca ttgaagaaca acccttcaca ctctatcatc atcattaatg agtgtttaag    16080
tgagaataaa ccttcaatca caacacaatt acattttaag cattatcatt gtactttcat    16140
tgagatcaca catacacttc acatttcgat catagattga tccttcatgc atatagaggt    16200
acaaagaaaa tatttatcaa tttaatacca taatatgcat agtaagtaaa cacctcaatt    16260
tttaaagtgg atcaacatct aaatcacaat tcaacattaa cattcaatca taacttgcc    16320 ctatcaaaac cataatcaaa attcaccaac aaaatcctag aatacttcaa ttaggcataa    16380
tatatacatg attaaatgaa ctagatcaat ataagtctta atcaattcaa cacacattct    16440
tcataatcta tcaattccaa atcacaaaat acaatataga aatttgggga aagcatgggt    16500
tctagaagaa attcaccata aattcatctt taattccaca attgatttat aattcattgc    16560
aataaagcct ttgaaaaact ttagaatcaa accgatgcta ttgaaaagta ggattttgat    16620
caactttgaa gacttgaaat cactttaaaa ttgactcctt aaatggaaaa ttggacaagg    16680
atcaagacta ccatgcattt actataagag tcccatgaaa atcccttgaa aaacttgacc    16740
ttgaccttgg aagcttgaaa tcttcacctc caatggaggt ttctagagag agaacttttg    16800
gaggggaaga gagatttgta ttttgggatt tgaaataatg aattgtaaaa tagggtttag    16860 atactttat tactcttaaa atactttgat taacctaaaa tgatcgccta aacacttaaa    16920
aggtcgaaat aggaatttac cactaagccc ttaccttggc tgagttttac aacgaccacg    16980
acaaccaaac cacggacaat gttctggttg atgccccaac ctggtcaagc ctggttcggg    17040
gatgcagctt ggcaataagt cccttaactt acgaatcaag accacgagtc gtggtttgac    17100
ctatggggtg tggtccccct ccttaggtca ccacattttt tgcaactttc tcattttggg    17160
gcagcttggg tttaggctaa gggtcctact caaggacccc tagggtgatc cttgggggt    17220 cacactttga cgtctctaac ccctcaacca tggttcggga caatactcta cacacacaaa    17280
ctccaaagca aactcaaaca cacactagtt aggctctagt ttcactaatt cattttatgg    17340
gtcgttgtac tatgtctaaa caaggtaagg agaatcaagg aactgactga attctaggga    17400
cttgctgctt attcttggga ggtttgtttg acttttcctc ttcttttgc tccaagttgg    17460 gtgattttg tagaatgagg gttttgggta tgtctgacta ggttattaag ctttagacta    17520
agcaaaacgt catagtttag gtattaacaa cgtaatttaa attcgtaatg catagggaaa    17580
```

```
acaccaagac gaccctgact taaagttggc gaagggccat ccacgagggc actgacgaac    17640
cgttgatggg accacgaccc gtcaagtggg tcgtggtttt tgtccactgt tactggctct    17700
tggtacctcc atttacagtc cacttcacag atcgtgtgaa ggaccagggg ccatgaaggc    17760
tagcatgggg tcaggtcgac ggaccaagcc atgactcttc agtgggacct ctacccgtgg    17820
agggcttcgt ggtccaccac tttttgatgg gtgtgaacca cgatgagtat gacgggcgtg    17880
gttcctttca cggcccgtga acccctccat ggttcatcaa attttttggtt ttcagtctta    17940 gctaagtttt gaggtgttac aagggtaatt tgatggatag tatatatagt cttttagatt    18000
atttcttgtt agcttctacc aagatttgta gtgtttcaac tttggttaat aaagagaaat    18060
ttgttcagta aaaaataat ccaaataaac tagaaactca tgaacaaatg gtccaaatca     18120
ctccttagta cctcaaaatt cgtgcaaagt tataaatcac catgcaaaac taataaaatc    18180
accaaaactt aaatccaaac tcattaattc aaaatgttga cttttggtca aacttcttaa    18240
ataccaaact tgtaaaacta gaatttcctt caattcaaag tcttttacta atcactcaaa    18300
tgattgaatc aatattacca tgatgagatg gagtaaaaaa acttgccaat tgatgcacat    18360
tagtatgaag tgtagaatta gtgaaaggta ttaattggtg gaagaggatt atattctgaa    18420
aaagaagtta gaaggtggtc catatatatt ccatattgag gagattcgga taaattatgg    18480
tgtatagagt aaaggttaaa agaaatggga ggattttgag aagtggtcgg gttaattcaa    18540
gtcacaagga ccacatttca cgagaagaaa ataaggatgt ttcatttta tttattttt     18600 cctttcaagt ttgagaccat cttgctaagg aaaagagatt tgtatgtcca aaagcactac    18660
aacaaacaac aaatatacat ttctaaccta ttaattataa aagccacgaa tcttgcaata    18720
gctttatttt cttttcaaga tcgttctctt tctcatcttg ttacttgttt acatacattg    18780
tatactagat ttcactttt tttttgaaaa agaaaaaaga aaaagaaat cctttagaca      18840 tactaattac atggagtgtc tactaatcat taatgcagaa atgtagttat ttctattatc    18900
tttggttttg gaagagagcg aagaaaacaa taaaaagaga actcagactt gggattggac    18960
tctagtgata tatacatact ccttgctaat cagcttatta attcatctat cctttgttga    19020
agtatgtgtt tatctgatac tatattaaag tgtatgacca tttcatctaa aggtttattt    19080
agagagaaca aactttat agttaatcat attgtcaaca tctttagtta gggattttga     19140
actcaagact tcctgaatat atgactccct ttcgggaacc attttatatc cgatagtgga    19200
tatccactgt acaacgtgaa gagaaattt aatagcttag ttgattggtt agctaaactc     19260
tcgcctcgtt ggtgattgtt aactatatac agtgacataa gtgcttgtta cttaggctaa    19320
cactctatgg tcatgaaaag tgattaaaaa agagatttaa agagtaaatt aaagggtaga    19380
gaaagatagt gcacttaata tcataatcta ctcatgcaat gttttaatta tatatatttc    19440
tcgtcattct tctaatttta attctaactt atcgactcca aaatataatt atagtagtac    19500
ttataaataa taccgaccat aaagaagaat tcacggcaga ttttgttctc cttaacatga    19560
aatattctct tgggtgtttt tttttaatt aaaaaaacat agactgagat tctttaatta    19620
tataatacaa aaaaggttc agccaaatca tatattgatt tttataacct tttattggca    19680
caaaacatga aactaaaacc aatatgtatt tcacaagaaa tacgacatat atgtagtacg    19740
gatgatttac ttttaatata tatatatata tatgataatt gtttattcct tatataatat    19800
tatatgtgtg ttaagagaa actttaagtc aatattatat atcatggcaa ggacatgcaa    19860
acttggagaa aattttgaac agaataatac tcaacatagt ttaaagtttg gtaaacatct    19920
```

```
actggatgtg atctaaattc tctagctttt ttttaaaact ttcttcttta ttataatatt    19980
tattataaat tcgtagttta ggtgtttagg gggtctaaag caattttctt tgggaattca    20040
cgtgatgata tacatatatt tatttaattt ttttaataca tatatataag gtctataaaa    20100
aagttagtaa attcgtccga attcatgaac ctatcttgct ttacctctga tcgcgttctc    20160
cttttctggc ctaccccac cacaaaatct ggaaactctt atctagttca cacatagatg     20220
acataaccaa gaaaagtata ttgaacactc catgtttctg aataattaat taaccttatg    20280
tattttaagt atggtaatat taatgtaata ttaattacat ttaaattaaa atgtcagtgg    20340
aagagaaagt atatgcacat tatttattaa cttcttgttt ttgggttttt atcttcctat    20400
catatattta actttgtata ccatcatgtt atctttctac tattgtattt tcaaattctc    20460
aaattccaca ttttaagaaa gtttgtaggt agatgttctt cggagactta ttaatacaat    20520
ctcgtttcaa tttgtttatc ctactaattt attaaaaga atgtatcttt tcttttctaa     20580
tagctccgca agtaaacaca taactaaaga gtattttatt ccattatcat atctttaatt    20640
taagaccgta aattttttaa actccatctc atatcaaaat aggataaaca aattaaaaca    20700
gaatgcctcg tataaaacaa tattttcatt attatagggt acaaaaccaa aactcaaatt    20760
caaatgtgta attagcatgc aatgtccttt gatcccttag ccttttttt ctagagaaca     20820
ctgaaaataa ggagtatttt tcatctaaac aaaagattcc ctatgtgggg ttaaagatttt   20880
ggattgataa agtaaaaatg gattcttctc aatcctatta ttccactaca acctcctttt    20940
tctctctttg gttcatgtaa ttagaagtat acacaaaatt ccaagaactc aaaatgttct    21000
caaacacgtg tcaattctct acttgcatga tcaataatca atatatatat atatatatac    21060
actttttact ccaataatct tatttccttt gatggtaaaa ttttataatt ttaatttttt    21120
gctttcatga acaacgtcct tataaagttg ggaaatttc atcacttata tatgcaaaca    21180
aaatgtcata ttcgtccact ttgataatag taacaagggt atattatatt ctttaagggt    21240
acaagaatat gttctcccta caatcttctc gtacattagt tgtaaaatac ccctcaaaac    21300
ttttcacttg ctacacaatt ttgatacaca cattctaaac gtaaagaatt ttcttcacta    21360
tcaacatatt taagtggtaa taattaacct taaaattatt ttctttatttt caatttatgc    21420
aatataattt gttttttcaga aattaaactt tttgattttt cttgtgtatt catacacaca   21480
aattttttgag ataaaattag tatatataga aattatgtaa aaactgctat aaattactgt   21540
aacagattat ttaaaataat acaaaatata taattaatcg tgataaaaaa atactcgttt    21600
gaatctcgaa attctaaaga tgccagaaac ggggggagact accccactat ccactttaag   21660
acctctatca aactcacaca atataattgt aagcatccaa aaccctctat ataaacccct    21720
cacaccctct tacatccaaa ccatctcatc ataaactaca aacacataca aaaaacattc    21780
tcattcaccct ttcctctaca aaaacataa caacatcttc aacaatcatg tctggagttt    21840
gggtattcaa gaatggtgtt gtccgtctag tggagaactc cgattgccac ggggcgaacg    21900
gactccgaaa agttcttgta catcttccta gtaatgaagt catcacatca tatgcagtac    21960
ttgaaaggaa actgtactct cttggatggg agaggtacta tgatgaacct gaacttcttc    22020
aataccacaa aagatcaacc gttcatctta tttctctacc aaaggatttc aacaggttca    22080
aatccatgca tatgttcgat atcgtcgtca agaatcgcaa tgaatttgag gttagagata    22140
tgtaaacaaa atatggggga aaaaggggaa ggagttgatc atttgaatgt gttttttttt    22200
ctttttttg cttttttttg gtcaagtgtg ttgtaattaa gttctatcg tttaatttgt      22260
gatttgtttc acaatgttgc taaggttgta atttggaaag ttgtaagagg ggaaatgttg    22320
```

```
tatattatta caagtgaatg tgttttatta tatgatatat atatatataa gagtgcttat    22380
tccacaaaat attttttcctt ttgcgcttaa aatctatgta cacatattta tatcattaag   22440
tcaatgaatc aaaatgtaat tatagatatc taatttagta ttgaccttt ataaatgttg    22500 aattactcta atactataaa aattaatact ctgaaactta taacctcaaa aacttttcg    22560 tagcttgttt taagaagaaa caaaatgacg aagatatttc tttcttctta ttcgactta   22620 atgacttcga aagtgcacgc atcccaagaa ggctcatcct ttttcaaaaa taaaaaaata   22680
aaaaaaacaa gaattccta tatctccttt tagtactaca ccttattata ttatgacggt   22740
tattatttgt atttcaattt atgtgacaca ttttatttt ttagtgttat atagtttaaa   22800
tttaattgag aatttggaaa gaagctcatc cccattattt tttctctcca tttccccgag   22860
tttccacttg gatggaagcc atgtgtcgta actaaaaatt aaggcgggag atttgaaata   22920
acaaatatta tttttcaaat ctccaccctt aattttaat tatgacacat ggcttccatc    22980
caagtgggaa ctgtagtaaa aatgtaatgg agaggagcct cttccaagaa tttgtgcatg   23040 aaatttcaa tttttttta aagaatatat atatttgtaa actatataa aaatattata    23100 agtcacacta attgacaatt caaaatattt aaaagacatg aaaaaattac gataaaaat    23160 agatttattt aaatttcaaa atttaaattg tatcacataa actgagacat atattatact   23220
aatttttttg ctcagaactt tacttaaaac ttaaaagacg attatgtaca caatttatct   23280
tagctcgaat agtattaaaa ttagataata actttaccga aaacaaaaac gaaaagcta   23340 ggaaagatta ttgatattac tttgagcaat tctttcttaa atactgaata atatttcact   23400
tgattttaat atgttagtga aattatttgc gcttcgcgcg actatataaa atatttataa   23460
gataataata tgtaatattt aggttagtat taaatatata aaaatataa atatttctcc    23520 tcgtctgcaa tattataggt ttctttaaa acatataaaa tatattatta attttgtata   23580
tgtatatttt agaataaaatt atttagcgtg gtgaagtaaa tgaaataaga gatatatgtt   23640
gaaataacaa tatattatat taggttgcaa atatttata tgtctaattt tctctatctt    23700
ttgtaggata actaatttc tattcaaatt ttgatttcgt caaaacaaaa ttaattttt    23760 taactttat tttacattt gcttattata attatttaaa cattaattaa atatttataa    23820
gactaacgaa aaatgaaata taaaagttaa aaatgaaaca tttcttacct tcatgtactt   23880 cttttttgt tacaaaccaa tactgtatga tgagaagaga aatgataatt gtgaatgtga   23940
atcttcatga aactaatatg aatttatagg caaaataaag gaataccata aggcatcata   24000
aacttacaaa tttaatttgg aagttatgga cacaaaaatt atgagagtta tgaatatta    24060 aaagtaaaaa ttaaagaggg gcaagtcatc atgagtagta actcctagta aataaattaa   24120
aaaataaaaa taaaaatact taaaatataa aaaaagtttt attatgattt catggttaga   24180
agtgagataa acaaataaaa gaataatata gggagttttt tttaataaat atttctacat   24240
taataaaata tttatttgta taaaaaacca tcaggttttt cgaatgcgaa tttggagtaa   24300
aaagcaggac aatttaacta catgcaatcc gatctgaaat aagtcaggca attatactac   24360
ggccactcca taaatttgtc atggatcact tttcggggtg caaaaggatt cgtagatcat   24420
atatatcacc tgtatatcat gtatatcagc tgtatataaa agaaattcag atttttaaaac  24480 acacattttg agtttcttgt aatacttttc acccttttatt gaccccaaca acccttaaaa   24540
gctctcttca atcctcccaa gtcttagtaa gtatccccca tgaattaca acttaaaagt    24600 caatattcat acgattcttt tagataaagt ctctattatt tcagtatcag atttttaata   24660
```

```
ttcatgagtt tgtttggaaa aatattatgt atttcaaaaa attattttat atcctattat  24720
atttggaaga ggttattact atgtcttaaa tattttccct ccataaataa tccttgattg  24780
acaattactc ctaatccaaa tataacatta gtttcatcca tttattcatt cttgaatgag  24840
taactaatga gaatactgtt tcttttaacc aaaataaatg gtcttcaaat cttttgccct  24900
tattggctca ttattggcat taattctttt tttaaccgtt ggagccttta ggcttatata  24960
tactttcata taaagtgttc ttcctctatc acaatgtgtg aaaaaaaata tacatttga   25020
gtttataaat ctttccttct atattttatt ggtgtgttgg atttcgtttt taaaaatctt  25080
tgtcaatttc tggctctagt agaagacctt gctgaatcct gggagatatc catatcgggt  25140
gaaatatcct taaggatatt gtctctcgac acgcctcaag ctttgagaag ttcttacaaa  25200
aatttgtggt aaagtataag atttgataaa ttcagtacaa gtattcgtca aaagatatt   25260
ttaggtaaaa tttacaactt tgaataatc agtatgatca atatcgtcaa attattagta   25320
taaccagtca gtcaaacatt ttttttattg ggagtattcc ttatcatcaa gcgggtctat  25380
agggatgaag gttcacccat cagcttagga ttgagacatc taatagaaat tcctaaaact  25440
attagaacta cgtgccaccg ttggaaatca gcttagtggt aatacctcat tagctcaaat  25500
tagggtttat accccaata aggtctattg agattttttt gatggggatt ataggttaaa   25560
attcatattt agttcacatg gttatatgtt ggttattagt attgtctcat atattgcttg  25620
accttgttaa tcacactaac tgtccgtttg accatgcgat atagtatcat gatatggaat  25680
catgagatga aattgctgtt ttgtttggac ataatgtgat atgaaatttt ggtgttctat  25740
attcataaat ataaaactcc ataagttcta aaactattaa aataaccca attatttatt   25800
caatattatc aaataaacaa aaaatcataa aatcgtatag taaattattg taaagttatt  25860
ttttctccac ttaagtaatt tgtaattgtt tcatcaatat atttgagtaa aaataaaaca  25920
cctttcacat gctcttcaag atttattac tcaacaatcg tgaagtgtga gttaaagtga   25980
ttatatgttg gttagaataa taattttttt taaaaataat tatgtgatca taattttgt   26040
ttacatgtga aacaaatggt tagtagatat aaatgtgggg ttgtttaac aaaatataaa   26100
tctgtgaatc aatttttcta ttaaaataat tcaaatcatg atatagtatt cccacatgat  26160
acaatatcat tgttttttgga gaatatgata tcacatctca tgatataccca tatcatgaga  26220
tgaaatcagc gtaaaatcac atatccaaat gttggtatca catgaccaaa cacctaataa  26280
atatatgtat atgacatttc agatatattc tgagatgaat atacgtaaaa acagaggcga  26340
gcgaaaaagg gagagagaca aacaagatag gaaaaagaca agcaataaag gaagagacac  26400
caacaagatt cgattttgaa gagccctaac ccctacctaa taaactcaaa ggtaaaatgt  26460
tggcggattg tgaactgggc taggcaacca accccttgta tagaacccgg cctaaaattg  26520
gtgtcgttag gctcaaaccg aactagccag ctaggggtat catcaaattt gaagaatcga  26580
gaaactattg tgcaaatttt ttaccaaatt aaatcattat ataaaaaat ttatcaaat    26640
aatatatttt tctaaaattt tacaaaacta gtataacgtt ttttacagta acgttttagg  26700
tatatttac ttttaaaag ctaacagtgt cagattgata tacgttactg taagtaacgt    26760
tttactccta aaacattatt ttgagtaacg ttttactcct aaaacattac tatgagtaac  26820
gtatatcaat ctaacgctgt cagctttaa aaaataagat atatcctaaa atgtcactgt   26880
gaaataagtt tataataatt ttataaaatt ttatgaaaaa acatcttatt ttgatgaatt  26940
gctttatata atgacttaat ttggttaaaa ctaattaatg cataccaatc tttgacaaaa  27000
gtgcaattgg tcaattggga gcccttaca tgtgctcata agagccttat caacacgtgc   27060
```

```
accatgaaaa agcgaaggca actacaactt ggctaatctc ctttgctctt cgacataaag    27120
gctttgactc tatgactatg attcaataat ttaatatatt ggttctgaat ttaatccata    27180
cattataagt cgagccaaaa ctttaacttg aagaatttca ataagtaaat ttcactacta    27240
tttaatacat gattttgact aaagctgaaa ggttatgagg aactcataat tttctttcta    27300
gctcggttct tgaattacaa tgaattatat aatttattga taaattaact ttatttcttt    27360
ctataagtta attagtaggt gagaaggaaa gagtaatgct ttccacacta atcttgtgag    27420
tttaaacctc actattaata aaagtttctc gttttcctta aaaagaaagc atattttgtg    27480
ttatttttt cttctgttct aaaatttaaa atcgtcaaac tcttaattct gcatctgcct     27540
ctatagccta ttaaaatccc tttgaatcat gtaactatgc cacttggggt gtgggttgac    27600
aaagggatca ataaactcat agtgatcatg aaaaagtgt gtgtaaaaag agtagtaaca     27660
attaagttat ttgatattct tgtcagtaaa ggccattcct caaatgaatg gcatatagt     27720
gtgtgacttc ttctttgtac actgaaattg tgatatggga atgggagggg aaagtgaaag    27780
agacagaaga gaaggaagat tgattttact tttcactcat taaatcctat tcctatccaa    27840
tccaatatcc acaaaaaagt atgggacatg agagatctcc atttctatca cttttaatta    27900
tttccttcat ttttatctat tcctattcct ttttgtttca tgttatatat cttctatttt    27960
tagaaagtta ttatatattt agaaacattc tttaatcact ttaataaacc ctttaatttt    28020
gtcatgttat gatagtaact agactacatt attattttgg ttccttacgt aatgaaagaa    28080
aactatattt ctagatcaat tccaacgctt tcctataagc ctaaagtgat tataattgaa    28140
gccataatga aattattcat gctaaataat actacctgat ccctttaat ttctctgtct    28200
tgtcttgaaa aaagaatgtt tttttttttt tataattctt tactttcaat tctttacat     28260
gtgatcttta gaagacaaga ttaaataaca ttttgatact ttctatatat tttaattata    28320
aaatcacaag attcagaagt cttgtttatt ttttaaaact tcatgtcaaa ctaaaactag    28380
ataaacaaat tggaacagac actatcccat tgaaattttc ctattgaaaa atgtccagtg    28440
gctatactca cactaatgtt taaattacac aacaaaatta aaaaaaaaaa ctcttggtat    28500
tttagtgaga atttgtttct caccatacgt ttttattgac ctagttaaat aggaaatggg    28560
tgggaatatc acgtatcata acacaaattt ctcattgatt tggagtaatt tttttttaa     28620
aaaaaattgt tattagacat taattaagga ttaaaagaaa catcatcaac atgagatggg    28680
acaaattaat cttccccgaa atatctttta atttatttaa ttcttccttt ttgtgaaggg    28740
ctgatcaagc aatggatata agaatagaag attgttctta gcactaaaaa aattaaagaa    28800
ttatgcttgg aacccattaa ccaaaagaat taggttcatc ttatgagcat aagatcatta    28860
attagtgatt gtttaggaga agattctaat ttcagtaggg caaattaggg catcttgtgg    28920
ccatttaaat attctcccct tctttttctt taatcttaat aaacgtacga taagttagta    28980
tatttctaaa tcctataagc agccacattc caaaatccta cctattatca attttattaa    29040
ataagaaaaa agattacttt ttgccacctt atgtattttt ttattacaca ctacatagaa    29100
accctataa aaacccactc acacttatgt tcaaa                                 29135
```

<210> SEQ ID NO 65
<211> LENGTH: 74
<212> TYPE: DNA
<213> ORGANISM: Solanum lycopersicum

<400> SEQUENCE: 65

```
tgtccgtcta gtggagaact ccgattgcca cggggcgaac ggactccgaa aagttcttgt      60
acatcttcta gtaa                                                       74

<210> SEQ ID NO 66
<211> LENGTH: 67
<212> TYPE: DNA
<213> ORGANISM: Artificial Sequence
<220> FEATURE:
<223> OTHER INFORMATION: Synthetic sequence

<400> SEQUENCE: 66
tgtccgtcta actccgattg ccacggggcg aacggactcc gaaaagttct tgtacatctt     60
ctagtaa                                                               67

<210> SEQ ID NO 67
<211> LENGTH: 72
<212> TYPE: DNA
<213> ORGANISM: Artificial Sequence
<220> FEATURE:
<223> OTHER INFORMATION: Synthetic sequence

<400> SEQUENCE: 67
tgtccgtcta gtggagaact ccgattgcca cggggcgaac ggactccgaa aatcttgtac     60
atcttctagt aa                                                         72
```

COMPOSITIONS AND METHODS FOR IDENTIFYING AND SELECTING BRACHYTIC LOCUS IN SOLANACEAE

CROSS-REFERENCE TO RELATED APPLICATIONS

This application claims priority to U.S. Provisional Application Ser. No. 62/672,092, filed May 16, 2018, which is incorporated herein by reference.

GOVERNMENT LICENSE RIGHTS

The work upon which this application is based was funded, in whole or in part through a subrecipient grant 024065 awarded by the United States Department of Agriculture through the Florida Department of Agriculture and Consumer Services.

This invention was made with support through a Sponsored Research Agreement with the Florida Tomato Committee.

REFERENCE TO A SEQUENCE LISTING SUBMITTED AS A TEXT FILE VIA EFS WEB

The Sequence Listing written in file 528212_T17247_SeqListing_ST25.txt is 60 kilobytes in size, was created on May 6, 2019, and is hereby incorporated by reference.

BACKGROUND

Tomato is the most valuable horticultural crop worldwide (Food and Agriculture Organization of the United Nations). Fresh-market and processing tomatoes are the two most commonly consumed types of tomatoes and account for more than $2.6 billion in annual farm cash receipts in the United States alone (United States Department of Agriculture Economic Research Service (USDA ERS)). Unlike processing tomatoes, which have been successfully adapted for farm machinery for nearly all aspects of production, field production of fresh-market tomatoes continues to heavily rely on manual labor (Davis and Estes, 1993 USDA ERS; Van Sickle and McAvoy 2015 USDA ERS).

Most field-grown fresh-market tomato varieties have determinate vines with upright growth. Because of their heavy large fruits (typical 250-110 g for fresh-market fruits versus <80 g for processing fruits) and the higher quality requirement of exterior standards, displacement of those plants, especially fruits laying on the soil, significantly reduces yield and quality by damages from human activities, machineries and soilborne pathogens (Adelana, B. O. 1980. Relationship between lodging, morphological characters and yield of tomato cultivars. Scientia Hort. 13:143-148). Manual practices such as staking and tying are required to sustain the current production of marketable fresh-market tomatoes.

Current compact growth habit (CGH) tomato plants, while being determinate, and having shortened internodes, a spreading characteristic (with increased side branching), and a concentrated fruit setting (producing fruits over a narrow time interval) suffer from insufficient fruit size. There presently are no commercial large-fruited, fresh-market tomatoes that show CGH. Development of fresh market tomato lines that hold fruits off the ground without the support of stakes throughout a season, adapt to high plant density per the unit area, and produce high quality fresh-market fruit of economically viable size would be of significant benefit to the tomato industry. Further, such tomato lines may also enable machine harvesting, reducing the dependence on farm labor.

Introduction of the brachytic trait into normal phenotype tomatoes resulted in tomatoes with shortened internodes (MacArthur, J. W. 1931. Linkage studies with the tomato. III Fifteen factors in six groups. Roy. Canad. Inst. Trans. 18:1-19, shortened internode length by approximately 50%, Barton, D. W, L. Butler, J. A. Jenkins, C. M, Rick, and P. A. Young. 1955. Rules for nomenclature in tomato genetics (includes a list of known genes). J. Hered. 46:22-76; Balint-Kurti, P. J., D. A. Jones, and J. D. Jones. 1995. Integration of the classical and RFLP linkage maps of the short arm of tomato chromosome 1. Theor. Appl. Genet. 90:17-26.). Since the introduction of br into fresh-market tomato breeding programs in 1980s, the locus has been shown to be the primary source of the shortened internode phenotype (Tigchelaar, E. C. 1986. Tomato Breeding. In Breeding Vegetable Crops. M. J. Bassett (Editor), pp. 135-171. AVI Publishing Co., Westport, Conn. Scott, J. W., S. F. Hutton, and J. Strobel. 2010. Some highlights from the University of Florida tomato breeding program. Proc. Florida Tomato Inst. 53:9-10 . . . ; Frasca, A. C, M. Ozores-Hampton, J. Scott, and E. McAvoy. 2014. Effect of plant population and breeding lines on fresh-market, compact growth habit tomatoes growth, flowering pattern, yield, and postharvest quality. HortScience 49:1529-1536). It is notable that no evidence for a significant negative correlation observed between marketable fruit harvests and the br has been reported in a peer-reviewed forum (Gardner, R. G. and J. M. Davis. 1991. Evaluation of a fresh-market tomato breeding line with brachytic and prostrate growth habits. HortScience 26:713. (Abstr.); Frasca, A. C, M. Ozores-Hampton, J. Scott, and E. McAvoy. 2014. Effect of plant population and breeding lines on fresh-market, compact growth habit tomatoes growth, flowering pattern, yield, and postharvest quality. HortScience 49:1529-1536. The br locus was mapped onto tomato chromosome 1 through classical genetic experiments (MacArthur, J. W. 1931. Linkage studies with the tomato. III Fifteen factors in six groups. Roy. Canad. Inst. Trans. 18:1-19; Balint-Kurti, P. J., D. A. Jones, and J. D. Jones. 1995. Integration of the classical and RFLP linkage maps of the short arm of tomato chromosome 1. Theor. Appl. Genet. 90:17-26.), but the molecular basis of this locus has remained unclear. The presence of br is an important consideration in developing tomatoes intended for mechanical harvest. There is a need to breed new genes that optimize phenotypes for such mechanization into fresh-market adapted tomato cultivars. To better utilize the brachytic trait, the tomato breeding community needs genetic markers linked to the gene to improve selection efficiency.

SUMMARY

Described are markers and methods for marker-assisted selection (MAS) of the br locus and for cloning the br gene. Use of MAS in br breeding programs will facilitate incorporation of the locus into diverse genetic backgrounds.

Described is a locus responsible for the brachytic phenotype in plants of the family Solanaceae (brachytic locus). The brachytic locus maps to a 763.1-kb interval between 74,936,467 and 75,699,595 bp on chromosome 1. Solanaceae plants homozygous for the br allele of the brachytic locus have shortened internode length. Solanaceae plants heterozygous for the br allele (one br allele and one normal allele) of the brachytic locus have intermediate internode length.

Brachytic markers useful for genotyping (mapping, tracking, identifying, analyzing) a brachytic locus in a Solanaceae plant are described. In some embodiments, a brachytic marker comprises a detectable genetic marker linked, closely linked, tightly linked, or extremely tightly to a brachytic locus. In some embodiments, a brachytic marker comprises a detectable genetic marker linked, closely linked, tightly linked, or extremely tightly linked to a genomic sequence encompassed by 74,936,467 and 75,699,595 bp on chromosome 1 of a tomato plant. In some embodiments, a brachytic marker is a detectable genetic marker linked, closely linked, tightly linked, or extremely tightly linked to one or more of: SEQ ID NO: 1 (br gene sequence) or a portion thereof, SEQ ID NO: 2 (normal gene sequence) or a portion thereof, SEQ ID NO: 3 (homolog) or a portion thereof, SEQ ID NO: 4 (homolog) or a portion thereof, SEQ ID NO: 5 or portion thereof, SEQ ID NO: 6 or a portion thereof, SEQ ID NO: 7 or a portion thereof, SEQ ID NO: 8 or a portion thereof and/or SEQ ID NO:48 or a portion thereof. In some embodiments, a brachytic marker is a detectable genetic marker linked, closely linked, tightly linked, or extremely tightly linked to a homolog or an ortholog of any of: SEQ ID NO: 1 or a portion thereof, SEQ ID NO: 2 or a portion thereof, SEQ ID NO: 3 or a portion thereof, SEQ ID NO: 4 or a portion thereof, SEQ ID NO: 5 or portion thereof, SEQ ID NO: 6 or a portion thereof, SEQ ID NO: 7 or a portion thereof, SEQ ID NO: 8 or a portion thereof and/or SEQ ID NO:48 or a portion thereof.

In some embodiments, a brachytic marker includes, but is not limited to, a single nucleotide polymorphism (SNPs) or an indel (insertions and deletions). Exemplary SNPs include, but are not limited to brM1, brM2, brM3, brM4, brM5, brM6, brM7, brM8, solcap_18634, solcap_456, and solcap_457. In some embodiments, the brachytic marker comprises a nucleotide sequence comprising SEQ ID NO: 1 or a portion thereof, SEQ ID NO: 2 or a portion thereof, SEQ ID NO: 3 or a portion thereof, SEQ ID NO: 4 or a portion thereof, SEQ ID NO: 5 or portion thereof, SEQ ID NO: 6 or a portion thereof, SEQ ID NO: 7 or a portion thereof, SEQ ID NO: 8 or a portion thereof and/or SEQ ID NO:48 or a portion thereof. In some embodiments, the brachytic marker comprises a nucleotide sequence comprising a sequence that is a homolog or an ortholog of any of: SEQ ID NO: 1 or a portion thereof, SEQ ID NO: 2 or a portion thereof, SEQ ID NO: 3 or a portion thereof, SEQ ID NO: 4 or a portion thereof, SEQ ID NO: 5 or portion thereof, SEQ ID NO: 6 or a portion thereof, SEQ ID NO: 7 or a portion thereof, SEQ ID NO: 8 or a portion thereof and/or SEQ ID NO:48 or a portion thereof.

With the described brachytic markers, brachytic plants can be rapidly and efficiently identified. The identification of the brachytic locus can be used to aid in introgressing the brachytic trait into tomato plants. The resultant plants have shortened internodes. The shortened internodes lead to shorter plants that do not require staking. Further, unlike current tomato plants that do not require staking, introgressed brachytic tomato plants retain marketable fruit size, number, and quality. Shorter plants that do not require staking and retain marketable fruit size, number, and quality provide a suitable plant habit for once over machine harvest. In some embodiments, the brachytic plants exhibit accelerated or early flowering.

Isolated sequences encoding a Solanaceae br allele are described. In some embodiments, a br allele sequence comprises all or a portion of SEQ ID NO: 1. In some embodiments, a br allele sequence comprises all or a portion of SEQ ID NO: 48. In some embodiments, a br allele sequence comprises all or a portion of a modified SEQ ID NO: 2, wherein the modification comprises a deletion, missense mutation, nonsense mutation, or insertion. In some embodiments, the br allele sequence comprises all or a portion of a modified SEQ ID NO: 3 or SEQ ID NO: 4, wherein the modification comprises a deletion, missense mutation, nonsense mutation, or insertion.

In some embodiments the isolated sequences encoding a Solanaceae br allele are used to generate transgenic plants carrying a br allele. The transgenic plants can then be used to produce progeny brachytic plants. Any of the described br allele sequences or homologs or orthologs thereof, can be inserted into a plant using methods known in the art. Plants are then selected, using the described brachytic markers for plants in which the normal brachytic allele is disrupted or replaced by the inserted sequence.

Methods of using the described locus sequences and/or brachytic markers to produce brachytic Solanaceae plants and/or introgress a brachytic trait from donor Solanaceae plants to recipient plants Solanaceae are described. A Solanaceae plant can be a S. *Solanum* or a *Capsicum* plant. A *Solanum* plant can be a *S. melongena* (eggplant) plant, *S. tuberosum* (potato) plant, or a *S. lycopersicum* (tomato) plant. A *Capsicum* plant can be a *C. annuum* (pepper) plant or a *C. frutescens* (tabasco pepper) plant. The term tomato includes but is not limited to any species of tomato.

In some embodiments, the described brachytic markers may be used in marker-assisted selection to transfer (introgress) segment(s) of DNA that contain one or more determinants of brachytic. In particular embodiments, the brachytic markers may be selected from a group of markers comprising the markers listed in Tables 3-6 or SEQ ID NOs: 1-8 and 48 and markers that are their equivalents. In some embodiments, a marker may be selected from the group comprising, or consisting of: brM1, brM2, brM3, brM4, brM5, brM6, brM7, brM8, solcap_18634, solcap_456, solcap_457, SEQ ID NO: 1 or a portion thereof, SEQ ID NO: 48 or a portion thereof, SEQ ID NO: 2 or a portion thereof, an ortholog of SEQ ID NO: 1 or a portion thereof, an ortholog of SEQ ID NO: 48 or a portion thereof, and an ortholog of SEQ ID NO: 2 or a portion thereof.

In some embodiments, methods for using brachytic markers linked to a brachytic locus in Solanaceae to transfer or introgress a segment of DNA that contain one or more determinants of the brachytic (e.g. a br allele) comprise analyzing a genomic DNA of a donor brachytic parent having a brachytic genotype and a recipient parent having a recipient genotype with probes that are specifically hybridizable to brachytic markers; sexually crossing the two parental plant genotypes to obtain a progeny population, and analyzing those progeny for the presence or absence of the brachytic markers; backcrossing the progeny that contain the brachytic markers to a recipient plant having the recipient genotype to produce a first backcross population, and then continuing with a backcrossing program until a final progeny is obtained that comprises any desired trait(s) exhibited by the recipient genotype and the brachytic phenotype. In particular embodiments, individual progeny obtained in each crossing and backcrossing step are selected by brachytic marker analysis at each generation.

Plants made by introgressing the brachytic locus of a parent brachytic plant have shortened internodes. In some embodiments, the brachytic plants do not require staking. In some embodiments, the brachytic plants have accelerated or early flowering. Progeny plants made by introgressing the brachytic locus of a parent brachytic plant maintain fruit size and fruit weight. In some embodiments, tomato plants exhibiting a brachytic phenotype and once-over machine-harvestable marketable fruit are described. In other embodiments, methods of producing tomato plants exhibiting a brachytic phenotype and once-over machine-harvestable marketable fruit are described. In other embodiments, methods of producing tomato plants exhibiting accelerated or early flowering phenotype fruit are described. The process comprises introgressing, using marker assisted selection, a brachytic locus from a brachytic tomato into recipient tomato line having desired fruit characteristics.

In some embodiments, methods of producing brachytic plants and methods of genetically modifying a plant to produce a brachytic plant using a Clustered Regularly Interspaced Short Palindromic Repeats (CRISPR)/CRISPR-associated (Cas) system are described. In some embodiments, brachytic plants created using a CRISPR system are described. In some embodiments, nucleic acids for producing a brachytic plant using a CRISPR system are described.

BRIEF DESCRIPTION OF THE DRAWINGS

FIG. 3. Multiple sequence alignment between the genomic DNA sequence of Solyc01g066970.2ch01_75101399 (SEQ ID NO: 4, Solyc01g066950.1ch01_75049083 (SEQ ID NO: 3), Solyc01g066980.2ch01_75108781 (SEQ ID NO: 2) obtained from Heinz 1706 reference genome (non-brachytic plant) and the sequence from the br locus Solyc01g066980_brachytic (SEQ ID NO: 1).

DETAILED DESCRIPTION

I. Definitions

Figure 1:
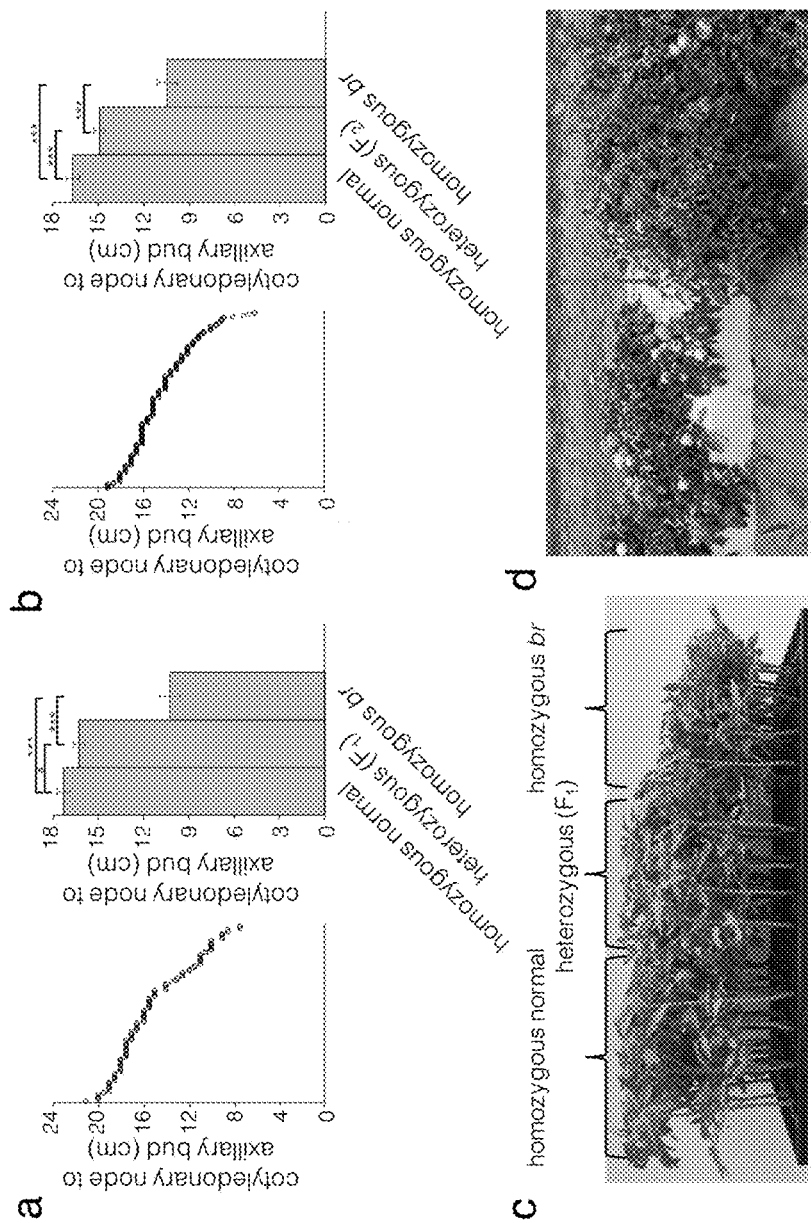
FIG. 1. Decreased plant height mediated by the br. a) A distribution of heights in two homozygous parents (with or without the br) and $F_1$ progeny between those (left). Selfed homozygous parental lines were harvested from each line in bulk. $F_1$ plants heterozygous for br reached a height intermediate to the homozygous normal parent or homozygous br (right). n=40, 32, 27, from the left bar to the right. Homozygous normal and homozygous br represent homozygous for the normal allele and homozygous for the br, respectively. Statistical significance is indicated by ***P<0.001 using a one-way ANOVA followed by a two-tailed Tukey multiple comparison test (figures a and b) and #P<0.05 for a comparison between individuals homozygous normal and heterozygous by a two-tailed t-test (figure a). b) A distribution of heights in a $F_2$ segregating population (left). There were statistical significant differences in heights between genotypes (right). n=32, 84, 34, from the left to the right. c) Picture showing $F_1$ and homozygous parents used in FIG. 1a. d) Example picture showing the phenotype in mature plants with the br (left) and without the br (right) in the field. Plants were grown without the support of staking or tying throughout a season FIG. 2. Diagram of the region of the fine mapping interval of a tomato line with brachytic that shows sequence polymorphism in a Flowering Promoting Factor 1 gene (Solyc01g066980; SL3.0 version of Heinz 1706 reference genome assembly).

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (Ausbel et al., eds., John Wiley & Sons, Inc. 2001; Transgenic Plants: Methods and Protocols (Leandro Pena, ed., Humana Press, 1st edition, 2004); and, *Agrobacterium* Protocols (Wan, ed., Humana Press, 2nd edition, 2006). As appropriate, procedures involving the use of commercially available kits and reagents are generally carried out in accordance with manufacturer defined protocols and/or parameters unless otherwise noted.

The term "nucleic acid" refers to deoxyribonucleotides or ribonucleotides and polymers thereof ("poll/nucleotides") in either single- or double-stranded form. Unless specifically limited, the term "polynucleotide" encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a sequence comparison algorithms, or by manual alignment and visual inspection.

The term "plant" includes whole plants, plant organs (e.g., leaves, stems, flowers, roots, reproductive organs, embryos and parts thereof, etc.), seedlings, seeds and plant cells and progeny thereof. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A "brachytic plant" is characterized by having shortened internodes without a corresponding reduction in the number of internodes or the number and size of other plant parts. Shortened internodes drive shortened stem length/plant height based compared to normal plants. Brachytic and shortened internodes are distinguishable from a dwarf-mediated phenotype in which all parts are shortened. In some embodiments, the brachytic plants also have accelerated or early flowering.

"Early flowering" refers to increasing the ability of the plant to exhibit an early flowering as compared to a matching control plant (e.g., a similar plant not having the brachytic phenotype). In some embodiments, early flowering indicated a shorter time period between germination to the time in which the first flower opens. In some embodiments, increasing early flowering of a population of plants increases the number or percentage of plants having an early flowering. In some embodiments, early flowering enables the plant to produce more flowers, fruits, pods and seeds without changing plant maturity period. Early flowering can also lead to increased yield by providing a longer grain filling or fruit maturation period.

The term "locus" refers to a position on the genome that corresponds to a measurable characteristic (e.g., a trait) or gene. A locus can be a genomic region or section of DNA (the locus) which correlates with a variation in a phenotype. Loci are mapped by identifying which genetic markers (such as SNPs or AFLPs) correlate with (are linked with) an observed trait or gene. A locus can comprise a single or multiple genes or other genetic information within a contiguous genomic region or linkage group. A "brachytic locus" comprises a locus that corresponds to the brachytic measurable trait. A "br locus" or "br allele" comprises a brachytic locus that confers the brachytic trait. Plants homozygous for the br locus or br allele exhibit the brachytic phenotype. Plants homozygous for the normal brachytic locus exhibit normal growth with respect to the brachytic phenotype. Plants heterozygous at the brachytic locus, carrying one normal brachytic locus and one br locus, exhibit intermediate growth characteristics with respect to the brachytic phenotype.

A "marker" or "genetic marker" refers to a gene or nucleotide sequence that can be used to identify the presence or location of a trait determinant, locus, gene, and/or allele. A genetic marker may be described as a variation at a given genomic locus. A genetic marker may be a short DNA sequence, such as a sequence surrounding a single base-pair change (for example as in a single nucleotide polymorphism (SNP)), or a longer DNA sequence, for example, a microsatellite/simple sequence repeat (SSR)). A "marker allele" refers to the version of the marker that is present in a particular individual. A genetic marker can be used to identify individuals, genes, or loci in an off-spring originating from an individual parent. A "brachytic marker" is a genetic marker that is linked, closely linked, tightly linked, or extremely tightly linked to the brachytic locus.

The term "chromosomal interval" or "chromosomal segment" refers to a contiguous linear span of genomic DNA that resides in planta on a single chromosome, usually defined with reference to two markers defining the end points of the chromosomal interval. The specified interval may include the markers at the end points (e.g. one or more markers on or within the chromosomal interval defined by marker A and marker B) or may exclude the markers at the end points of the interval (e.g. one or more markers within the chromosomal interval defined by marker A and marker B). A "recombination event" refers to the occurrence of recombination between homologous chromosomes, and refers to a specific chromosomal location where such a recombination has occurred (e.g. a recombination of a chromosomal interval internal to the end points of the chromosome will have a recombination event at each end of the chromosomal interval). The genetic markers, elements, or genes located on a single chromosomal interval are physically linked.

On a genetic map, linkage of one genetic marker to a gene or another genetic marker can be measured as a recombination frequency. In general, the closer two loci are on the genetic map, the closer they lie to each other on the physical map. A relative genetic distance (determined by crossing over frequencies, measured in centimorgans; cM) can be proportional to the physical distance (measured in base pairs, e.g., kilobase pairs (kb) or mega-base pairs (Mbp)) that two linked loci are separated from each other on a chromosome. A lack of precise proportionality between cM and physical distance can result from variation in recombination frequencies for different chromosomal regions, e.g., some chromosomal regions are recombination "hot spots," while others regions do not show any recombination, or only demonstrate rare recombination events. In general, the closer one marker is to another marker, whether measured in terms of recombination or physical distance, the more strongly they are linked. The closer a molecular marker is to a gene that encodes a polypeptide that imparts a particular phenotype (disease resistance), whether measured in terms of recombination or physical distance, the better that marker serves to tag the desired phenotypic trait.

Linkage between genes or markers indicates a likelihood of the genes or markers being passed on together to individuals in the next generation. The closer two genes or markers are to each other, the closer to one (1) this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the term "linked" may refer to a relationship between a marker and a gene, or between a marker and a phenotype.

"Linked" refers to one or more genes or markers that are located within about 65 megabases (Mb) of one another on the same chromosome. Thus, two "linked" genes or markers may be separated, for example, by about 65 Mb, about 60 Mb, about 55 Mb, about 50 Mb, about 45 Mb, about 40 Mb, about 35 Mb, about 30 Mb, about 25 Mb, about 20 Mb, about 15 Mb, about 10 Mb, about 9.0. Mb, about 8.0 Mb, about 7.0 Mb, about 6.0 Mb, about 5.2 Mb, about 4.0 Mb, about 3.0 Mb, about 2.0 Mb, about 1.0 Mb, or fewer Mb.

"Closely linked" refers to one or more genes or markers that are located within about 2.0 Mb of one another on the same chromosome. Thus, two closely linked genes or markers may be separated, for example, by about 2.00 Mb, about 1.95 Mb, about 1.90 Mb, about 1.85 Mb, about 1.80 Mb, about 1.75 Mb, about 1.70 Mb, about 1.65 Mb, about 1.60 Mb, about 1.55 Mb, about 1.50 Mb, about 1.45 Mb, about 1.40 Mb, about 1.35 Mb, about 1.30 Mb, about 1.25 Mb, about 1.20 Mb, about 1.15 Mb, about 1.10 Mb, about 1.05 Mb, about 1.00 Mb, about 0.95 Mb, about 0.90 Mb, about 0.85 Mb, about 0.80 Mb, about 0.75 Mb, about 0.70 Mb, about 0.65 Mb, about 0.60 Mb, about 0.55 Mb, about 0.50 Mb, about 0.45 Mb, about 0.40 Mb, about 0.35 Mb, about 0.30 Mb, about 0.25 Mb, about 0.20 Mb, about 0.15 Mb, about 0.10 Mb, about 0.05 Mb, about 0.025 Mb, or about 0.01 Mb "Tightly linked" refers to one or more genes or markers that are located within about 1.0 Mb of one another on the same chromosome. Thus, two tightly linked genes or markers may be separated, for example, by about 1.00 Mb, about 0.95 Mb, about 0.90 Mb, about 0.85 Mb, about 0.80 Mb, about 0.75 Mb, about 0.70 Mb, about 0.65 Mb, about 0.60 Mb, about 0.55 Mb about 0.5 Mb, about 0.45 Mb, about 0.4 Mb, about 0.35 Mb, about 0.3 Mb, about 0.25 Mb, about 0.2 Mb, about 0.15 Mb, about 0.1 Mb, or about 0.05 Mb.

"Extremely tightly linked" refers to one or more genes or markers that are located within about 100 kb of one another on the same chromosome. Thus, two extremely tightly linked genes or markers may be separated, for example, by about 100 kb, about 95 kb, about 90 kb, about 85 kb, about 80 kb, about 75 kb, about 70 kb, about 65 kb, about 60 kb, about 55 kb, about 50 kb, about 45 kb, about 40 kb, about 35 kb, about 30 kb, about 25 kb, about 20 kb, about 15 kb, about 10 kb, about 5 kb, or about 1 kb.

"Introgression" or "introgressing" of a brachytic locus means introduction of a brachytic locus from a donor plant comprising the brachytic locus into a recipient plant by standard breeding techniques, wherein selection can be done phenotypically by means of observation of the internodal length or plant height, or selection can be done with the use of brachytic markers through marker-assisted breeding, or combinations of these. The process of introgressing is often referred to as "backcrossing" when the process is repeated two or more times. In introgressing or backcrossing, the "donor" parent refers to the parental plant with the desired gene or locus to be introgressed. The "recipient" parent (used one or more times) or "recurrent" parent (used two or more times) refers to the parental plant into which the gene or locus is being introgressed. Selection is started in the F1 or any further generation from a cross between the recipient plant and the donor plant, suitably by using markers as identified herein. The skilled person is however familiar with creating and using new molecular markers that can identify or are linked to the brachytic locus.

A "homolog" or "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologs (orthologous sequences) and paralogs (paralogous sequences). Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

Compositions or methods "comprising" or "including" one or more recited elements may include other elements not specifically recited. For example, a composition that "comprises" or "includes" a marker may contain the marker alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a marker" or "at least one marker" can include a plurality of markers, including mixtures thereof.

Statistically significant means $p<0.05$ unless otherwise indicated.

II. Overview

Described are compositions, including brachytic markers, for genotyping and selecting brachytic loci, and methods for producing, breeding, identifying, and selecting brachytic plants and/or early flowering plants or plants carrying a br allele. In some embodiments, the plant is a Solanaceae plant. A Solanaceae plant can be, but is not limited to, a *Solanum* or a *Capsicum* plant. A *Solanum* plant can be, but is not limited to, a *S. melongena* (eggplant) plant, *S. tuberosum*

(potato) plant, or a *S. lycopersicum* (tomato) plant. A *Capsicum* plant can be, but is not limited to, a *C. annuum* (pepper) plant or a *C. frutescens* (tabasco pepper) plant. The term tomato includes but is not limited to, any species of tomato.

Described herein are is a brachytic locus and genetic markers linked to the brachytic locus (brachytic markers). In some embodiments, the brachytic markers are SNPs. In other embodiments, methods are described for using brachytic markers linked to a brachytic locus to identify plants with a brachytic allele, to introduce a brachytic phenotype into new plant genotypes (e.g., through marker-assisted breeding or genetic transformation), and to cultivate plants that are likely to have a brachytic phenotype.

The described brachytic markers may be used to facilitate marker-assisted selection (MAS) for the brachytic and/or early flowering trait in Solanaceae. Because the gene is recessive, partially dominant or co-dominant, marker-assisted selection provides significant advantages with respect to time, cost, and labor, when compared to traditional plant breeding using phenotype alone. The described brachytic markers offer utility in marker-assisted selection of brachytic Solanaceae varieties. Use of MAS in br breeding programs can facilitate incorporation of the locus into diverse genetic backgrounds. Such backgrounds can have genes responsible for other desired horticultural traits such as jointless pedicels traits (Scott, J. W., J. R. Myers, P. S. Boches, C. G. Nichols, and F. F. Angell. 2013. Classical genetics and traditional breeding, p. 60-61. In: B. E. Liedl, J. A. Labate, J. R. Stommel, A. Slade, and C. Kole (eds). Genetics, Genomics, and Breeding of Tomato. CRC Press, NW.) and prostrate growth habit (Ozminkowski, Jr., R. H., R. G. Gardner, W. R. Henderson, and R. H. Moll. 1990. Prostrate growth habit enhances fresh-market tomato fruit yield and quality. HortScience 25:914-915) among others.

In some embodiments, the markers and processes described herein are used to introgress a br allele from a brachytic plant into a recipient plant.

In some embodiments, Solanaceae plants produced by marker-assisted selection using one or more of the described brachytic marker are described.

In some embodiments, methods of producing brachytic Solanaceae plants and methods of genetically modifying a Solanaceae plant to produce a brachytic plant using a CRISPR system are described.

In some embodiments, brachytic plants created using a CRISPR system are described. Nucleic acids for producing a brachytic plant using a CRISPR system are described.

A. Marker Description

Described is a brachytic locus responsible for the brachytic phenotype in plants of the family Solanaceae (brachytic locus). The brachytic locus in tomato (*Solanum*) maps to a 763.1-kb interval between 74,936,467 and 75,699,595 bp on chromosome 1. Solanaceae plants homozygous for the br allele of the brachytic locus have shortened internode length. Solanaceae plants heterozygous for the br allele (one br allele and one normal allele) of the brachytic locus have intermediate internode length.

Brachytic markers useful for genotyping (mapping, tracking, identifying, analyzing) a brachytic locus in a Solanaceae plant are described. In some embodiments, a brachytic marker comprises a detectable genetic marker linked, closely linked, tightly linked, or extremely tightly linked to a brachytic locus. In some embodiments, a brachytic marker comprises a detectable genetic marker linked, closely linked, tightly linked, or extremely tightly linked to a genomic sequence encompassed by 74,936,467 and 75,699,595 bp on chromosome 1 tomato. In some embodiments, a brachytic marker is a detectable genetic marker linked, closely linked, tightly linked, or extremely tightly linked to one or more of: SEQ ID NO: 1 or a portion thereof, SEQ ID NO: 48 or a portion thereof, SEQ ID NO: 2 or a portion thereof, SEQ ID NO: 3 or a portion thereof, SEQ ID NO: 4 or a portion thereof, SEQ ID NO: 5 or portion thereof, SEQ ID NO: 6 or a portion thereof, SEQ ID NO: 7 or a portion thereof, and/or SEQ ID NO: 8 or a portion thereof. In some embodiments, a brachytic marker is a detectable genetic marker linked, closely linked, tightly linked, or extremely tightly linked to a homolog or ortholog of any of: SEQ ID NO: 1 or a portion thereof, SEQ ID NO: 48 or a portion thereof, SEQ ID NO: 2 or a portion thereof, SEQ ID NO: 3 or a portion thereof, SEQ ID NO: 4 or a portion thereof, SEQ ID NO: 5 or portion thereof, SEQ ID NO: 6 or a portion thereof, SEQ ID NO: 7 or a portion thereof, and/or SEQ ID NO: 8 or a portion thereof.

In some embodiments, a brachytic marker includes, but is not limited to, a single nucleotide polymorphism (SNPs) or an indel (insertions and deletions). Exemplary SNPs include, but are not limited to brM1, brM2, brM3, brM4, brM5, brM6, brM7, brM8, solcap_18634, solcap_456, and solcap_457. In some embodiments, the brachytic marker comprises a nucleotide sequence comprising SEQ ID NO: 1 or a portion thereof, SEQ ID NO: 48 or a portion thereof, SEQ ID NO: 2 or a portion thereof, SEQ ID NO: 3 or a portion thereof, and/or SEQ ID NO: 4 or a portion thereof, SEQ ID NO: 5 or portion thereof, SEQ ID NO: 6 or a portion thereof, SEQ ID NO: 7 or a portion thereof, and/or SEQ ID NO: 8 or a portion thereof. In some embodiments, the brachytic marker comprises an ortholog sequence of: SEQ ID NO: 1 or a portion thereof, SEQ ID NO: 48 or a portion thereof, SEQ ID NO: 2 or a portion thereof, SEQ ID NO: 3 or a portion thereof, and/or SEQ ID NO: 4 or a portion thereof, SEQ ID NO: 5 or portion thereof, SEQ ID NO: 6 or a portion thereof, SEQ ID NO: 7 or a portion thereof, and/or SEQ ID NO: 8 or a portion thereof.

In some embodiments, a brachytic marker is a detectable genetic marker comprising an amplification product comprising all or a portion of SEQ ID NO: 1, an amplification product comprising all or a portion of SEQ ID NO: 48, or an amplification product comprising all or a portion of SEQ ID NO: 2.

Additional genetic markers can be identified by any method known in the art. The widespread availability, speed, and ease of DNA sequencing provides for identification of genetic marker sequence from amplified products.

Genetic markers include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), and other markers known in the art.

Also provided are nucleic acid molecules. Such molecules include those nucleic acid molecules capable of detecting a polymorphism (brachytic marker) genetically or physically linked to a brachytic locus. In one aspect, the nucleic acid molecule is capable of detecting the presence or absence of a marker located less than 50, 40, 30, 20, 10, 5, 2, or 1 centimorgans (cM) from a brachytic locus.

B. Marker Detection

The described brachytic markers can be detected by any means known in the art for detecting genetic markers.

A number of methods to rapidly test plants and progeny for the presence or absence of genetic markers are known in the art. Polymorphisms in DNA sequences can be detected or typed by a variety of effective methods known in the art, including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252, all of which are incorporated herein by reference in their entirety. The compositions and methods described herein can be used in conjunction with any polymorphism typing method to type polymorphisms in genomic DNA samples. Genomic DNA samples include, but are not limited to, genomic DNA isolated directly from a plant, cloned genomic DNA, or amplified genomic DNA.

Marker testing methods include, but are not limited to, polymerase chain reaction (PCR)-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

In some embodiment, detection of brachytic markers in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. A method of achieving such amplification employs the polymerase chain reaction (PCR).

One method of achieving such amplification employs PCR, using primer pairs that are capable of hybridizing to distal and proximal sequences that define a polymorphism in its double-stranded form.

In some embodiments, typing DNA based on mass spectrometry can also be used to detect a brachytic marker. Such methods are disclosed in U.S. Pat. Nos. 6,613,509 and 6,503,710, and references found therein.

In some embodiments, a brachytic marker is detected by hybridization to allele-specific oligonucleotide (ASO) probes. ASO probes are disclosed in U.S. Pat. Nos. 5,468, 613 and 5,217,863. U.S. Pat. No. 5,468,613. Single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

In some embodiments, a brachytic marker is detected by probe ligation methods. Probe ligation methods disclosed in U.S. Pat. No. 5,800,944 where sequence of interest is amplified and hybridized to probes followed by ligation to detect a labeled part of the probe.

In some embodiments, microarrays also used for brachytic marker detection. For microarray detection, oligonucleotide probe sets are assembled in an overlapping fashion to represent a single sequence such that a difference in the target sequence at one point would result in partial probe hybridization (Borevitz et al., Genome Res. 13:513-523, 2003; Cui et al., Bioinformatics 21:3852-3858, 2005). Typing of target sequences by microarray-based methods is disclosed in U.S. Pat. Nos. 6,799,122; 6,913,879; and 6,996, 476.

In some embodiments, methods for detecting SNPs and indels include single base extension (SBE) methods. Examples of SBE methods include, but are not limited to, those disclosed in U.S. Pat. Nos. 6,004,744; 6,013,431; 5,595,890; 5,762,876; and 5,945,283.

In some embodiments, a brachytic markers can be directly identified or sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

In some embodiments, the presence of a brachytic marker in a plant may be detected through the use of a nucleotide probe. A probe may be, but is not limited to, nucleotide molecule, polynucleotide, oligonucleotide, DNA molecule, RNA molecule, PNA, UNA, locked nucleotide, or modified polynucleotide. Polynucleotides can be synthesized by any means known in the art. A probe may contain all or a portion of the nucleotide sequence of the genetic marker and optionally, one or more additional sequences. The one or more additional sequences can be contiguous nucleotide sequence from the plant genome, non-contiguous nucleotide sequence from the plant genome, or sequence that is not from the plant genome. Additional, contiguous nucleotide sequence can be "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome.

In some embodiments, sequence of a non-contiguous probe is located sufficiently close to the sequence of the original marker on the genome so that the non-contiguous probe is genetically linked to the same gene or trait (e.g., br allele). For example, in some embodiments, a noncontiguous probe is located within 500 kb, 450 kb, 400 kb, 350 kb, 300 kb, 250 kb, 200 kb, 150 kb, 125 kb, 100 kb, 0.9 kb, 0.8 kb, 0.7 kb, 0.6 kb, 0.5 kb, 0.4 kb, 0.3 kb, 0.2 kb, or 0.1 kb of the original marker on the Solanaceae genome.

A polynucleotide probe may be labeled or unlabeled. A wide variety of techniques are readily available in the art for labeling a nucleotide probe. Nucleotide labels include, but are not limited to, radiolabeling, fluorophores, haptens, antibodies, antigens, enzymes, enzyme substrates, enzyme cofactors, and enzyme inhibitors. A label may provide a detectable signal by itself (e.g., a radiolabel or fluorophore) or in conjunction with other agents.

A probe may be an exact copy of a marker to be detected. A probe may also be a nucleic acid molecule comprising, or consisting of, a nucleotide sequence which is substantially identical to a cloned segment of the Solanaceae chromosomal DNA. The term "substantially identical" may refer to nucleotide sequences that are more than 85% identical. For example, a substantially identical nucleotide sequence may be 86%, 87%, 88%, 89%, 90%, 91%, 92%, 93%, 94%, 95%, 96%, 97%, 98%, or 99% identical to the reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired. Thus, an oligonucleotide probe is "specifically hybridizable" to a maker allele if stable and specific binding occurs between the oligonucleotide probe and the marker allele (e.g., a SNP marker) under stringent hybridization conditions, but stable and specific binding does not occur between the oligonucleotide probe and the wild-type allele at the marker position.

In some embodiments, a probe comprises a pair primers designed to produce an amplification product, wherein the amplification product is directly or indirectly determinative for the presence or absence of a brachytic marker.

C. Genotyping

In some embodiments, the described brachytic markers may be used to identify a Solanaceae plant with one or more determinants of the brachytic phenotype. The presence or absence of the brachytic marker can be determined by any method know in the art, including, but not limited to, those methods described above. In some embodiments, nucleic acid molecules (e.g., genomic DNA or mRNA) may be extracted from a plant. The extracted nucleic acid molecules may then be contacted with one or more probes that are specifically hybridizable to markers linked to the brachytic phenotype. Specific hybridization of the one or more probes to the extracted nucleic acid molecules is indicative of the presence of one or more determinants of brachytic in the plant.

In some embodiments, the described brachytic markers can be used to identify early flowering plants or plants having accelerated flowering.

In some embodiments, genotyping a progeny Solanaceae plant having or suspected of having a br allele and having a least one parent plant having a br allele comprises: identifying at least one brachytic marker in the parent plant and determining the presence or absence of the brachytic marker in the progeny plant. The presence or absence of the brachytic marker can be determined by any method know in the art.

In some embodiments, determining the presence or absence of the brachytic marker in the progeny plant comprises: amplifying a nucleotide sequence containing a brachytic marker and producing an amplification product wherein the amplification product is determinative for the presence and/or absence of the brachytic marker. The amplification product can comprises a nucleotide sequence comprising all or a portion of SEQ ID NO: 1 or SEQ ID NO: 48.

Other non-limited examples include: detection by electrophoretic techniques including single strand conformational polymorphisms, denaturing gradient gel electrophoresis, and cleavage fragment length polymorphisms.

D. Marker-Assisted Selection and Introgressing

Nucleic acid-based analyses for determining the presence or absence of the genetic polymorphism (i.e. for genotyping) can be used in breeding programs for identification, selection, introgression, and the like. The analysis may be used to select for genes, portions of genes, loci, alleles, or genomic regions that comprise or are linked to a genetic marker.

Marker-assisted introgression involves the transfer of a chromosomal region or locus defined by one or more markers from a first genetic background to a second. Offspring of a cross that contains the introgressed genomic region can be identified by the combination of markers characteristic of the desired introgressed genomic region from a first genetic background and both linked and unlinked markers characteristic of the second genetic background. The described brachytic markers can be used to identify and track introgression of br locus into recipient lines.

Methods of using genetic markers that are linked to a trait of interest (e.g., brachytic and/or early flowering in Solanaceae) to identify plants having the trait of interest may result in a cost savings for plant developers, because such methods may eliminate the need to phenotype individual plants generated during development (for example, by crossing Solanaceae plant varieties having brachytic with plant having one or more desired traits).

In some embodiments, markers linked to the brachytic locus in Solanaceae may be used to transfer segment(s) of DNA that contain one or more determinants of brachytic. In particular embodiments, the brachytic markers may be selected from a group of markers comprising the markers listed in Tables 2-6 or SEQ ID NOs: 1-8 and 48 and markers that are their equivalents. In some embodiments, a marker may be selected from the group comprising, or consisting of: brM1, brM2, brM3, brM4, brM5, brM6, brM7, brM8, solcap_18634, solcap_456, solcap_457, SEQ ID NO: 1 or a portion thereof, SEQ ID NO: 48 or a portion thereof, SEQ ID NO: 2 or a portion thereof, an ortholog of SEQ ID NO: 1 or a portion thereof, an ortholog of SEQ ID NO: 48 or a portion thereof, and an ortholog of SEQ ID NO: 2 or a portion thereof.

In some embodiments, methods for using brachytic markers linked to a brachytic locus in Solanaceae to transfer or introgress a segment of DNA that contains one or more determinants of the brachytic (e.g. a br allele) comprise analyzing a genomic DNA of a donor brachytic parent having a brachytic genotype and a recipient parent having a recipient genotype with probes that are specifically hybridizable to brachytic markers; sexually crossing the two parental plant genotypes to obtain a progeny population, and analyzing those progeny for the presence or absence of the brachytic markers; backcrossing the progeny that contain the brachytic markers to a recipient plant having the recipient genotype to produce a first backcross population, and then continuing with a backcrossing program until a final progeny is obtained that comprises any desired trait(s) exhibited by the recipient genotype and the brachytic phenotype. In particular embodiments, individual progeny obtained in each crossing and backcrossing step are selected by brachytic marker analysis at each generation.

In some embodiments, the described brachytic markers may be used to introduce one or more determinants of brachytic (e.g. a brachytic locus or br allele) into a Solanaceae plant by genetic transformation. The markers may be selected from a group of brachytic markers comprising the markers listed in Tables 2-6 or SEQ ID NOs: 1-8 and 48 and markers that are their equivalents. In some embodiments, a method for introducing one or more determinants of brachytic into a plant by genetic recombination may comprise analyzing a genomic DNA of a Solanaceae plant with probes that are specifically hybridizable to brachytic markers to identify one or more determinants of brachytic in the plant; isolating a segment of the genomic DNA of the plant comprising the brachytic markers, for example, by extracting the genomic DNA and digesting the genomic DNA with one or more restriction endonuclease enzymes or by PCR amplification; optionally amplifying the isolated segment of DNA; introducing the isolated segment of DNA into a cell or tissue of a host plant; and analyzing the DNA of the host plant with probes that are specifically hybridizable to the brachytic markers to identify the one or more determinants of brachytic in the host plant. In particular embodiments, the isolated segment of DNA may be introduced into the host plant such that it is stably integrated into the genome of the host plant. In some embodiments, the DNA comprises SEQ ID NO: 1. In some embodiments, the DNA comprises SEQ ID NO: 48.

A brachytic locus can be introduced from any plant that contains a br allele (donor plant) to any recipient tomato plant. In some embodiments, while maintaining the introduced brachytic locus, the genetic contribution of the donor plant can be reduced by back-crossing or other suitable approaches. In one aspect, the nuclear genetic material derived from the donor plant can be less than or about 50%, less than or about 25%, less than or about 13%, less than or about 5%, 3%, 2% or 1%, but that genetic material contains the brachytic locus.

A brachytic locus or allele may be introduced into a transgenic tomato line. A transgenic tomato line can contain one or more genes for herbicide tolerance, increased yield, insect control, fungal disease resistance, virus resistance, bacterial disease resistance, germination and/or seedling growth control, enhanced animal and/or human nutrition, improved processing traits, or improved flavor, among others.

In some embodiments are described methods of genotyping a Solanaceae plant having or suspected of having a br allele comprising: identifying at least one brachytic marker in the plant wherein the brachytic marker comprises a detectable genetic marker linked, closely linked, tightly linked, or extremely tightly linked to any of SEQ ID NO: 1-8 and 48 or an ortholog thereof or a portion of any of SEQ ID NO: 1-8 and 48 or an ortholog thereof.

In some embodiments are described methods of genotyping a progeny Solanaceae plant having or suspected of having a br allele and having a least one parent plant having a br allele comprising: identifying at least one brachytic marker in the parent plant and determining the presence or absence of the brachytic marker in the progeny plant wherein the brachytic marker comprises a detectable genetic marker linked, closely linked, tightly linked, or extremely tightly linked to any of SEQ ID NO: 1-8 and 48 or an ortholog thereof or a portion of any of SEQ ID NO: 1-8 and 48 or an ortholog thereof.

In some embodiments are described methods of genotyping a progeny Solanaceae plant having or suspected of early flowering and having a least one parent plant having a br allele comprising: identifying at least one brachytic marker in the parent plant and determining the presence or absence of the brachytic marker in the progeny plant wherein the brachytic marker comprises a detectable genetic marker linked, closely linked, tightly linked, or extremely tightly linked to any of SEQ ID NO: 1-8 and 48 or an ortholog thereof or a portion of any of SEQ ID NO: 1-8 and 48 or an ortholog thereof.

In some embodiments, the presence or absence of the brachytic marker in the progeny plant comprises: amplifying a nucleotide sequence containing a brachytic marker to produce an amplification product wherein the amplification product is determinative for the presence and/or absence of the brachytic marker.

In some embodiments are described methods for introgressing a brachytic locus into a recipient Solanaceae plant comprising: a) providing a donor Solanaceae plant known to have at least one br allele; b) genotyping the donor brachytic Solanaceae plant to identify one or more donor brachytic markers linked to the br allele of the donor Solanaceae plant; c) crossing the donor Solanaceae plant with at least one recipient Solanaceae plant to form a progeny population; and, d) selecting from the progeny population one or more Solanaceae plants comprising the one or more donor brachytic markers; wherein the brachytic marker comprises a detectable genetic marker linked, closely linked, tightly linked, or extremely tightly linked to any of SEQ ID NO: 1-8 and 48 or an ortholog thereof or a portion of any of SEQ ID NO: 1-8 and 48 or an ortholog thereof. The recipient plant may or may not be brachytic or have a br allele. The recipient plant can also be genotyped with respect to the brachytic locus.

In some embodiments are described methods for transferring a brachytic locus in a tomato plant, the method comprising: a) identifying a donor tomato plant having a brachytic phenotype and a recipient tomato plant having one or more desired traits; b) genotyping the donor tomato plant to identify one or more donor genetic markers linked to a donor brachytic locus wherein the donor brachytic locus comprises an interval between 74,936,467 and 75,699,595 bp on chromosome 1; c) optionally genotyping the recipient tomato plant identify one or more recipient genetic markers linked to a recipient brachytic locus wherein the recipient brachytic locus comprises an interval between 74,936,467 and 75,699,595 bp on chromosome 1; d) crossing the donor tomato plant with the recipient tomato plant to obtain a progeny population; e) identifying one or more plants from the progeny population having at least one of the one or more desired traits and at least one donor brachytic locus as determined by the presence of the donor genetic markers; f) backcrossing at least one plant from the progeny population identified in step (e) with a second plant from the progeny population identified in step (e) or a second recipient tomato plant the same or substantially similar genotype to the recipient tomato plant in step (a) to produce an F2 population; and g) repeating steps (e) and (f) until at least one plant is identified that comprises a homozygous donor brachytic locus and the one or more desired traits from the recipient tomato plant.

In some embodiments are described methods for producing a brachytic tomato plant, the method comprising the steps of: a) providing a donor brachytic tomato plant; b) crossing the donor brachytic tomato plant with at least one recipient non-brachytic tomato plant to produce offspring tomato plants; and, c) detecting in chromosome 1 of at least one offspring plant the presence of a donor brachytic locus from the donor tomato plant, wherein the brachytic locus is located on chromosome 1 and comprises an interval between 74,936,467 and 75,699,595 bp. In some embodiments, the method further comprises: backcrossing at least one offspring tomato plant to a second offspring tomato plant wherein the second offspring plant contains a donor brachytic locus from the donor tomato plant, wherein the brachytic locus is located on chromosome 1 and comprises the interval between 74,936,467 and 75,699,595 bp to produce F2 offspring plants. The F2 and/or further generation progeny can then be genotyped for the presence of the donor brachytic locus. In some embodiments, progeny homozygous for the donor brachytic locus are selected. In other embodiments, the method further comprises: backcrossing at least one offspring tomato plant to a recipient non-brachytic tomato plant to produce offspring tomato plants to produce F2 plants and detecting in at least one F2 plant the presence of a donor brachytic locus from the donor tomato plant.

In some embodiments are described methods for producing a brachytic plant comprising: selecting a plant having at least one br allele, identifying one or more brachytic markers in the brachytic plant, and using the one or more brachytic makers to facilitate marker-assisted selection of offspring having the br allele.

In some embodiments are described methods for producing an early flowering plant comprising: selecting a plant having at least one br allele, identifying one or more brachytic markers in the brachytic plant, and using the one or more brachytic makers to facilitate marker-assisted selection of offspring having the br allele.

In some embodiments are described methods for producing a brachytic and/or early flowering plant comprising: a) selecting a donor plant having at least one donor br allele and identifying are least one donor brachytic marker linked to the donor br allele; b) selecting a recipient plant wherein the recipient plant optionally has at least one recipient br allele and, if present, identifying least one recipient brachytic marker linked to the recipient br allele; c) crossing the donor plant with recipient plant to produce a population of progeny plants; d) genotyping the progeny plants for the presence or absence of at least one donor brachytic marker and optionally the at least one recipient brachytic marker; and, e) selecting progeny plants containing the at least one donor brachytic marker or the at least one donor brachytic markers and the at least one recipient brachytic marker.

In some embodiments, at least two brachytic markers are used for marker-assisted selection. The at least two brachytic markers can flank the br allele.

Any of the described markers can be used for marker-assisted selection of the brachytic locus. Further, any of the described compositions or methods for detecting a brachytic locus can be used in marker-assisted selection of the brachytic locus. Additionally, any methods know in the art for detecting a genetic marker can be used for marker-assisted selection of the brachytic locus.

The described methods can be used for marker-assisted selected and/or introgressing of the brachytic locus in a Solanaceae plant. A Solanaceae plant can be a *Solanum* or a *Capsicum* plant. A *Solanum* plant can be a *S. melongena* (eggplant) plant, *S. tuberosum* (potato) plant, or a *S. lycopersicum* (tomato) plant. A *Capsicum* plant can be a *C. annuum* (pepper) plant or a *C. frutescens* (tabasco pepper) plant. The term tomato includes but is not limited to, any species of tomato.

In some embodiments, we describe Solanaceae plants comprising an introgressed brachytic locus from a brachytic parent donor plant into a recipient plant.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

In some embodiments, methods for producing a brachytic Solanaceae plant are described, the methods comprising the steps of: (a) isolating one or more nucleic acids from one or more of Solanaceae plants; (b) genotyping said one or more nucleic acids for the presence of a brachytic marker wherein the brachytic marker comprises a detectable genetic marker linked, closely linked, tightly linked, or extremely tightly linked to any of SEQ ID NOs: 1-8 and 48 or an ortholog thereof, or a fragment of any of SEQ ID NOs: 1-8 and 48 or an ortholog thereof; (c) selecting a first Solanaceae plant on the basis of the presence of the brachytic marker genotyped in (b); (d) crossing the first Solanaceae plant of (c) with a second Solanaceae plant not having the brachytic marker; (e) collecting seed from the cross of (d); and (f) growing a progeny Solanaceae plant from the seed of (e), wherein said progeny Solanaceae plant comprises in its genome the brachytic marker.

In some embodiments, methods of producing a population of Solanaceae plants or seeds are described, the methods comprising: genotyping a first population of Solanaceae plants or seeds for the presence of a brachytic marker wherein the brachytic marker comprises a detectable genetic marker linked, closely linked, tightly linked, or extremely tightly linked to any of SEQ ID NOs: 1-8 and 48 or an ortholog thereof, or a fragment of any of SEQ ID NOs: 1-8 and 48 or an ortholog thereof; selecting from said first population one or more Solanaceae plants or seeds comprising said brachytic marker; and crossing or selfing said selected one or more Solanaceae plants or plants grown from said selected seeds to produce a second population of progeny Solanaceae plants or seeds comprising said brachytic marker.

In some embodiments, methods of introgressing a br allele into a Solanaceae plant are described, the methods comprising: (a) crossing at least one brachytic Solanaceae plant with at least one non brachytic Solanaceae plant in order to form a segregating population, (b) screening said segregating population with one or more brachytic markers to determine if one or more Solanaceae plants from said segregating population contains the one or more brachytic markers, the one or more brachytic makers comprising one or more detectable genetic markers linked, closely linked, tightly linked, or extremely tightly linked to any of SEQ ID NOs: 1-8 and 48 or an ortholog thereof, or a fragment of any of SEQ ID NOs: 1-8 and 48 or an ortholog thereof.

E. Transgenic Plants

Also provided are methods of generating a transgenic brachytic plant. In one embodiment, a method of generating a transgenic brachytic plant comprises introducing into a plant cell a nucleic acid molecule encoding br allele and selecting plants in which the brachytic locus is replace by the br allele.

In some embodiments, the transgene comprises SEQ ID NO: 1, SEQ ID NO: 48, SEQ ID NO: 2, SEQ ID NO: 3, or SEQ ID NO: 4 or a fragment thereof. In some embodiments, the transgene comprises a homolog of SEQ ID NO: 1, SEQ ID NO: 48, SEQ ID NO: 2, SEQ ID NO: 3, or SEQ ID NO: 4 or a fragment thereof. In some embodiments, the transgene comprises an ortholog of SEQ ID NO: 1, SEQ ID NO: 48, SEQ ID NO: 2, SEQ ID NO: 3, or SEQ ID NO: 4 or a fragment thereof.

The transgene may be introduced into a plant cell or cells using a number of methods known in the art, including but not limited to electroporation, DNA bombardment or biolistic approaches, microinjection, via the use of various DNA-based vectors such as *Agrobacterium tumefaciens* and *Agrobacterium rhizogenes* vectors, and CRISPR or CRISPR/Cas9. Once a plant cell has been successfully transformed, it may be cultivated to regenerate a transgenic plant.

In some embodiments, *Agrobacterium tumefaciens* is used to generate a transgenic plant. There are numerous vectors designed for *Agrobacterium* transformation. For stable transformation, *Agrobacterium* systems utilize "binary" vectors that permit plasmid manipulation in both *E. coli* and *Agrobacterium*, and typically contain one or more selectable markers to recover transformed plants (Hellens et al., 2000, *Technical focus: A guide to Agrobacterium binary Ti vectors*. Trends Plant Sci 5:446-451). Binary vectors for use in *Agrobacterium* transformation systems typically comprise the borders of T-DNA, multiple cloning sites, replication functions for *Escherichia coli* and *A. tumefaciens*, and selectable marker and reporter genes.

Various methods for introducing the transgene expression vector constructs of the invention into a plant or plant cell are well known to those skilled in the art, and any capable of transforming the target plant or plant cell may be utilized.

*Agrobacterium*-mediated transformation of a large number of plants are extensively described in the literature (see, for example, *Agrobacterium* Protocols, Wan, ed., Humana Press, $2^{nd}$ edition, 2006). Various methods for introducing DNA into Agrobacteria are known, including electroporation, freeze/thaw methods, and triparental mating. In some embodiments, a pMON316-based vector is used in the leaf disc transformation system of Horsch et al. Other commonly used transformation methods include, but are not limited to, microprojectile bombardment, biolistic transformation, and protoplast transformation of naked DNA by calcium, polyethylene glycol (PEG) or electroporation (Paszkowski et al., 1984, EMBO J. 3: 2727-2722; Potrykus et al., 1985, Mol. Gen. Genet. 199: 169-177; Fromm et al., 1985, Proc. Nat. Acad. Sci. USA 82: 5824-5828; Shimamoto et al., 1989, Nature, 338: 274-276.

To transgenic plants may be used to generate subsequent generations (e.g., $T_1$, $T_2$, etc.) by selfing of primary or secondary transformants, or by sexual crossing of primary or secondary transformants with other plants (transformed or untransformed).

F. CRISPR/Cas

In some embodiments, methods of producing brachytic plants and methods of genetically modifying a plant to produce a brachytic plant using a CRISPR/Cas system are described. In some embodiments, brachytic plants created using a CRISPR/Cas system are described. In some embodiments, nucleic acids for producing a brachytic plant using a CRISPR/Cas system are described.

In some embodiments, a CRISPR system comprises an RNA-guided DNA endonuclease enzyme and a guide RNA. In some embodiments the RNA-guided DNA endonuclease enzyme is a Cas9 protein. In some embodiments, a CRISPR system comprises one or more nucleic acids encoding an RNA-guided DNA endonuclease enzyme (such as, but not limited to a Cas9 protein) and a guide RNA. A guide RNA can comprise a CRISPR RNA (crRNA) and a trans-activating CRISPR RNA (tracrRNA), either as separate molecules or a single chimeric guide RNA (sgRNA). The guide RNA contains a guide sequence having complementarity to a sequence in the target gene genomic region. The Cas protein can be introduced into the plant in the form of a protein or a nucleic acid (DNA or RNA) encoding the Cas protein (e.g., operably linked to a promoter expressible in the plant). The guide RNA can be introduced into the plant in the form of RNA or a DNA encoding the guide RNA (e.g., operably linked to a promoter expressible in the plant). In some embodiments, the CRISPR system can be delivered to a plant or plant cell via a bacterium. The bacterium can be, but is not limited to, *Agrobacterium tumefaciens*.

The CRISPR system is designed to target the brachytic locus and/or br allele. The CRISPR/Cas system can be, but is not limited to, a CRISPR class 1 system, CRISPR class 2 system, CRISPR/Cas system, a CRISPR/Cas9 system, a CRISPR/zCas9 system or CRISPR/Cas3 system.

In some embodiments, the CRISPR system comprises a guide sequence comprising a 17-20 nucleotide sequence comprising 17-20 contiguous nucleotides from SEQ ID NO: 49 (nucleotides 21742-22373 of SEQ ID NO: 64) or a complement thereof, SEQ ID NO: 64 or a complement thereof, nucleotides 19742-22373 of SEQ ID NO: 64 or a complement thereof, nucleotides 16742-22373 of SEQ ID NO: 64 or a complement thereof, nucleotides 11742-22373 of SEQ ID NO: 64 or a complement thereof, nucleotides 1-22373 of SEQ ID NO: 64 or a complement thereof, nucleotides 21742-24373 of SEQ ID NO: 64 or a complement thereof, nucleotides 21742-27373 of SEQ ID NO: 64 or a complement thereof, nucleotides 21742-29135 of SEQ ID NO: 64 or a complement thereof, nucleotides 19742-24373 of SEQ ID NO: 64 or a complement thereof, nucleotides 16742-27373 of SEQ ID NO: 64 or a complement thereof, or nucleotides 11742-27373 of SEQ ID NO: 64 or a complement thereof wherein the 17-20 nucleotide sequence is unique compared to the rest of the genome and immediately adjacent (5') to a protospacer-adjacent motif (PAM) site. It is noted that, for RNA sequences, T's of SEQ ID NO: 49 and SEQ ID NO: 64 can be U's. In some embodiments, the PAM site is 5'-NGG-3'. In some embodiments, two or more gRNAs can be used. The two or more gRNAs can used with the same RNA-guided DNA endonuclease or different RNA-guided DNA endonucleases.

G. List of Embodiments

1. A method of genotyping a Solanaceae plant having or suspected of having a br allele and/or exhibiting early flowering comprising, identifying at least one brachytic marker in the plant wherein the brachytic marker comprises a detectable genetic marker linked, closely linked, tightly linked, or extremely tightly linked to any of SEQ ID NOs:

1-8 and 48 or an ortholog thereof or a fragment of any of SEQ ID NOs: 1-8 and 48 or an ortholog thereof.

2. The method of embodiment 1, wherein the Solanaceae plant is a tomato plant.

3. The method of embodiment 1 or 2, wherein the brachytic marker comprises: a PCR amplification product, a single nucleotide polymorphism (SNP), a restriction fragment length polymorphism (RFLP), an amplified fragment length polymorphism (AFLP), a simple sequence repeat (SSR), a simple sequence length polymorphism (SSLP), an insertion/deletion polymorphism (indel), a variable number tandem repeat (VNTRs), or a random amplified polymorphic DNA (RAPD).

4. The method of embodiment 3, wherein the PCR amplification product comprises all or a portion of SEQ ID NO: 1, SEQ ID NO: 48, or SEQ ID NO: 2, or an ortholog thereof.

5. The method of embodiment 1 or 2, wherein the brachytic marker comprises a single nucleotide polymorphism (SNP).

6. The method of embodiment 5, wherein the SNP is selected from the group consisting of brM1, brM2, brM3, brM4, brM5, brM6, brM7, brM8, solcap_18634, solcap_456, and solcap_457.

7. The method of embodiment 2, wherein the brachytic marker is in a continuous nucleic acid region comprising an interval between 74,936,467 and 75,699,595 bp on chromosome 1 of the tomato plant, or is linked, closely linked, tightly linked, or extremely tightly linked to an interval between 74,936,467 and 75,699,595 bp on chromosome 1 of the tomato plant 8. A method of genotyping a progeny Solanaceae plant having or suspected of having a br allele and/or exhibiting early flowering and having at least one parent plant having a br allele, comprising identifying at least one brachytic marker in the parent plant and determining the presence or absence of the brachytic marker in the progeny plant, wherein the brachytic marker comprises a detectable genetic marker linked, tightly linked, or extremely tightly linked to any of SEQ ID NO: 1-8 and 48 or an ortholog thereof or a portion of any of SEQ ID NOs: 1-8 and 48 or an ortholog thereof.

9. The method of embodiment 8, wherein the Solanaceae plant is a tomato plant.

10. The method of embodiment 8 or 9, wherein the brachytic marker comprises a PCR amplification product, a single nucleotide polymorphism (SNP), a restriction fragment length polymorphism (RFLP), an amplified fragment length polymorphism (AFLP), a simple sequence repeat (SSR), a simple sequence length polymorphism (SSLP), an insertion/deletion polymorphism (indel), a variable number tandem repeat (VNTRs), or a random amplified polymorphic DNA (RAPD).

11. The method of embodiment 10, wherein the PCR amplification product comprises all or a portion of SEQ ID NO: 1, SEQ ID NO: 48, or SEQ ID NO: 2 or an ortholog thereof.

12. The method of embodiment 8 or 9, wherein the brachytic marker comprises a single nucleotide polymorphism (SNP).

13. The method of embodiment 8, wherein the SNP is selected from the group consisting of brM1, brM2, brM3, brM4, brM5, brM6, brM7, brM8, solcap_18634, solcap_456, and solcap_457.

14. The method of embodiment 8, wherein the brachytic marker is in a continuous nucleic acid region comprising an interval between 74,936,467 and 75,699,595 bp on chromosome 1 of the tomato plant, or is linked, closely linked, tightly linked, or extremely tightly linked to an interval between 74,936,467 and 75,699,595 bp on chromosome 1 of the tomato plant 15. The method of any one of embodiments 8-14, wherein determining the presence or absence of the brachytic marker in the progeny plant comprises amplifying a nucleotide sequence containing the brachytic marker to produce an amplification product, wherein the amplification product is determinative for the presence and/or absence of the brachytic marker.

16. The method of any one of embodiments 1-14, wherein the brachytic marker is detected through the use of a nucleotide probe.

17. A method for introgressing a brachytic locus into a recipient Solanaceae plant, comprising:
a) providing a donor Solanaceae plant known to have at least one br allele;
b) genotyping the donor brachytic Solanaceae plant to identify one or more donor brachytic markers linked to the br allele of the donor Solanaceae plant;
c) crossing the donor Solanaceae plant with at least one recipient Solanaceae plant to form a progeny population; and,
d) selecting from the progeny population one or more Solanaceae plants comprising the one or more donor brachytic markers.

18. The method of embodiment 17, wherein the recipient Solanaceae plant is known to have at least one br allele.

19. The method of embodiment 18, further comprising genotyping the recipient brachytic Solanaceae plant to identify one or more recipient brachytic markers linked to the br allele of the recipient Solanaceae plant.

20. The method of embodiment 19, further comprising selecting from the progeny population one or more Solanaceae plants comprising the one or more donor brachytic markers and the one or more recipient brachytic markers.

21. The method of embodiment 19 or 20, wherein the donor brachytic markers and/or recipient brachytic markers independently comprise: restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (indels), variable number tandem repeats (VNTRs), or random amplified polymorphic DNA (RAPD).

22. The method of any one of embodiments 17-21, wherein the donor brachytic markers comprise a detectable genetic marker linked, closely linked, tightly linked, or extremely tightly linked to any of SEQ ID NO: 1-8 and 48 or an ortholog thereof or a portion of any of SEQ ID NO: 1-8 and 48 or an ortholog thereof.

23. The method of any one of embodiments 17-22, wherein the Solanaceae plant is a tomato plant.

24. The method of embodiment 21 or 22, wherein the donor brachytic markers comprise a PCR amplification product.

25. The method of embodiment 24, wherein the donor brachytic markers comprise an amplification product comprising all or a portion of SEQ ID NO: 1, SEQ ID NO: 48, or SEQ ID NO: 2 or an ortholog thereof.

26. The method of embodiment 21 or 22, wherein the donor brachytic markers comprise a single nucleotide polymorphism (SNP).

27. The method of embodiment 26, wherein the SNPs are independently selected from the group consisting of: brM1, brM2, brM3, brM4, brM5, brM6, brM7, brM8, solcap_18634, solcap_456, and solcap_457.

28. The method of embodiment 23, wherein the donor brachytic markers are in a continuous nucleic acid region comprising an interval between 74,936,467 and 75,699,595 bp on chromosome 1 of the tomato plant, or is linked, closely linked, tightly linked, or extremely tightly linked to an interval between 74,936,467 and 75,699,595 bp on chromosome 1 of the tomato plant 29. A method for transferring a brachytic locus in a tomato plant, comprising:

a) identifying a donor tomato plant having a brachytic phenotype and a recipient tomato plant having one or more desired traits;

b) genotyping the donor tomato plant to identify one or more donor genetic markers linked to a donor brachytic locus wherein the donor brachytic locus comprises an interval between 74,936,467 and 75,699,595 bp on chromosome 1;

c) optionally genotyping the recipient tomato plant identify one or more recipient genetic markers linked to a recipient brachytic locus wherein the recipient brachytic locus comprises an interval between 74,936,467 and 75,699,595 bp on chromosome 1;

d) crossing the donor tomato plant with the recipient tomato plant to obtain a progeny population;

e) identifying one or more plants from the progeny population having at least one of the one or more desired traits and at least one donor brachytic locus as determined by the presence of the donor genetic markers;

f) backcrossing at least one plant from the progeny population identified in step (e) with a second plant from the progeny population identified in step (e) or a second recipient tomato plant the same or substantially similar genotype to the recipient tomato plant in step (a) to produce an F2 population; and g) repeating steps (e) and (f) until at least one plant is identified that comprises a homozygous donor brachytic locus and the one or more desired traits from the recipient tomato plant.

30. The method of embodiment 29 wherein the donor genetic markers and/or recipient genetic markers are tightly linked to the brachytic locus.

31. The method of embodiment 29 wherein the donor genetic markers and/or recipient genetic markers are extremely tightly linked to the brachytic locus.

32. The method of embodiment 29 wherein the donor genetic markers and/or recipient genetic markers are within 65 megabases of a genomic sequence comprising SEQ ID NO: 1 or a portion thereof, SEQ ID NO: 48 or a portion thereof, or SEQ ID NO: 2 or a portion thereof.

33. The method of any one of embodiments 29-32, wherein the donor genetic markers and/or recipient genetic markers independently comprise: restriction fragment length polymorphisms (RFLPs), amplified fragment length polymorphisms (AFLPs), simple sequence repeats (SSRs), simple sequence length polymorphisms (SSLPs), SNPs, insertion/deletion polymorphisms (indels), variable number tandem repeats (VNTRs), or random amplified polymorphic DNA (RAPD).

34. The method of embodiment 33, wherein the SNPs are independently selected from the group consisting of: brM1, brM2, brM3, brM4, brM5, brM6, brM7, brM8, solcap_18634, solcap_456, and solcap_457.

35. A method for producing a brachytic and/or early flowering tomato plant, comprising:

a) providing a donor brachytic tomato plant;

b) crossing the donor brachytic tomato plant with at least one recipient non-brachytic tomato plant to produce offspring tomato plants; and c) detecting in chromosome 1 of at least one offspring plant the presence of a donor brachytic locus from the donor tomato plant, wherein the brachytic locus is located on chromosome 1 and comprises an interval between 74,936,467 and 75,699,595 bp.

36. The method of embodiment 35, further comprising backcrossing the at least one offspring tomato plant to a second offspring tomato plant containing the donor brachytic locus from the donor tomato plant to produce F2 offspring plants.

37. The method of embodiment 36, further comprising detecting in chromosome 1 of at least one F2 offspring plant the presence of the donor brachytic locus from the donor tomato plant.

38. The method of embodiment 38, further comprising detecting in chromosome 1 of at least one F2 offspring plant the presence of a homozygous donor brachytic locus from the donor tomato plant.

39. The method according to embodiment 35, further comprising:

a) backcrossing the at least one offspring tomato plant to a recipient non-brachytic tomato plant to produce F2 offspring plants; and b) detecting in chromosome 1 of at least one F2 offspring plant the presence of the donor brachytic locus from the donor tomato plant.

40. The method of any one of embodiments 35-39, wherein the donor brachytic locus comprises all or a portion of SEQ ID NO: 1, SEQ ID NO: 48 or SEQ ID NO: 2 or an ortholog thereof.

41. A method for producing a brachytic and/or early flowering plant, comprising:

a) selecting a plant having at least one br allele;

b) identifying one or more brachytic markers in the brachytic plant; and c) using the one or more brachytic makers to facilitate marker-assisted selection of offspring having the br allele.

42. The method of embodiment 40, wherein identifying the one or more brachytic markers comprises identifying at least two brachytic markers, wherein the at least two brachytic markers flank the br allele.

43. The method of embodiment 41 or 42, wherein the brachytic and/or early flowering plant is a brachytic tomato plant.

44. The method of any one of embodiments 41-43, wherein the brachytic markers comprise a PCR amplification product.

45. The method of embodiment 44, wherein the brachytic markers comprise an amplification product comprising all or a portion of SEQ ID NO: 1, SEQ ID NO: 48, or SEQ ID NO: 2 or an ortholog thereof.

46. The method of any one of embodiments 41-43, wherein the brachytic markers comprise a single nucleotide polymorphism (SNP).

47. The method of embodiment 46, wherein the SNP is selected from the group consisting of brM1, brM2, brM3, brM4, brM5, brM6, brM7, brM8, solcap_18634, solcap_456, and solcap_457.

48. The method of embodiment 43, wherein the brachytic markers are in a continuous nucleic acid region comprising an interval between 74,936,467 and 75,699,595 bp on chromosome 1 of the tomato plant, or is linked, closely linked, tightly linked, or extremely tightly linked to an interval between 74,936,467 and 75,699,595 bp on chromosome 1 of the tomato plant.

49. A method for producing a brachytic and/or early flowering plant, comprising:
a) selecting a donor plant having at least one donor br allele and identifying at least one donor brachytic marker linked to the donor br allele;
b) selecting a recipient plant, wherein the recipient plant optionally has at least one recipient br allele and, if present, identifying at least one recipient brachytic marker linked to the recipient br allele;
c) crossing the donor plant with recipient plant to produce a population of progeny plants;
d) genotyping the progeny plants for the presence or absence of the at least one donor brachytic marker and optionally the at least one recipient brachytic marker; and
e) selecting progeny plants containing the at least one donor brachytic marker and optionally the at least one recipient brachytic marker.

50. The method of embodiment 49, wherein at least two donor brachytic markers and optionally at least two recipient brachytic markers are identified.

51. The method of embodiment 50, wherein the at least two donor brachytic markers flank the donor br allele and the at least two recipient brachytic markers flank the recipient br allele.

52. The method of any of embodiments 49-51, wherein the brachytic and/or early flowering plant is a tomato plant.

53. The method of any of embodiment 49-52, wherein the donor genetic markers and/or recipient genetic markers comprise a PCR amplification product.

54. The method of embodiment 53, wherein the PCR amplification product comprises all or a portion of SEQ ID NO: 1, SEQ ID NO: 48, or SEQ ID NO: 2 or an ortholog thereof.

55. The method of any one of embodiments 49-52, wherein the donor genetic markers and/or recipient genetic markers comprise a single nucleotide polymorphism (SNP).

56. The method of embodiment 55, wherein the SNP is selected from the group consisting of brM1, brM2, brM3, brM4, brM5, brM6, brM7, brM8, solcap_18634, solcap_456, and solcap_457.

57. The method of embodiment 52, wherein the donor genetic markers and/or recipient genetic markers are in a continuous nucleic acid region comprising an interval between 74,936,467 and 75,699,595 bp on chromosome 1 of the tomato plant, or is linked, closely linked, tightly linked, or extremely tightly linked to an interval between 74,936,467 and 75,699,595 bp on chromosome 1 of the tomato plant.

58. The method of any of embodiments 1, 3-5, 8, 10-12, 15-22, 24-26, 41-42, 45-46, 49-51, and 53-55, wherein in the plant is a pepper plant.

59. A method for producing a brachytic Solanaceae plant comprising: (a) isolating one or more nucleic acids from one or more Solanaceae plants; (b) genotyping said one or more nucleic acids for the presence of a brachytic marker wherein the brachytic marker comprises a detectable genetic marker linked, closely linked, tightly linked, or extremely tightly linked to any of SEQ ID NOs: 1-8 and 48 or an ortholog thereof, or a fragment of any of SEQ ID NOs: 1-8 and 48 or an ortholog thereof; (c) selecting a first Solanaceae plant on the basis of the presence of the brachytic marker genotyped in (b); (d) crossing the first Solanaceae plant of (c) with a second Solanaceae plant not having the brachytic marker; (e) collecting seed from the cross of (d); and (f) growing a progeny Solanaceae plant from the seed of (e), wherein said progeny Solanaceae plant comprises in its genome the brachytic marker.

60. A method of introgressing a br allele into a Solanaceae plant comprising: (a) crossing at least donor Solanaceae plant known to have at least one br allele with at least one recipient Solanaceae plant in order to form a segregating population; and (b) screening the segregating population with one or more brachytic markers to determine if one or more Solanaceae plants from said segregating population contains the one or more brachytic markers, the one or more brachytic makers comprising one or more detectable genetic markers linked, closely linked, tightly linked, or extremely tightly linked to any of SEQ ID NOs: 1-8 and 48 or an ortholog thereof, or a fragment of any of SEQ ID NOs: 1-8 and 48 or an ortholog thereof.

61. The method of embodiment 59 or 60, wherein the Solanaceae plant is a tomato plant.

62. The method of embodiment 59 or 60, wherein the brachytic marker comprises a PCR amplification product, a single nucleotide polymorphism (SNP), a restriction fragment length polymorphism (RFLP), an amplified fragment length polymorphism (AFLP), a simple sequence repeat (SSR), a simple sequence length polymorphism (SSLP), an insertion/deletion polymorphism (indel), a variable number tandem repeat (VNTRs), or a random amplified polymorphic DNA (RAPD).

63. The method of embodiment 62, wherein the PCR amplification product comprises all or a portion of SEQ ID NO: 1, SEQ ID NO: 48, or SEQ ID NO: 2 or an ortholog thereof.

64. The method of embodiment 62, wherein the SNP is selected from the group consisting of brM1, brM2, brM3, brM4, brM5, brM6, brM7, brM8, solcap_18634, solcap_456, and solcap_457.

65. The method of embodiment 61, wherein the brachytic marker is in a continuous nucleic acid region comprising an interval between 74,936,467 and 75,699,595 bp on chromosome 1 of the tomato plant, or is linked, closely linked, tightly linked, or extremely tightly linked to an interval between 74,936,467 and 75,699,595 bp on chromosome 1 of the tomato plant.

66 The method of embodiment 60, wherein screening the segregating population comprises amplifying a nucleotide sequence containing the brachytic marker to produce an amplification product, wherein the amplification product is determinative for the presence and/or absence of the brachytic marker.

67. A genetically modified Solanaceae plant wherein a brachytic locus has been genetically modified through the use of a CRISPR/Cas system.

68. A method of genetically modifying a Solanaceae plant, the method comprising: introducing a Cas protein or a nucleic acid encoding the Cas protein and a guide RNA or a nucleic acid encoding the guide RNA into a plant cell, wherein the guide RNA and Cas protein form a complex that targets the brachytic locus.

69. A Solanaceae plant that has been genetically modified at the brachytic locus, wherein said brachytic locus has been modified by expressing a CRISPR/Cas9 nuclease capable of targeting a sequence within brachytic locus.

70. A genetically modified Solanaceae plant having a brachytic phenotype, wherein the genetic modification is specifically targeted at the brachytic locus, wherein the genetic modification at the brachytic locus is achieved by introducing a CRISPR/Cas system.

71. The method of embodiments 68 wherein the guide RNA contains a guide sequence comprising a 17-20 nucleotide sequence comprising 17-20 contiguous nucleotides from SEQ ID NO: 64 or a complement thereof.

72. The method of embodiments 71 wherein the CRISPR/Cas construct contains a guide sequence comprising a 17-20 nucleotide sequence comprising 17-20 contiguous nucleotides from SEQ ID NO: 49 or a complement thereof.

H. Sequences

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 1

Sequences

SEQ ID NO: 1 Brachytic
gatgttgttatgttttttgtagaggaaaggtgaatgagaatgttttttgtatgtgtttgtagtttatgatgagat
ggtttggatgtaagagggtgtgaggggtttatatagagggttttggatgcttacaattatattgtgtgagtttga
tagaggtcttaaagtggatagtggggtagtctcccccgttctggcatctttagaatttcgagattcaaacgagt
atttttttatcacgattaattatatattttgtattattttaaataatctgttacagtaatttatagcagttttta
cataatttctatatatactaattttatctcaaaaatttgtgtgtatgaatacacaagaaaaatcaaaaagtttaa
tttctgaaaaacaaattatattgcataaattgaaataaagaaaataattttaaggttaattattaccacttaaat
atgttgatagtgaagaaaattctttacgtttagaatgtgtgtatcaaaattgtgtagcaagtgaaaagttttgag
gggtattttacaactaatgtacgagaagattgtaggagaaacatattcttgtacccttaaagaatataatatacc
cttgttactattatcaaagtggacgaatatgacattttgtttgcatatataagtgatgaaaatttcccaacttta
taaggacgttgttcatgaaagcaaaaaattaaaattataaaattttaccatcaaaggaaataagattattggagt
aaaaagtgtatatatatatatatatattgattattgatcatgcaagtagagaattgacacgtgtttgagaacatt SEQ ID NO: 2 Solyc01g066980.2ch01_75108781
gatataaggaattcttgttttttttattttttttattttttgaaaaaggatgagccttcttgggatgcgtgcacttt
cgaagtcattaaagtcgaataagaagaaagaaatatcttcgtcattttgtttcttcttaaaacaagctacgaaaa
agtttttgaggttataagtttcagagtattaattttttatagtattagagtaattcaacatttataaaaggtcaat
actaaattagatatctataattacattttgattcattgacttaatgatataaatatgtgtacatagattttaagc
gcaaaaggaaaaatattttgtggaataagcactcttatatatatatatatcatataataaaacacattcacttgt
aataatatacaacattcccctcttcaacttcccaaattacaaccttagcaaccttgtgaaacaaatcacaaat
taaacgatagaaacttaattacaacacacttgaccaaaaaaaagcaaaaaaaagaaaaaaaaacacattcaaatg
atcaactccttccctttttcccccatattttgtttacatatctctaacctcaaattcattgcgattcttgacga
cgatatcgaacatatgcatggatttgaacctgttgaaatcctttggtagagaaataagatgaacggttgatcttt
tgtggtattgaagaagttcaggttcatcatagtacctctcccatccaagagagtacagtttcctttcaagtactg
catatgatgtgatgacttcattactaggaagatgtacaagaacttttcggagtccgttcgccccgtggcaatcgg
agttctccactagacggacaacaccattcttgaatacccaaactccagacatgattgttgaagatgttgttatgt
tttttgtagaggaaaggtgaatgagaatgttttttgtatgtgtttgtagtttatgatgagatggttggatgtaa
gagggtgtgaggggtttatatagagggttttggatgcttacaattatattgtgtgagtttgatagaggtcttaaa
gtggatagtggggtagtctcccccgttctggcatctttagaatttcgagattcaaacgagtattttttatcac
gattaattatatattttgtattattttaaataatctgttacagtaatttatagcagtttttacataatttctata
tatactaattttatctcaaaaatttgtgtgtatgaatacacaagaaaaatcaaaaagttttaatttctgaaaaaca
aattatattgcataaattgaaataaagaaaataattttaaggttaattattaccacttaaatatgttgatagtga
agaaaattctttacgtttagaatgtgtgtatcaaaattgtgtagcaagtgaaaagttttgaggggtattttacaa
ctaatgtacgagaagattgtaggagaaacatattcttgtacccttaaagaatataatataccttgttactatta
tcaaagtggacgaatatgacattttgtttgcatatataagtgatgaaaatttcccaacttataaggacgttgtt
catgaaagcaaaaaattaaaattataaaattttaccatcaaaggaaataagattattggagtaaaaagtgtatat
atatatatatattgattattgatcatgcaagtagagaattgacacgtgtttgagaacatt SEQ ID NO: 3 Solyc01g066950.1ch01_75049083
tatatatatatattcttgacatcttactttattttttttaaaacagtgaagaattcgaatttgaggtaaagccttt
gaatttatagtcaaagacttcttgatgaaataaatgggaaaataccattttgtctttattcaaaataagaccaaa
aaaaaagagaaaagaaaagatatttccataaaaaaaatatatcaatcacatatccacctatcatcgttggctt
aatgataaaaatataatctggtttgacttgatacaaaatttaagtaaataaagaagacttttaaatatatatatg
actaaaaatttaagtatttgatagtacaaatttatttaagtatatagataaaagtttcgaagcgaaaccaagttt
tattgccataaacttcactcttacacaccattacaacaagtaataattagcttcctcacccaaaagaaactaaaa
cacccccccttttgacctaaattacacaaaccaaaccttaagttaaaagaagaaacaacctaatttaaattaaacaa
cattaattaatttgagaaaaatctcaaatcaactaatgattattagtaatactacatatccctaacagcaaactc
attacgattcttaacaacaatatcatacatgtgcatggacctgaggttgttgaagtcgtttggtagagaaataag
atgaacagttgatcttttatggtactgaagaaggtcagggtcatcatagtacctctcccatccaagagagtacag
tttcctttcaagtactgcatatgatgttattacttcattactagaaaggtgcacaagcactttacgacgacccgt
cgcaccgtgaaagtcaccgaggttctcaactagcctcactactccattcttgattttccaaacaccagacatgtt
tcaaaaaatatgaatatgaaactgagtgagtgattgtgtgtgagtttgaagataagtgtgaagggttttat
acgggttctatgtaataaaaaatacattaggtggcaaaaagtattttctttcttatttaataaaattgatgatg
attaataggtaggatttagaattatactaacttatcgtacgctcataagattaaagaaaaagaaagggagaatat
ttatatggccacaagataccctaatttacctgtcacgacccaaaacggaccgcgagtggcacccacatttatctt
cctatgtgagcgaaccaaccaatctaaacccaacattttcaatataatgacggaatataatgcggaagacttaacc
tcattaatgaaaatcaattaaataacttctaaaaactcaacaactattattatccccaaaatctggaagtcatca TABLE 1-continued Sequences tcataagaacatctatcctcaaattactaaagctaagagtatctagaaagctagaataaataaaagctagttcat
gccggaacttcaaggcatcgagacatgaagaagaagatccagtccaagctagaagcgttagctcaccctgaaatc
cggtgtaatgaagatcggctagagttgcggttgagttaaagacgacggcacgtttgctgcactccacaaataaca
aggaaagaaacatacaagtaggggtcagtacaaaacacgatcatcggccaactcaaaatagaaagcaatatatat
caagtaataatatgaaatcaactacattactcaacatgtagcaacaacaagtactatgatcgttaataagtaccg SEQ ID NO: 4 Solyc01g066970.2ch01_75101399
tgcctcacaaattaaaattttttcaaatatcattaaccagatttaataaagcagaatttgtaattgaaaagtagcg
ctaaattaattacgtggaaagctaaagttaaaatgtaaccaaaaaaaagtcattcttttatataaaaaaaaaaa
ctaaaaaggaaagaagattattcttttttaaacggggaaaaaaaaaactaaaaaggaaagaagattattcttttt
taaacggggaagtatatatatatatatatatatatatatatatatatatatatatatatatatatgcgcgtgt
gtgagagactcaaaattgaagtatttgatagtaagaaatttatttcagtatatagataaaattttcaagccaaacc
aagttttttttattgccataaaacttcactcttacacacaattacaagtaataattagcttcctcacccaaaagaa
actaaaacaccccccttaaacctaaattacacaaaccaaacattaagttaaaacaagaaacaacctaatttaaat
caaacaacattaattaatttgagaaaaatatctcaaatcaattattaattagtagtactacatatccctaa
ctgtaaactcattacgattcttaacaacaatatcatacatgtgcatggacttgaggttgttgaagtcctttggta
gagaaataagatgaacagttgatcttttatggaattgaagaaggtcagggtcatcatagtacctctcccatccaa
gagagtacagtttcctttcaagtactgcatatgatgttattacttcattactagaaaggtgcacaagcactttac
gacgaccgtcgcaccgtggaagtcaccgggggttctcaactagcctcactactccattcttgaatacccaaacac
cagacatgtttcaaaaaatatatgaatatgaaaatagtaagtgagtattgtgtgtgagtttgaacataagtgtga
gtgggtttttataggggtttctatgtagtgtgtaataaaaaaaatacataaggtggcaaaaagtaatcttttttct
tatttaataaaattgataataggtaggattttggaatgtggctgcttataggatttagaaatatactaacttatc
gtacgtttattaagattaaagaaaaagaaagggagaatatttaaatggccacaagatgccctaatttgccctact
gaaattagaatcttctcctaaacaatcactaattaatgatcttatgctcataagatgaacctaattctttttggtt
aatgggttccaagcataattctttaattttttttagtgctaagaacaatcttctattcttatatccattgcttgat
cagcccttcacaaaaggaagaattaaataaattaaaagatatttcggggaagattaatttgtcccatctcatgt
tgatgatgtttcttttaatccttaattaatgtctaataacaattttttttttaaaaaaaaaaaattactccaaatc
aatgagaaatttgtgttatgatacgtgatattcccaccccatttcctatttaactaggtcaataaaaacgtatggt
gagaaacaaattctcactaaaataccaagagtttttttttttttaattttgttgtgtaatttaaacattagtgtgag
tatagccactggacatttttcaataggaaaatttcaatgggatagtgtctgttccaatttgtttatctagttttta
gtttgaca SEQ ID NO: 5 Solyc01g066980 in brachytic plant
catctcatcataaactacaaacacatacaaaaaacattctcattcacctttcctctacaaaaaacataacaacat
c SEQ ID NO: 6 Solyc01g066980 in normal plant
catctcatcataaactacaaacacatacaaaaaacattctcattcacctttcctctacaaaaaacataacaacat
cttcaacaatcatgtctggagtttgggtattcaagaatggtgttgtccgtctagtggagaactccgattgccacg
gggcgaacggactccgaaaagttcttgtacatcttcctagtaggtcatcacatcatatgcagtactttgaaa
ggaaactgtactctcttggatgggagaggtactatgatgaacctgaacttcttcaataccacaaaagatcaaccg
ttcatcttatttctctaccaaaggatttcaacaggttcaaatccatgcatatgttcgatatcgtcgtcaagaatc
gcaatgaatttgaggttagagatatgtaaacaaaatatgggggaaaaaagggaaggagttgatcatttgaatgtg
tttttttttctttttttgctttttttttggtcaagtgtgttgtaattaagttctatcgtttaatttgtgatttg
tttcacaatgttgctaaggttgtaaagttgtaagaggggaaatgttgtatattattacaagtgaatgt
gttttattatatgatatatatatatataagag SEQ ID NO: 7 Solyc01g066950 in normal plant
atgtctggtgtttggaaaatcaagaatggagtagtgaggctagttgagaaccctcggtgactttcacggtgcgacg
ggtcgtcgtaaagtgctctgtgcaccttctagtaatgaagtaataacatcatatgcagtacttgaaaggaaactg
tactctcttggatgggagaggtactatgatgaccctgaccttcttcagtaccataaaagatcaactgttcatctt
atttctctaccaaacgacttcaacaacctcaggtccatgcacatgtatgatattgttgttaagaatcgtaatgag
tttgctgttagggatatgtag SEQ ID NO: 8 Solyc01g066970 in normal plant
ctcacacacaatactcacttactattttcatattcatatattttttgaaacatgtctggtgtttgggtattcaag
aatggagtagtgaggctagttgagaaccccggtgacttccacggtgcgacgggtcgtcgtaaagtgcttgtgcac
ctttctagtaatgaagtaataacatcatatgcagtacttgaaaggaaactgtactctcttggatgggagaggtac
tatgatgaccctgaccttcttcaattccataaaagatcaactgttcatcttatttctctaccaaaggacttcaac
aacctcaagtccatgcacatgtatgatattgttgttaagaatcgtaatgagtttacagttagggatatgtagtac
tactaattaataattagttgatttgagatattttctcaaattaatttagagatatttttgatttaaattaggttgtt
tcttgtttaacttaatgtttggtttgtgtaattaggtttaagggggggtgtttttagtttctttttgggtgaggaa
gctaattattacttgtaattgtgtaagagtgaagttttatggcaataaaaaaacttggtttggcttgaaaatt
ttatct SEQ ID NO: 48 Brachytic
gatataaggaattcttgttttttttatttttttattttttgaaaaaggatgagccttcttgggatgcgtgcacttt
cgaagtcattaaagtcgaataagaagaaagaaatatcttcgtcattttgtttcttcttaaaacaagctacgaaaa
agtttttgaggttataagttcagagtatttaattttttatagtattagagtaattcaacatttataaaaggtcaat
actaaattagatatctataattacattttgattcattgacttaatgatataaagatgttgttatgttttttgtag
aggaaaggtgaatgagaatgtttttgtatgtgtttgtagtttatgatgagatggtttggatgtaagagggtgtg
aggggtttatatagagggttttggatgcttacaattatattgtgtgagtttgatagaggtcttaaagtggatagt
ggggtagtctccccgtttctggcatctcttagaatttcgagattcaaacgagtatttttttatcacgattaatta
tatattttgtattttaaataatctgttacagtaatttatagcagttttttacataatttctatatatactaat
tttatctcaaaaatttgtgtgtatgaatacacaagaaaaatcaaaaagtttaattctgaaaaacaaattatatt
gcataaattgaaataaagaaaataattttaaggttaattattaccacttaaatatgttgatagtgaagaaaattc
tttacgtttagaatgtgtgtatcaaaattgtgtagcaagtgaaaagttttgagggtattttacaactaatgtac
gagaagattgtaggagaaacatattcttgtaccccttaaagaatataatataccctgttactattatcaaagtgg TABLE 1-continued Sequences acgaatatgacattttgtttgcatatataagtgatgaaaatttcccaactttataaggacgttgttcatgaaagc
aaaaaattaaaattataaaattttaccatcaaaggaaataagattattggagtaaaaagtgtatatatatata
tatattgattattgatcatgcaagtagagaattgacacgtgtttgagaacatt

TABLE 2

Primers

| SEQ ID NO. | Description and sequence |
|---|---|

66980 marker

SEQ ID NO: 9   Forward: 5'-aaaggatgagccttcttggg-3'
SEQ ID NO: 10  Reverse: 5'-ccactatccactttaagacctct
               atc-3'

RS041917m: SL2.50ch01: 75268297 . . 75268341 bp

SEQ ID NO: 11  Forward: 5'-aaacacttccagtcagta-3'
SEQ ID NO: 12  Reverse: 5'-ttgttgacaatctaaggaag-3'

CGH-75.29: SL3.0ch01: 75,102,363-75,110,048 bp

SEQ ID NO: 13  Forward: 5'-cttgggatgcgtgcactttc-3'
SEQ ID NO: 14  Forward-1: 5'-gaactttcggagtccgttc
               g-3'
SEQ ID NO: 15  Reverse: 5'-accccctcacaccctcttaca-3'

RS041917t: SL2.50ch01: 75314323 . . 75314373 bp

SEQ ID NO: 16  Forward: 5'-tcaaaactcaaataacaagaat
               g-3'
SEQ ID NO: 17  Reverse: 5'-tcatgaataggcaccaataa-3'

RS041917u: SL2.50ch01: 75360405 . . . 75360472 bp

SEQ ID NO: 18  Forward: 5'-ggatttcaaagtcatgacaa-3'
SEQ ID NO: 19  Reverse: 5'-tacgtacatgtggcattt-3'

RS041917h: SL3.00ch01: 74990561 . . .
74990619, 74990589

SEQ ID NO: 20  Forward: 5'-tcaaattttagacctctaagta
               aaa-3'
SEQ ID NO: 21  Reverse: 5'-gtcgtggctaaacttaattc-3'

RS041917k: SL3.00ch01: 75067607 . . .
75067663, 75067637

SEQ ID NO: 22  Forward: 5'-aagaagctcgagaactaattt-3'
SEQ ID NO: 23  Reverse: 5'-ccattgtggacactcaattt-3'

RS041917w: SL3.00ch01: 75306037 . . .
75306088, 75306058

SEQ ID NO: 24  Forward: 5'-tgtcacagtgaacatgtatt-3'
SEQ ID NO: 25  Reverse: 5'-cttgatgaattgactttcaaat
               g-3'

RS041917x: SL3.00ch01: 75351329 . . .
75351395, 75351358

SEQ ID NO: 26  Forward: 5'-cccttgttatttaacattgatt
               t-3'
SEQ ID NO: 27  Reverse: 5'-gcagtaataaagatctgaaca
               a-3'

RS041917y: SL3.00ch01: 75516627 . . .
75516727, 75516692

SEQ ID NO: 28  Forward: 5'-gtgtttctaacattcaagca-3'
SEQ ID NO: 29  Reverse: 5'-tcaaattgtcctgtgcaa-3'

TABLE 2-continued

Primers

| SEQ ID NO. | Description and sequence |
|---|---|

RS041917z: SL3.00ch01: 75531402 . . .
75531471, 75531427

SEQ ID NO: 30  Forward: 5'-ggataaagattctccaggtt-3'
SEQ ID NO: 31  Reverse: 5'-ttgagctcatcatgcta-3'

The following examples are provided to illustrate certain particular features and/or embodiments. These examples should not be construed to limit the disclosure to the particular features or embodiments described.

EXAMPLES

Example 1. Population Development

Three populations used to fine map the br locus were developed from crosses between: a) Fla. 8044 and Fla. 8834, b) Fla. 8624 and Fla. 8834, and c) Fla. 8044 and Fla. 8916. Fla. 8834 and Fla. 8916 are large-fruited, determinate (sp/sp; homozygous at the self-pruning locus) inbred lines, and each carries the br derived from the inbred line, NC 13G-1. The br allele in NC 13G-1 is derived from the BHN inbred line, 823125-1-3 and originated from E. C. Tigchelaar's breeding program at Purdue University (Gardner, 2000). Fla. 8044 and Fla. 8624 are large-fruited, determinate inbred lines that do not carry the br allele. All Florida (Fla.) lines and populations were developed and maintained by the University of Florida Institute of Food and Agricultural Sciences (UF/IFAS) tomato breeding program (Wimauma, Fla.).

Example 2. Tomato Array

To screen $F_2$ selections from the Fla. 8044×Fla. 8834 population, the tomato Illumina Infinium array initiated by the Solanaceae Coordinated Agricultural Project (SolCAP) (hereafter, tomato array) was used as described by Sim et al. (Sim S C et al. 2012. Development of a large SNP genotyping array and generation of high-density genetic maps in tomato. PLoS One 7:e40563). Of the 7720 markers included in the array, 7509 of these showed clear genotype calls for the parents and $F_2$ selections, and these were used for further analysis. Single nucleotide polymorphisms (SNPs) shown to be polymorphic between the br phenotype (described in 'Phenotype analysis' section below) vs. normal, were used for fine mapping. SNPs from the tomato array that were significantly associated with the br phenotype were identified by calculating a P-value using Fisher's exact test and then applying the Bonferroni correction (alpha level 0.05) on P-values obtained for each marker position.

Example. 3 Sequencing

Whole genome sequencing (WGS) of three lines (Fla. 8916 with the br and both Fla. 8044 and Fla. 8624 without the br) was conducted using Illumina technology as described previously (Lee, T. G., R. Shekasteband, and S. F. Hutton. 2018. Molecular markers to select for the j–2-mediated jointless pedicel in tomato. HortScience 53:153-158.). For each line, the approach described by Lee et al. (2018) was used to identify SNPs compared with the Heinz 1706 reference genome assembly.

Example 4. Molecular Marker Analysis

Cleaved amplified polymorphic sequences (CAPS), derived CAPS (dCAPS) and high resolution DNA melting analysis (HRM) markers for fine mapping were designed using SNP data obtained by the tomato array genotyping and by WGS. Marker development was conducted as described by Lee et al. (2018). The primer sequences of markers are shown on Table 3. Parental lines Fla. 8044, Fla. 8624, Fla. 8834 and Fla. 8916 were included as controls for genotyping.

Nucleotide sequence polymorphisms obtained from the tomato array and WGS of tomato lines with and without br provided resources to saturate near the br region in populations with different genetic backgrounds. The whole genome sequencing data in particular, provided the advantage of no ascertainment bias from the analyzed region around the br.ABundant sequence resources close to the locus enabled identification of recombination sites which were necessary to perform fine mapping. All physical positions of molecular markers used in this study were aligned to the most recent tomato genome assembly (SL3.0; International Tomato Genome Sequencing, Current Tomato Genome version SL3.0 and Annotation ITAG3.10 Project https://solgenomics.net/organism/*Solanum*_lycopersicum/genome).

TABLE 3

Molecular markers used for fine mapping br on tomato chromosome 1.

| Marker | Marker type[a] | Position[b] | SNP identification[c] | Sequence polymorphism | SEQ ID NO. | Strand | 5'-3' sequence | Size of PCR amplicon (bp)[d] |
|---|---|---|---|---|---|---|---|---|
| brM1 | dCAPS | 74,454,291 | Array | G\|C[e] | 32 | Forward | ccacattttttattagattacccagaatatct | 133, 100 + 33 (Taq1) |
| | | | | | 33 | Reverse | gccctgggttttttgg tttt | |
| brM2 | HRM | 74,578,849 | WGS | G\|A | 34 | Forward | atacttgttgttgggc agggg | 99, 99 |
| | | | | | 35 | Reverse | ccataaattgttgtcc actcatcca | |
| brM3 | CAPS | 74,806,803 | WGS | G\|A | 36 | Forward | agccattatgttgtac ctgtca | 162, 87 + 57 (Hpy188I) |
| | | | | | 37 | Reverse | tgggtttggatgggtt cagg | |
| brM4 | CAPS | 74,936,467 | Array | C\|A | 38 | Forward | tcttctttttcttagc tcctccacc | 219 + 137 (DpnII), 180 + 137 + 39 (DpnII) |
| | | | | | 39 | Reverse | aaatgttgaagctgaa actttg | |
| brM5 | HRM | 75,067,639 | WGS | A\|G | 40 | Forward | aagaagctcgagaact aattt | 58, 58 |
| | | | | | 41 | Reverse | ccattgtggacactca attt | |
| brM6 | dCAPS | 75,655,879 | Array | A\|C | 42 | Forward | tcccactcaaggtaaa tgtcta | 261, 242 + 19 (XbaI) |
| | | | | | 43 | Reverse | aggaatgggtgtatca acaactg | |
| brM7 | HRM | 75,699,595 | WGS | G\|A | 44 | Forward | cccaacccacgaata gagg | 136, 136 |
| | | | | | 45 | Reverse | gacctggggcctaact caac | |
| brM8 | HRM | 76,849,813 | WGS | A\|C | 46 | Forward | gactgcagtatccttc cgca | 87, 87 |
| | | | | | 47 | Reverse | gatgctaggacagcca tgtga | |

[a]dCAPS, derived cleaved amplified polymorphic sequences; CAPS, cleaved amplified polymorphic sequences; HRM, high-resolution DNA melting analysis
[b]SNP positions are given on chromosome 1 in the SL3.0 version of the Heinz 1706 genome assembly
[c]Array, the tomato illumina array that is initiated by the Solanaceae Coordinated Agricultural Project (SolCAP); WGS, whole genome sequencing
[d]normal genotype, brachytic; obtained two or more fragments subjected to restriction enzyme in the brachytic genotype
[e]normal genotype|brachytic

Example 5. Phenotype Analysis

All phenotypic data were collected at the UF Gulf Coast Research and Education Center, Wimauma, Fla. Seed was sown directly into peat-lite soilless media (Speedling, Sun City, Fla.) in 128-cell SPEEDLING® trays (38 cm$^3$ cell size; Speedling). Seedlings were grown in a greenhouse and fertilized weekly with a 1 g·L$^{-1}$ solution of a 20-20-20 water soluble fertilizer. Young plants were transplanted to field beds six weeks after sowing. Field beds were 20 cm high and 81 cm wide and had been fumigated with a combination of chloropicrin and 1, 3-dichloropropene (Pic-Clor 60 EC at 300 lbs per treated acre; Soil chemical corporation, Hollister, Calif.) and covered with reflective plastic mulch. Beds were spaced 152 cm apart, and young plants were planted in a single row within each bed at 46 cm in-row plant spacing. Irrigation was applied through drip tape beneath the plastic mulch of each bed. A recommended fertilizer and pesticide program was followed throughout the growing season (Freeman, J. H., E. J. McAvoy, N. S. Boyd, P. J. Dittmar, M. Ozores-Hampton, H. A. Smith, G. E. Vallad, and S. E. Webb. 2015. Vegetable Production Handbook of Florida 2015-2016. In: Freeman J H, Dittmar P J, Vallad G E (ed) Tomato Production, pp 211-234.).

To select for phenotypes mediated by br in the young plant stage, visual screening was used. Plant height was considered as the br-mediated phenotype. As the br and its associated phenotypes have been characterized as incomplete dominance (Gardner, R. G. and J. M. Davis. 1991. Evaluation of a fresh-market tomato breeding line with brachytic and prostrate growth habits. HortScience 26:713. (Abstr.); tall, intermediate, and short plants were considered to be the expression of homozygous normal allele, heterozygous allele and homozygous br allele (homozygous br-mediated phenotype; also termed herein as br phenotype), respectively.

Plants in populations from a cross between Fla. 8624 and Fla. 8834 were collected six weeks after sowing. We measured the distance between the cotyledonary node and the terminal axillary bud on the main stem of each plant as analogous to plant height. Phenotype results were analyzed for statistical significance by one-way analysis of variance (ANOVA) in conjunction with a two-tailed Tukey multiple comparison test or the two-tailed t-test. The 95% confidence intervals were calculated to give error bars. Additionally, all plant samples phenotyped were genotyped using an HRM marker brM5 (Table 3).

A trait refers to a phenotype by the expression of a gene. Habit, as used herein, is a combined variation of phenotypes. A habit by derive from two or more traits. As used herein, shortened internode and shortened height may be used interchangeably. Shortened internodes drive shortened stem length/plant height based on independent tomato genetics studies, but the term shortened internodes is preferred to be aware of being distinguishable from the dwarf-mediated phenotype (all parts foreshortened).

Validation of the Visual Screening Approach for Br Phenotype in Young Plants.

The validity of the visual screening approach was supported by the significant differences in plant height observed in a greenhouse experiment. A population was produced from the cross between Fla. 8624 (normal allele) and Fla. 8834 (homozygous br). The height of $F_1$ plants were measured and compared to that of parental lines (FIG. 1a, left). Plant heights with (either homozygous br or heterozygous) or without br (homozygous normal) were distinguishable (FIG. 1a, right; FIG. 1c). Similarly, 150 $F_2$ plants from this population were also measured for plant height, and statistical significance among genotypes was observed in all comparisons (FIG. 1b). These results support the visual screening approach as a method to detect phenotypic differences in young plants stage.

Example 6. Mapping the Br Locus in Tomato Plants

Parents and 16 $F_2$ plants from the Fla. 8044 (normal)×Fla. 8834 (br) population were selectively genotyped using the tomato array. Selections were based on plant height of 6-week old plants as described in 'Phenotype analysis' section above. Selected plants included eight shorter individuals with the br phenotype, and eight taller individuals with normal phenotype. br was mapped in classical genetic studies and SNP's identified from the parents and $F_2$ plants.

Mapping of br was initiated by genotyping 16 $F_2$ plants (eight for the br phenotype and eight for normal as described in 'Phenotype analysis' section above) from the cross between Fla. 8044 and Fla. 8834. Plant samples were genotyped as 'Tomato array'. From this analysis, SNPs shown to be polymorphic between the br phenotype and normal were identified. SNPs that span approximately 1.2-Mbp interval in the distal part (within 90% of the chromosome length) on chromosome 1 were statistically significant for phenotypic difference (Table 4). The relative physical positions of such SNPs, which represent evidence of the introgression of br to a normal phenotype line, were consistent with genetic locations of markers used to map br in classical genetic maps (MacArthur, J. W. 1931. Linkage studies with the tomato. III Fifteen factors in six groups. Roy. Canad. Inst. Trans. 18:1-19; Balint-Kurti, P. J., D. A. Jones, and J. D. Jones. 1995. Integration of the classical and RFLP linkage maps of the short arm of tomato chromosome 1. Theor. Appl. Genet. 90:17-26.). Thus, the position of br was further delineated on this genomic interval.

B) Fine mapping of the br locus performed on the Fla. 8624 (normal)×Fla. 8834 (br) population. From 1260 $F_2$ plants that were genotyped using molecular markers brM1, brM4 and brM6 (Table 3), 17 recombinants were identified and advanced by self-pollination. For each of the selected $F_2$ plants, 48 progeny were genotyped with markers brM2, brM3, brM4, brM5, brM7 and brM8, and plants homozygous for the recombinant haplotype were selected as $F_3$ recombinant inbred lines (RILs). Six plants per $F_3$ RIL were planted to the field and evaluated at maturity for plant phenotype (FIG. 1d), and $F_4$ seed was harvested from a single plant of each line. Phenotypes were confirmed in $F_4$ RILs by evaluating 64 plants per RIL at transplant stage and six plants per RIL in the field. Fla. 8624 and Fla. 8834 were included as controls in all phenotype screens.

In the stage of fine mapping, 1260 $F_2$ plants from the Fla. 8624×Fla. 8834 were screened to identify recombinants with markers brM1, brM4 and brM6, which flank the br interval as mapped by tomato array. From this screening, 17 recombinants were selected. The $F_3$ progeny from the selected $F_2$, identified as fixed for either the homozygous br or normal alleles and showed no progeny segregation in $F_4$, were tested for association between phenotype and the segregation of markers (Table 5). Genetic markers were used to map the regions of crossover events in each selected RIL. Crossovers among the RILs corresponded to three sites within a 2.2-Mbp interval between the flanking markers brM2 and brM8. The upper position of the br shown in Table 5 was determined by a recombinant line RIL1-4 with the br phenotype. The line was fixed for the marker allele from the normal parent for brM4 and the region above it and from the br parent for brM5 and the markers below it. The lower limit of the br locus was defined through the testing of lines RIL1-7, RIL1-8, RIL1-9, RIL1-10, RIL1-11 and RIL1-12 with the br phenotype. A recombination breakpoint was identified between brM5 and brM7 in those lines. All plants were fixed for the marker allele from the br parent for brM5 and markers above it. These results position br to a 763.1-kb interval between 74,936,467 and 75,699,595 bp. Seven of 17 recombination events in the Fla. 8624×Fla. 8834 population, demonstrated the mapping of br to a 763.1-kb region between molecular markers brM5 and brM7 on chromosome 1.

C) The fine mapped br interval was confirmed by a similar approach using the Fla. 8044 (normal)×Fla. 8916 (br) population. Screening of 662 $F_2$ plants identified nine recombinants within the marker interval spanning the interval between two markers brM2 and brM8. $F_3$ and $F_4$ RILs for each of these were evaluated to determine plant habit, and RILs were genotyped with similar markers to saturate the br locus interval.

Fine mapping of br was confirmed using an independent population derived from a cross between Fla. 8044×Fla. 8916. The mapping procedure began by screening $F_2$ plants from the cross with markers brM2 and brM8. Further screening from the population was completed using the same markers used in the previous cross Fla. 8624 and Fla. 8834. Results from the association between phenotype and the segregation of markers showed the same br interval between brM4 and brM7 as that was identified in the Fla. 8624×Fla. 8834 (Table 6).

Fine mapping of br to the 763.1-kb region between molecular markers brM5 and brM7 on chromosome 1 was confirmed by seven recombination events identified in the population Fla. 8044×Fla. 8916.

TABLE 4

Mapping the br on chromosome 1 using the tomato array

| Marker identity[a] | Physical Position on Chr. 1 (bp)[b] | br phenotype | | | | | | | | |
|---|---|---|---|---|---|---|---|---|---|---|
| | | Fla. 8834 | F2-1[d] | F2-2 | F2-3 | F2-4 | F2-5 | F2-6 | F2-7 | F2-8 |
| solcap__38764 | 69,932,451 | A[e] | A | A | A | A | A | A | A | A |
| solcap__18641 | 72,104,520 | T | T | T | T | T | T | T | T | T |
| solcap__18635 (brM1) | 74,454,291 | T | T | T | T | T | T | T | T | T |
| solcap__18634 | 74,789,884 | A | A | A | A | A | A | A | A | A |
| solcap__18627 (brM4) | 74,936,467 | A | A | A | A | A | A | A | A | A |
| solcap__18619 (brM6) | 75,655,879 | G | G | G | G | G | G | G | G | G |
| solcap__456 | 78,440,321 | T | T | T | T | T | K | T | T | T |
| solcap__457 | 78,535,986 | G | G | G | G | G | R | R | G | G |
| solcap__531 | 80,367,028 | G | A | R | A | A | G | R | R | R |
| solcap__38356 | 80,397,304 | T | T | T | T | T | T | T | T | T |
| solcap__535 | 80,491,145 | G | C | S | C | C | G | S | S | S |
| solcap__25960 | 80,491,686 | G | G | G | G | G | G | G | G | G |

| Marker identity[a] | normal phenotype | | | | | | | | | |
|---|---|---|---|---|---|---|---|---|---|---|
| | Fla. 8044 | F2-9 | F2-10 | F2-11 | F2-12 | F2-13 | F2-14 | F2-15 | F2-16 | p-value[c] |
| solcap__38764 | A | A | A | A | A | A | A | A | A | n/a |
| solcap__18641 | T | T | T | T | T | T | T | T | T | n/a |
| solcap__18635 (brM1) | C | C | C | C | C | C | C | C | Y | <0.05 |
| solcap__18634 | T | T | T | T | T | T | T | T | W | <0.05 |
| solcap__18627 (brM4) | C | C | C | C | C | C | C | C | — | <0.05 |
| solcap__18619 (brM6) | T | T | T | T | T | T | T | T | K | <0.05 |
| solcap__456 | G | G | G | G | G | K | G | G | K | >0.05 |
| solcap__457 | A | A | A | A | A | R | A | A | R | >0.05 |
| solcap__531 | G | G | G | G | G | R | G | G | R | >0.05 |
| solcap__38356 | T | T | T | T | T | T | T | T | T | n/a |
| solcap__535 | G | G | G | G | G | S | G | G | S | >0.05 |
| solcap__25960 | G | G | G | G | G | G | G | G | G | n/a |

[a] Marker identity implemented in the tomato Illumina Infinium array platform (SolCAP, Solanaceae Coordinated Agricultural Project) was abbreviated with the prefix solcap__. Markers in approximately 5 Mb region surrounding SNP positions where statistical significance between different phenotypes was observed are shown
[b] The corresponding chromosome positions for the marker on the SL3.0 version of the genome assembly are from https://solgenomics.net
[c] Significant values of array data were determined by calculating a P-value using Fisher's exact test and then applying the Bonferroni correction (alpha level 0.05) on P-values obtained for each marker position; n/a means no difference between the br phenotype and normal in the test
[d] The population was developed from a cross between Fla. 8834 and Fla. 8044
[e] International Union of Pure and Applied Chemistry nucleotide code. "—" represents missing genotypes
[f] The arrows pointed in the direction that the br is located

TABLE 5

Fine mapping the br in the population Fla. 8624 × Fla. 8834

| Marker | Position on Chr. 1 (bp)[a] | Selected lines | | | | | | | | | |
|---|---|---|---|---|---|---|---|---|---|---|---|
| | | RIL1-1[b] | RIL1-2 | RIL1-3 | RIL1-4 | RIL1-5 | RIL1-6 | RIL1-7 | RIL1-8 | RIL1-9 | RIL1-10 |
| brM2 | 74,578,850 | 0[c] | 0 | 0 | 0 | 0 | 0 | 2 | 2 | 2 | 2 |
| | | | | | | ▼[d] | ▼ | | | | |
| brM3 | 74,806,803 | 0 | 0 | 0 | 0 | 2 | 2 | 2 | 2 | 2 | 2 |
| brM4 | 74,936,467 | 0 | 0 | 0 | 0 | 2 | 2 | 2 | 2 | 2 | 2 |
| | | | | | ▼ | | | | | | |
| brM5 | 75,067,639 | 0 | 0 | 0 | 2 | 2 | 2 | 2 | 2 | 2 | 2 |
| | | ▲ | ▲ | ▲ | | | | ▲ | ▲ | ▲ | ▲ |
| brM7 | 75,699,595 | 2 | 2 | 2 | 2 | 2 | 2 | 0 | 0 | 0 | 0 |
| brM8 | 76,849,813 | 2 | 2 | 2 | 2 | 2 | 2 | 0 | 0 | 0 | 0 |
| Recombination site | | 1 | 1 | 1 | 2 | 3 | 3 | 4 | 4 | 4 | 4 |
| Phenotype[e] | | N | N | N | B | B | B | B | B | B | B |
| Number of tested plants[f] | | 6 | 6 | 6 | 6 | 6 | 6 | 6 | 6 | 6 | 6 |

| Marker | Selected lines | | | | | | | | |
|---|---|---|---|---|---|---|---|---|---|
| | RIL1-11 | RIL1-12 | RIL1-13 | RIL1-14 | RIL1-15 | RIL1-16 | RIL1-17 | Fla. 8624 | Fla. 8834 |
| brM2 | 2 | 2 | 2 | 2 | 2 | 2 | 2 | 0 | 2 |
| | | | ▼ | ▼ | ▼ | ▼ | ▼ | | |
| brM3 | 2 | 2 | 0 | 0 | 0 | 0 | 0 | 0 | 2 |
| brM4 | 2 | 2 | 0 | 0 | 0 | 0 | 0 | 0 | 2 |
| brM5 | 2 | 2 | 0 | 0 | 0 | 0 | 0 | 0 | 2 |
| | ▲ | ▲ | | | | | | | |
| brM7 | 0 | 0 | 0 | 0 | 0 | 0 | 0 | 0 | 2 |
| brM8 | 0 | 0 | 0 | 0 | 0 | 0 | 0 | 0 | 2 |
| Recombination site | 4 | 4 | 5 | 5 | 5 | 5 | 5 | | |
| Phenotype[e] | B | B | N | N | N | N | N | N | B |
| Number of tested plants[f] | 6 | 6 | 6 | 6 | 6 | 6 | 6 | | |

[a]The corresponding chromosome positions for molecular markers on the SL3.0 assembly are from https://solgenomics.net
[b]Recombinant inbred lines. The population was developed from a cross between Fla. 8624 and Fla. 8834
[c]Based on the genotyping results, 0 designates that the selected line was homozygous for the marker allele originating from the normal (without br) parent, 2 designates the line was homozygous for the allele from the homozygous br parent
[d]Arrows pointed in the direction that the br is located
[e]B, br phenotype; N, normal phenotype
[f]Number of selected plants phenotyped in each line

TABLE 6

Fine mapping the br in the population Fla. 8044 × Fla. 8916

| Marker[a] | Selected lines | | | | | | | | | | |
|---|---|---|---|---|---|---|---|---|---|---|---|
| | RIL2-1[b] | RIL2-2 | RIL2-3 | RIL2-4 | RIL2-5 | RIL2-6 | RIL2-7 | RIL2-8 | RIL2-9 | Fla. 8044 | Fla. 8916 |
| brM2 | 0[c] | 0 | 0 | 0 | 2 | 2 | 2 | 2 | 2 | 0 | 2 |
| brM3 | 0 | 0 | 0 | 0 | 2 | 2 | 2 | 2 | 2 | 0 | 2 |
| brM4 | 0 | 0 | 0 | 0 | 2 | 2 | 2 | 2 | 2 | 0 | 2 |
| | | | | ▼[d] | ▼ | | | | | | |
| brM5 | 0 | 0 | 2 | 2 | 2 | 2 | 2 | 2 | 2 | 0 | 2 |
| | ▲ | ▲ | | | ▲ | ▲ | ▲ | ▲ | ▲ | | |
| brM7 | 2 | 2 | 2 | 2 | 0 | 0 | 0 | 0 | 0 | 0 | 2 |
| brM8 | 2 | 2 | 2 | 2 | 0 | 0 | 0 | 0 | 0 | 0 | 2 |
| Recombination site | 1 | 1 | 2 | 2 | 3 | 3 | 3 | 3 | 3 | | |
| Phenotype[e] | N | N | B | B | B | B | B | B | B | N | B |
| Number of tested plants[f] | 6 | 6 | 6 | 6 | 6 | 6 | 6 | 6 | 6 | | |

[a]Each marker corresponds to the same position as Table 5
[b]Recombinant inbred lines. The population was developed from a cross between Fla. 8044 and Fla. 8916
[c]Based on the genotyping results, 0 designates that the selected line was homozygous for the marker allele originating from the normal (without br) parent, 2 designates the plant was homozygous for the allele from the br parent
[d]The arrows pointed in the direction that the br is located
[e]B, br phenotype; N, normal phenotype
[f]Number of selected plants phenotyped in each line

Example 7. Br Locus Sequence

Figure 2:
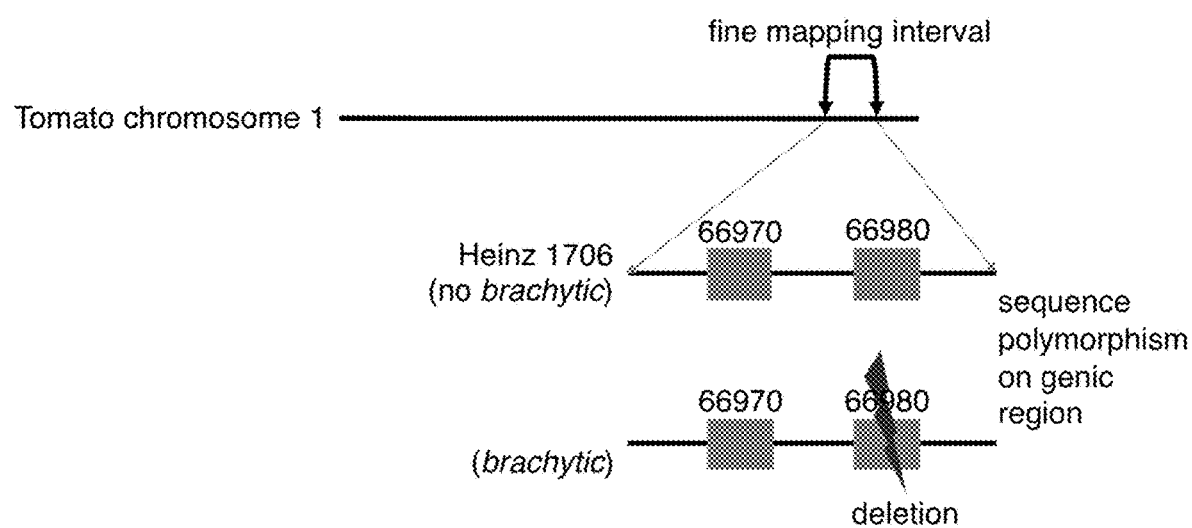

According to the current genome annotation ITAG3.2 (Sol Genomics Network), there are 55 predicted genes (Solyc01g066890 to Solyc01g067390) within the interval to which we have mapped the br locus. Using an Illumina HiSeq 4000 system and 10× Genomics' Chromium library, we analyzed the genome sequence of a selected single plant homozygous for the brachytic genotype. The accepted name for tomato genes follows the format Solyc01g066980. Gene names were reduced to 66980 for instance in this application. Two genes, 66970 and 66980, were selectively displayed in this diagram (FIG. 2).

The assembly (FIG. 2) and alignment (FIG. 3.) data showed no sequence polymorphisms in the fine mapping interval to the normal genotype except for Solyc01g066980. Therefore, the allelic differences between the brachytic phenotype and normal phenotype are attributed to a single gene variation within the fine mapped interval. This finding was confirmed using sequence alignment method (FIG. 3).

Figure 4:
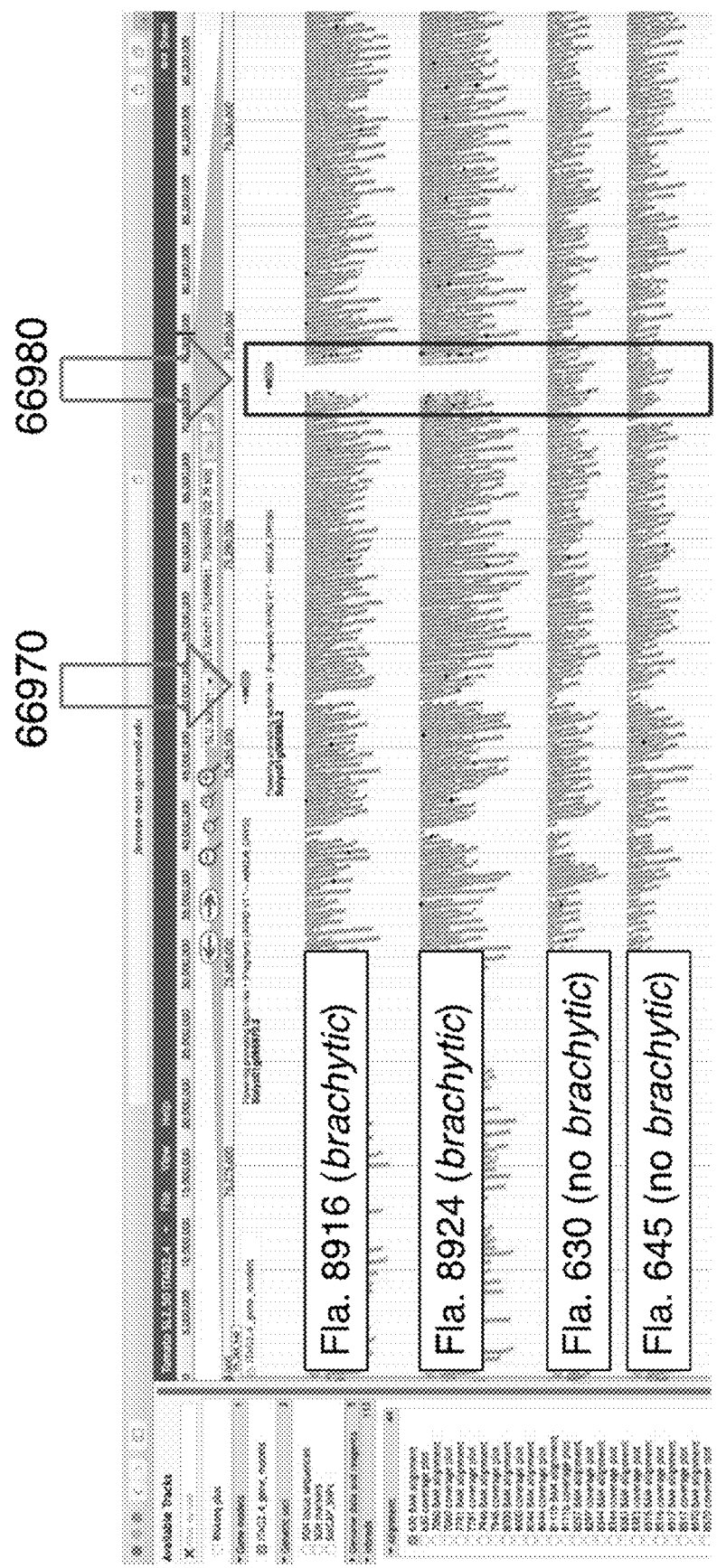
FIG. 4. Tomato brachytic mapping interval, showing the deletion for 66980 in brachytic tomatoes FIG. 5. Gel image of a molecular marker tagging the deletion in a gene Solyc01g066980.

Two different inbred lines (Fla. 8916 & Fla. 8924) homozygous for the brachytic genotype and 17 inbred lines (Fla. 7781, Fla. 8000, Fla. 8111B, Fla. 8297, Fla. 8344, Fla. 8383, Fla. 8516, Fla. 8517, Fla. 8570, Fla. 8624, Fla. 8638, Fla. 8820, Fla. 8872B, Fla. 8925, Fla. 8932, Fla. 630, & Fla. 645) with normal genotype (no brachytic) were sequenced using Illumina HiSeq system to achieve dense single nucleotide polymorphism (SNP) coverage. For each line, the approach described by Lee et al. (2018) was used to identify sequence polymorphisms compared with the Heinz 1706 reference genome assembly. The browser displays the alignment read of Fla. 8916, Fla. 8924, Fla. 630 and Fla. 645. Gene annotations based on SL2.50 have been activated. Results were confirm using SL3.0 version of Heinz 1706 reference. The deletion of 66980 in two lines that does have brachytic is highlighted in the red box (FIG. 4).

Example 8. PCR-Based Brachytic Marker. PCR Primers

Figure 5:
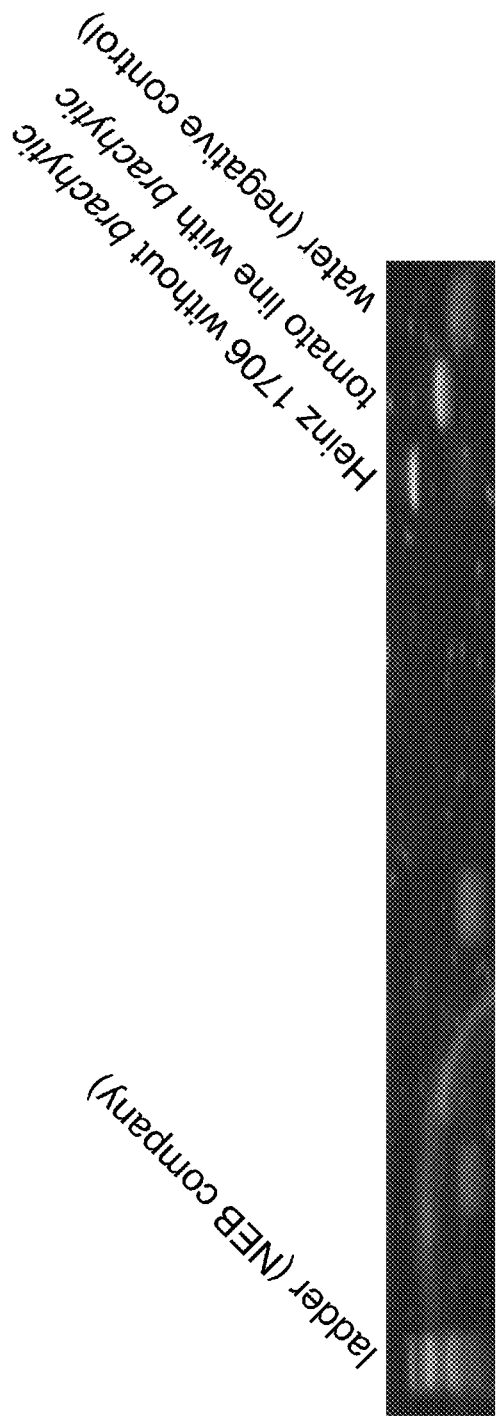

66980F3 (5'-AAAGGATGAGCCTTCTTGGG-3' SEQ ID NO: 9) and 66980R3 (5'-CCACTATCCACTTTAAGACCTCTATC-3' SEQ ID NO: 10) were used to amplify genomic DNA from brachytic and normal plants. PCR amplifications were visualized using gel electrophoresis system (Bio-Rad) as describe below: 1% agarose gel was made with 0.5% TBE buffer. The electrophoresis was run for 30 min. under 100 V. SYBR Gold (INVITROGEN™) was added to samples. 2 µl of samples loaded. Picture was obtained under blue light. In any tomato breeding population that contains this brachytic locus, this genetic marker can be used to select for plants carrying brachytic (FIG. 5).

Other primer pairs that can be used to amplify sequences for detection of brachytic markers include, but are not limited to:

```
RS041917m:  SL2.50ch01:75268297 . . . 75268341 bp
                                          SEQ ID NO: 11
Forward:    5'-AAACACTTCCAGTCAGTA-3'
                                          SEQ ID NO: 12
Reverse:    5'-TTGTTGACAATCTAAGGAAG-3'

CGH-75.29:  SL3.0ch01:75,102,363-75,110,048 bp
                                          SEQ ID NO: 13
Forward:    5'-CTTGGGATGCGTGCACTTTC-3'
                                          SEQ ID NO: 14
Forward-1:  5'-GAACTTTTCGGAGTCCGTTCG-3'
                                          SEQ ID NO: 15
Reverse:    5'-ACCCCTCACACCCTCTTACA-3'

RS041917t:  SL2.50ch01:75314323 . . . 75314373 bp
                                          SEQ ID NO: 16
Forward:    5'-TCAAAACTCAAATAACAAGAATG-3'
                                          SEQ ID NO: 17
Reverse:    5'-TCATGAATAGGCACCAATAA-3'

RS041917u:  SL2.50ch01:75360405 . . . 75360472 bp
                                          SEQ ID NO: 18
Forward:    5'-GGATTTCAAAGTCATGACAA-3'
                                          SEQ ID NO: 19
Reverse:    5'-TACGTACATGTGGCATTT-3'

RS041917h:  SL3.00ch01:74990561 . . .
74990619, 74990589
                                          SEQ ID NO: 20
Forward:    5'-TCAAATTTTAGACCTCTAAGTAAAA-3'
                                          SEQ ID NO: 21
Reverse:    5'-GTCGTGGCTAAACTTAATTC-3'

RS041917k:  SL3.00ch01:75067607 . . .
75067663, 75067637
                                          SEQ ID NO: 22
Forward:    5'-AAGAAGCTCGAGAACTAATTT-3'
                                          SEQ ID NO: 23
Reverse:    5'-CCATTGTGGACACTCAATTT-3'

RS041917w:  SL3.00ch01:75306037 . . .
75306088, 75306058
                                          SEQ ID NO: 24
Forward:    5'-TGTCACAGTGAACATGTATT-3'
                                          SEQ ID NO: 25
Reverse:    5'-CTTGATGAATTGACTTTCAAATG-3'

RS041917x:  SL3.00ch01:75351329 . . .
75351395, 75351358
                                          SEQ ID NO: 26
Forward:    5'-CCCTTGTTATTTAACATTGATTT-3'
                                          SEQ ID NO: 27
Reverse:    5'-GCAGTAATAAAGATCTGAACAA-3'

RS041917y:  SL3.00ch01:75516627 . . .
75516727, 75516692
                                          SEQ ID NO: 28
Forward:    5'-GTGTTTCTAACATTCAAGCA-3'
                                          SEQ ID NO: 29
Reverse:    5'-TCAAATTGTCCTGTGCAA-3'

RS041917z:  SL3.00ch01:75531402 . . .
75531471, 75531427
                                          SEQ ID NO: 30
Forward:    5'-GGATAAAGATTCTCCAGGTT-3'
                                          SEQ ID NO: 31
Reverse:    5'-TTGAGCTCATCATGCTA-3'
```

Example 9. Identification of Brachytic Gene in Related Plants

Figure 6:
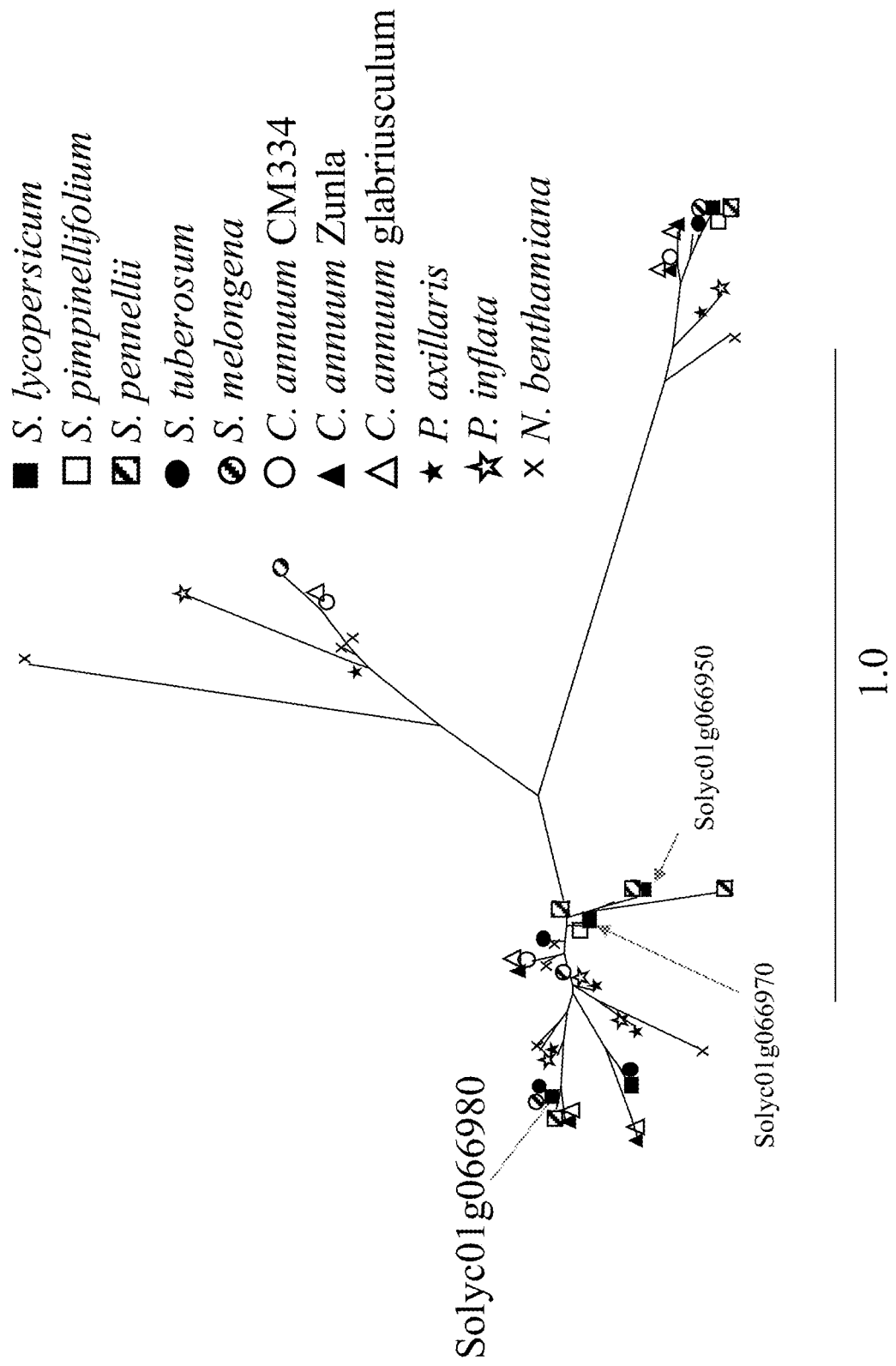
FIG. 6. Orthologs of flowering-promoting factor 1 gene were identified in diverse Solanaceae species by using a hidden Markov model search (HMMER 3.1b2; biosequence analysis using profile hidden Markov models).

Maximum likelihood phylogenetic analysis of the Flowering Promoting Factor 1 protein sequence alignment (Solyc01g066950, Solyc01g066970 and Solyc01g066980) was performed using RAxMLHPC-PTHREADS-SSE3 (version 8.2.3; Stamatakis A "AxML version 8: a tool for phylogenetic analysis and post-analysis of large phylogenies" Bioinformatics. 2014 May 1; 30(9):1312-3) for the Linux platform using the VT model of amino acid substitutions and gamma distribution parameters estimated by the software. 1000 bootstraps were performed. Phylogenetic trees were visualized and edited in Geneious 10.2.2 (BIOMATTERS). The search revealed a pepper gene (Sequence ID: XP_016557588.1) closely related to Solyc01g066980, indicating the potential of the brachytic locus creating smaller plant architecture without yield reductions in horticultural fruits in the Solanaceae family (FIG. 6).

Example 9. Identification of Brachytic Gene in Related Plants

The Solanaceae annotated protein datasets were obtained from National Center for Biotechnology Information (NCBI) and Sol Genomics Network. Putative orthologs of brachytic genes were identified by using a hidden Markov model search (HMMER 3.1b2). The seed alignment model (PTHR33433) from Pfam (EMBLI-EBI Pfam 32.0, El-Gebali et al. "The Pfam protein families database in 2019" Nucleic Acids Research 2019 47(D1):D427-D432) was used to identify canonical proteins of Solanaceae species. 10-1 e-value cutoff was applied. Solanaceae sequence alignments were performed using the MUSCLE tool (muscle 3.8.31; Edgar R C. 2004. MUSCLE: multiple sequence alignment with high accuracy and high throughput. Nucleic Acids Res. 32:1792-1797) for the Linux platform. Maximum likelihood (ML) phylogenetic analysis of the protein sequence alignment was performed using RAxMLHPC-PTHREADS-SSE3 (version 8.2.3; Stamatakis A. 2014. RAxML version 8: a tool for phylogenetic analysis and post-analysis of large phylogenies. Bioinformatics. 30:1312-1313) for the Linux platform using the VT model of amino acid substitutions and gamma distribution parameters estimated by the software. 1000 bootstraps were performed. Phylogenetic trees were visualized and edited in Geneious R10.2.2 (BIOMATTERS). The search revealed pepper genes (*C. annuum Zunla*, Capana01g003223; *C. annuum glabriusculum*, Capang08g000164), potato gene (*S. tuberosum*, XP_006342791), wild tomato gene (*S. pennellii*, XP_015086900), eggplant gene (*S. melongena*, Sme2.5_02338.1_g00005), petunia genes (*P. axillaris*, Peaxi162Scf00534g00005; *P. inflata*, Peinf101Scf01113g00005) and tobacco gene (*N. benthamiana*, Niben101Scf10524g05008) closely related to Solyc01g066980, indicating the potential of the brachytic locus creating smaller plant architecture without yield reductions in horticultural fruits in the Solanaceae family (FIG. 6).

Example 10. Brachytic Tomato Plants Produced Marketable Fruit

Fruits were harvested on Dec. 31, 2017 when approximately 70% of fruits had attained a mature color (hereafter, once-over harvest data). Statistical significance is indicated by $P<0.05$ using a one-way ANOVA followed by a Duncan's test. Genotypes (from left to right) on the x-axis are 1; Fla. 8653 without brachytic, 2; Fla. 8916 with brachytic, 4; Sanibel, 5; F1 from a cross from genotypes 1 and 2, 6; F6 of Fla. 8653×Fla. 8916 (homozygous brachytic), and 7; F6 of Fla. 8653×Fla. 8916 (without brachytic). Genotypes 6 and 7 are sister lines that are from the same cross, but were split into two different selection, one with the brachytic and the other without the brachytic. Three plot replications were performed for each genotype. Each plot contained ten plants.

TABLE 7

Brachytic-associated effects on tomato fruit yield under once-over harvest conditions.
Tomato fruit weight (gram) vs genotype

| Sample | Result |
| --- | --- |
| a combined total of S-MF, M-MF, L-MF, X-MF, S-UF, M-UF, L-UF, and X-UF | Genotype effect was not significant in multiple comparison |
| a combined total of M-MF, L-MF, X-MF, M-UF, L-UF, and X-UF | Genotype effect was not significant in multiple comparison |
| a combined total of S-MF, and S-UF | Genotype effect was not significant in multiple comparison |
| a combined total of M-MF and M-UF | Genotype effect was not significant in multiple comparison |
| a combined total of L-MF and L-UF | Genotype effect was not significant in multiple comparison |
| a combined total of X-MF and X-UF | Genotype effect was not significant in multiple comparison |
| a combined total of S-MF, M-MF, L-MF, and X-MF | Genotype effect was not significant in multiple comparison |
| a combined total of M-MF, L-MF, and X-MF | Genotype effect was not significant in multiple comparison |
| S-MF | Genotype effect was not significant in multiple comparison |
| M-MF | Genotype effect was not significant in multiple comparison |
| L-MF | Genotype effect was not significant in multiple comparison |
| X-MF | Genotype effect was not significant in multiple comparison |
| a combined total of S-UF, M-UF, L-UF, and X-UF | No statistical significance between genotypes 6 and 7 |
| a combined total of M-UF, L-UF, and X-UF | No statistical significance between genotypes 6 and 7 |
| S-UF | Genotype effect was not significant in multiple comparison |
| M-UF | No statistical significance between genotypes 6 and 7 |
| L-UF | Genotype effect was not significant in multiple comparison |

TABLE 7-continued

Brachytic-associated effects on tomato fruit yield under once-over harvest conditions.
Tomato fruit weight (gram) vs genotype

| Sample | Result |
| --- | --- |
| X-UF | No statistical significance between genotypes 6 and 7 |
| a combined total of S-MRF, M-MRF, L-MRF, X-MRF, S-URF, M-URF, L-URF, and X-URF | Statistical significance between genotypes 6 and 7 was observed |
| a combined total of M-MRF, L-MRF, X-MRF, M-URF, L-URF, and X-URF | Statistical significance between genotypes 6 and 7 was observed |
| a combined total of S-MRF and S-URF | No statistical significance between genotypes 6 and 7 |
| a combined total of M-MRF and M-MRF | Statistical significance between genotypes 6 and 7 was observed |
| a combined total of L-MRF and L-URFL | Statistical significance between genotypes 6 and 7 was observed |
| a combined total of X-MRF and X-URF | Statistical significance between genotypes 6 and 7 was observed |
| a combined total of S-MRF, M-MRF, L-MRF, and X-MRF | No statistical significance between genotypes 6 and 7 |
| a combined total of M-MRF, L-MRF, and X-MRF | Statistical significance between genotypes 6 and 7 was observed |
| S-MRF | No statistical significance between genotypes 6 and 7 |
| M-MRF | Statistical significance between genotypes 6 and 7 was observed |
| L-MRF | Statistical significance between genotypes 6 and 7 was observed |
| X-MRF | No statistical significance between genotypes 6 and 7 |
| a combined total of S-URF, M-URF, L-URF, and X-URF | Statistical significance between genotypes 6 and 7 was observed |
| a combined total of M-URF, L-URF, and X-URF | No statistical significance between genotypes 6 and 7 |
| S-URF | Genotype effect was not significant in multiple comparison |
| M-URF | No statistical significance between genotypes 6 and 7 |
| L-URF | No statistical significance between genotypes 6 and 7 |
| X-URF | No statistical significance between genotypes 6 and 7 |
| a combined total of S-MGF, M-MGF, L-MGF, X-MGF, S-UGF, M-UGF, L-UGF, and X-UGF | No statistical significance between genotypes 6 and 7 |
| a combined total of M-MGF, L-MGF, X-MGF, M-UGF, L-UGF, and X-UGF | No statistical significance between genotypes 6 and 7 |
| a combined total of S-MGF and S-UGF | Genotype effect was not significant in multiple comparison |
| a combined total of M-MGF and M-UGF | Genotype effect was not significant in multiple comparison |
| a combined total of L-MGF and L-UGF | No statistical significance between genotypes 6 and 7 |
| a combined total of X-MGF and X-UGF | No statistical significance between genotypes 6 and 7 |
| a combined total of S-MGF, M-MGF, L-MGF, and X-MGF | No statistical significance between genotypes 6 and 7 |
| a combined total of M-MGF, L-MGF, and X-MGF | No statistical significance between genotypes 6 and 7 |
| S-MGF | Genotype effect was not significant in multiple comparison |
| M-MGF | Genotype effect was not significant in multiple comparison |
| L-MGF | No statistical significance between genotypes 6 and 7 |
| X-MGF | No statistical significance between genotypes 6 and 7 |
| a combined total of S-UGF, M-UGF, L-UGF, and X-UGF | Genotype effect was not significant in multiple comparison |
| a combined total of M-UGF, L-UGF, and X-UGF | Genotype effect was not significant in multiple comparison |
| S-UGF | Genotype effect was not significant in multiple comparison |
| M-UGF | Genotype effect was not significant in multiple comparison |
| L-UGF | Genotype effect was not significant in multiple comparison |
| X-UGF | No statistical significance between genotypes 6 and 7 |

Fruits were harvested on Dec. 18 (1st), 22 (2nd), 26 (3rd), and 30th (4th) in 2017 (hereafter, multiple harvest data). Fruits that attained a mature color were harvested. Statistical significance is indicated by P<0.05 using a one-way ANOVA followed by a Duncan's test. Genotypes (from left to right) on the x-axis are 1; Fla. 8653 without brachytic, 2; Fla. 8916 with brachytic, 4; Sanibel, 5; F1 from a cross from genotypes 1 and 2, 6; F6 of Fla. 8653×Fla. 8916 (homozygous brachytic), and 7; F6 of Fla. 8653×Fla. 8916 (without brachytic). Genotypes 6 and 7 are sister lines that are from the same cross, but were split into two different selection, one with the brachytic and the other without the brachytic. Three plot replications were performed for each genotype. Each plot contained ten plants.

TABLE 8

Brachytic-associated effects on tomato fruit yield (fruit weight) under multiple harvest condition
Tomato fruit weight (gram) vs genotype

| Sample | Harvest | Result |
|---|---|---|
| a combined total of S-MRF, M-MRF, L-MRF, X-MRF, S-URF, M-URF, L-URF, and X-URF | $1^{st}$ $2^{nd}$ $3^{rd}$ $4^{th}$ | Statistical significance between genotypes 6 and 7 was observed [a] |
| a combined total of M-MRF, L-MRF, X-MRF, M-URF, L-URF, and X-URF | $1^{st}$ $2^{nd}$ $3^{rd}$ $4^{th}$ | Statistical significance between genotypes 6 and 7 was observed |
| a combined total of S-MRF and S-URF | $1^{st}$ $2^{nd}$ $3^{rd}$ $4^{th}$ | No statistical significance between genotypes 6 and 7 Genotype effect was not significant in multiple comparison Statistical significance between genotypes 6 and 7 was observed |
| a combined total of M-MRF and M-URF | $1^{st}$ $2^{nd}$ $3^{rd}$ $4^{th}$ | Genotype effect was not significant in multiple comparison |
| a combined total of L-MRF and L-URF | $1^{st}$ $2^{nd}$ $3^{rd}$ $4^{th}$ | No statistical significance between genotypes 6 and 7 Statistical significance between genotypes 6 and 7 was observed |
| a combined total of X-MRF and X-URF | $1^{st}$ $2^{nd}$ $3^{rd}$ $4^{th}$ | Statistical significance between genotypes 6 and 7 was observed |
| a combined total of S-MRF, M-MRF, L-MRF and X-MRF | $1^{st}$ $2^{nd}$ $3^{rd}$ $4^{th}$ | No statistical significance between genotypes 6 and 7 Statistical significance between genotypes 6 and 7 was observed |
| a combined total of M-MRF, L-MRF and X-MRF | $1^{st}$ $2^{nd}$ $3^{rd}$ $4^{th}$ | No statistical significance between genotypes 6 and 7 Statistical significance between genotypes 6 and 7 was observed |
| S-MRF | $1^{st}$ $2^{nd}$ $3^{rd}$ $4^{th}$ | Genotype effect was not significant in multiple comparison Statistical significance between genotypes 6 and 7 was observed |
| M-MRF | $1^{st}$ $2^{nd}$ $3^{rd}$ $4^{th}$ | Genotype effect was not significant in multiple comparison |
| L-MRF | $1^{st}$ $2^{nd}$ $3^{rd}$ $4^{th}$ | No statistical significance between genotypes 6 and 7 Statistical significance between genotypes 6 and 7 was observed |
| X-MRF | $1^{st}$ $2^{nd}$ $3^{rd}$ $4^{th}$ | No statistical significance between genotypes 6 and 7 Statistical significance between genotypes 6 and 7 was observed No statistical significance between genotypes 6 and 7 |
| a combined total of S-URF, M-URF, L-URF, and X-URF | $1^{st}$ $2^{nd}$ $3^{rd}$ $4^{th}$ | Statistical significance between genotypes 6 and 7 was observed |
| a combined total of M-URF, L-URF, and X-URF | $1^{st}$ $2^{nd}$ $3^{rd}$ $4^{th}$ | Statistical significance between genotypes 6 and 7 was observed No statistical significance between genotypes 6 and 7 |
| S-URF | $1^{st}$ $2^{nd}$ $3^{rd}$ $4^{th}$ | No statistical significance between genotypes 6 and 7 Statistical significance between genotypes 6 and 7 was observed No statistical significance between genotypes 6 and 7 |

TABLE 8-continued

Brachytic-associated effects on tomato fruit yield (fruit weight) under multiple harvest condition
Tomato fruit weight (gram) vs genotype

| Sample | Harvest | Result |
|---|---|---|
| M-URF | $1^{st}$ | Genotype effect was not significant in multiple comparison |
|  | $2^{nd}$ |  |
|  | $3^{rd}$ |  |
|  | $4^{th}$ |  |
| L-URF | $1^{st}$ | Statistical significance between genotypes 6 and 7 was observed |
|  | $2^{nd}$ | No statistical significance between genotypes 6 and 7 |
|  | $3^{rd}$ |  |
|  | $4^{th}$ | Genotype effect was not significant in multiple comparison |
| X-URF | $1^{st}$ | Statistical significance between genotypes 6 and 7 was observed |
|  | $2^{nd}$ |  |
|  | $3^{rd}$ |  |
|  | $4^{th}$ | Genotype effect was not significant in multiple comparison |

Fruits were harvested on Dec. 18 (1st), 22 (2nd), 26 (3rd), and 30th (4th) in 2017 (hereafter, multiple harvest data). Fruits that attained a mature color were harvested. Statistical significance is indicated by P<0.05 using a one-way ANOVA followed by a Duncan's test. Genotypes (from left to right) on the x-axis are 1; Fla. 8653 without brachytic, 2; Fla. 8916 with brachytic, 4; Sanibel, 5; F1 from a cross from genotypes 1 and 2, 6; F6 of Fla. 8653×Fla. 8916 (homozygous brachytic), and 7; F6 of Fla. 8653×Fla. 8916 (without brachytic). Genotypes 6 and 7 are sister lines that are from the same cross, but were split into two different selection, one with the brachytic and the other without the brachytic. Three plot replications were performed for each genotype. Each plot contained ten plants.

TABLE 9

Brachytic-associated effects on tomato fruit yield (fruit number) under multiple harvest condition.
tomato fruit number vs. genotype

| Sample | Harvest | Result |
|---|---|---|
| a combined total of S-MRF, M-MRF, L-MRF, X-MRF, S-URF, M-URF, L-URF, and X-URF | $1^{st}$ | Statistical significance between genotypes 6 and 7 was observed |
|  | $2^{nd}$ |  |
|  | $3^{rd}$ |  |
|  | $4^{th}$ |  |
| a combined total of M-MRF, L-MRF, X-MRF, M-URF, L-URF, and X-URF | $1^{st}$ | No statistical significance between genotypes 6 and 7 |
|  | $2^{nd}$ | Statistical significance between genotypes 6 and 7 was observed |
|  | $3^{rd}$ |  |
|  | $4^{th}$ |  |
| a combined total of S-MRF and S-URF | $1^{st}$ | No statistical significance between genotypes 6 and 7 |
|  | $2^{nd}$ |  |
|  | $3^{rd}$ | Statistical significance between genotypes 6 and 7 was observed |
|  | $4^{th}$ |  |
| a combined total of M-MRF and M-URF | $1^{st}$ | Genotype effect was not significant in multiple comparison |
|  | $2^{nd}$ |  |
|  | $3^{rd}$ |  |
|  | $4^{th}$ |  |
| a combined total of L-MRF and L-URF | $1^{st}$ | No statistical significance between genotypes 6 and 7 |
|  | $2^{nd}$ | Statistical significance between genotypes 6 and 7 was observed |
|  | $3^{rd}$ |  |
|  | $4^{th}$ |  |
| a combined total of X-MRF and X-URF | $1^{st}$ | No statistical significance between genotypes 6 and 7 |
|  | $2^{nd}$ | Statistical significance between genotypes 6 and 7 was observed |
|  | $3^{rd}$ |  |
|  | $4^{th}$ |  |
| a combined total of S-MRF, M-MRF, L-MRF and X-MRF | $1^{st}$ | No statistical significance between genotypes 6 and 7 |
|  | $2^{nd}$ | Statistical significance between genotypes 6 and 7 was observed |
|  | $3^{rd}$ |  |
|  | $4^{th}$ |  |
| a combined total of M-MRF, L-MRF and X-MRF | $1^{st}$ | No statistical significance between genotypes 6 and 7 |
|  | $2^{nd}$ | Statistical significance between genotypes 6 and 7 was observed |
|  | $3^{rd}$ |  |
|  | $4^{th}$ |  |
| S-MRF | $1^{st}$ | Genotype effect was not significant in multiple comparison |
|  | $2^{nd}$ | No statistical significance between genotypes 6 and 7 |
|  | $3^{rd}$ |  |
|  | $4^{th}$ |  |
| M-MRF | $1^{st}$ | Genotype effect was not significant in multiple comparison |
|  | $2^{nd}$ |  |
|  | $3^{rd}$ |  |
|  | $4^{th}$ |  |

TABLE 9-continued

Brachytic-associated effects on tomato fruit yield (fruit number) under multiple harvest condition.
tomato fruit number vs. genotype

| Sample | Harvest | Result |
|---|---|---|
| L-MRF | $1^{st}$ | No statistical significance between genotypes 6 and 7 |
| | $2^{nd}$ | |
| | $3^{rd}$ | Statistical significance between genotypes 6 and 7 was |
| | $4^{th}$ | observed |
| X-MRF | $1^{st}$ | No statistical significance between genotypes 6 and 7 |
| | $2^{nd}$ | |
| | $3^{rd}$ | Statistical significance between genotypes 6 and 7 was |
| | $4^{th}$ | observed |
| a combined total of S-URF, M-URF, L-URF, and X-URF | $1^{st}$ | No statistical significance between genotypes 6 and 7 |
| | $2^{nd}$ | |
| | $3^{rd}$ | Statistical significance between genotypes 6 and 7 was observed |
| | $4^{th}$ | No statistical significance between genotypes 6 and 7 |
| a combined total of M-URF, L-URF, and X-URF | $1^{st}$ | Statistical significance between genotypes 6 and 7 was observed |
| | $2^{nd}$ | |
| | $3^{rd}$ | |
| | $4^{th}$ | Genotype effect was not significant in multiple comparison |
| S-URF | $1^{st}$ | Genotype effect was not significant in multiple comparison |
| | $2^{nd}$ | |
| | $3^{rd}$ | |
| | $4^{th}$ | |
| M-URF | $1^{st}$ | Genotype effect was not significant in multiple comparison |
| | $2^{nd}$ | |
| | $3^{rd}$ | |
| | $4^{th}$ | |
| L-URF | $1^{st}$ | Statistical significance between genotypes 6 and 7 was observed |
| | $2^{nd}$ | |
| | $3^{rd}$ | |
| | $4^{th}$ | Genotype effect was not significant in multiple comparison |
| X-URF | $1^{st}$ | Statistical significance between genotypes 6 and 7 was observed |
| | $2^{nd}$ | |
| | $3^{rd}$ | |
| | $4^{th}$ | Genotype effect was not significant in multiple comparison |

Acronyms in Fruit Data in Tables

MF: marketable fruits. Fruits include both red and green ones in this criteria.
UF: unmarketable fruits. Fruits include both red and green ones in this criteria.
MRF: marketable red fruits
URF: unmarketable red fruits
MGF: marketable green fruits
UGF: unmarketable green fruits
Red and green fruits represent fruits with a mature color [pink color on tip (blossom end)] and fruits without that color, respectively. Unmarketable fruits mean defected fruits such as fruits with scars, crack, or zipperling.

Prefixes in Fruit Data in Tables

S-: small size fruits. Less than 2.25" in diameter.
M-: medium size fruits. Greater than or equal to 2.25" or less than 2.5" in diameter.
L-: large size fruits. Greater than or equal to 2.5" or less than 2.75" in diameter.
X-: extra large size fruits. Greater than 2.75" in diameter.
For example, S-MF means small sized marketable fruits.

Figure 7:
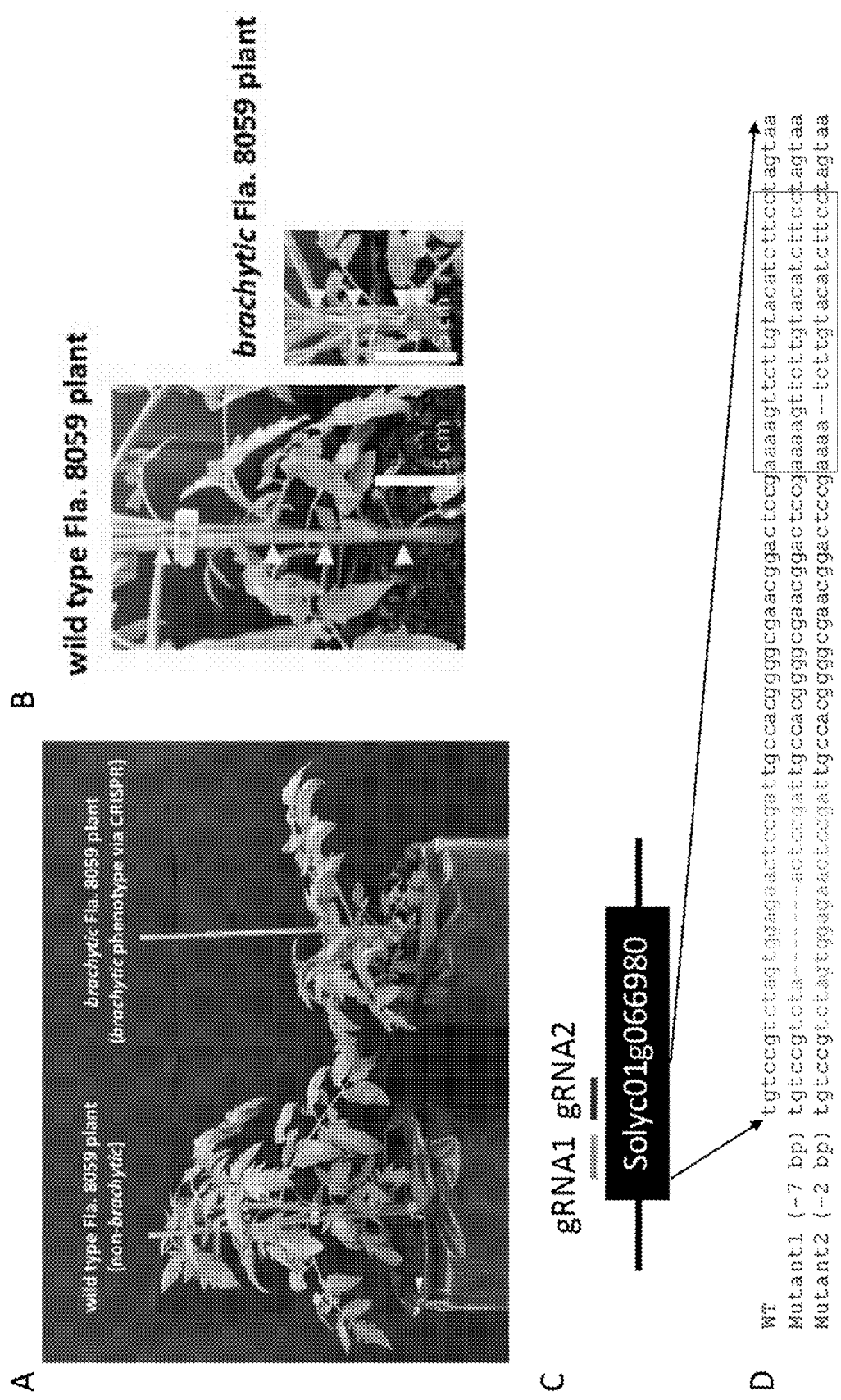
FIG. 7. Creation of brachytic plants via CRISPR-Cas9 technique; (A) normal plant (left) and CRISPR-Cas9 induced brachytic plant (right); (B) Reduced internode length on brachytic plant (right) compared with the internode on normal plant (left); (C) Targeted guide RNA sites 1 (gray text) and 2 (boxed text) in normal phenotype reference annotation of the Solyc01g066980 gene; and (D) Screening CRISPR-Cas9 induced sequence polymorphisms from representative plants. Mutant1 and Mutant2 plants show deletions (−) WT=tgtccgtct-agtggagaactccgattgccacggggcgaacggactccgaaaagttcttgta-catcttcctagtaa (SEQ ID NO: 65); Mutant1= tgtccgtctaactccgattgccacggggcgaacggactccgaaaagttcttgta-catcttcctagtaa (SEQ ID NO: 66), and Mutant2=tgtccgtctagtggagaactccgattgccacggggcgaacgg-actccgaaaatcttgtacatcttcctagtaa (SEQ ID NO: 67).
Figure 7E:
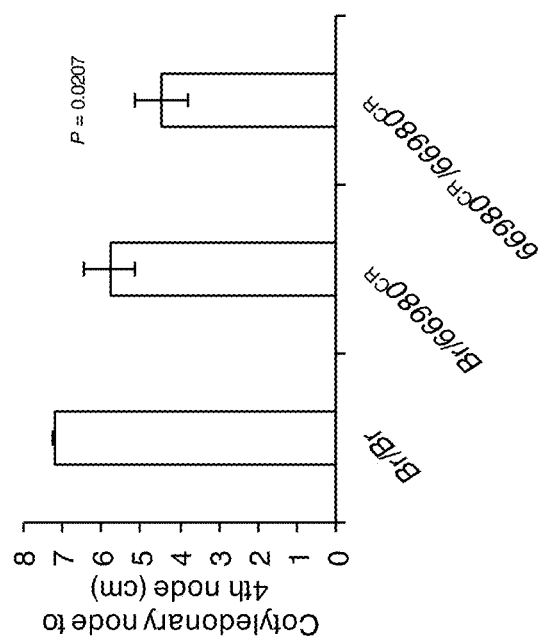
FIG. 7E. Graph illustrating reduced stem length of tomato mediated by CRISPR/Cas9-induced homozygous brachytic allele. After CRISPR/Cas9 events, selfed heterozygous lines (T0) were harvested to generate T1 seeds. Transgene-free T1 plants were used for analysis. Statistical significance was calculated using a one-way analysis of variance followed by a two-tailed Tukey's multiple comparison test. Br, wild type normal allele; 66980CR, CRISPR/Cas9-induced brachytic allele. Numbers of individual plants were >10.

Example 11. Materials and Methods for Gene Editing in Tomato Plants Using CRISPR-Cas9 Technique CRISPR constructs were designed to create deletions within a target gene (SEQ ID NO: 49) using a single guide RNA (gRNA) alongside the zCas9 endonuclease gene. zCas9 is a Cas9 gene that has been codon optimized for maize. Two different gRNA sequences containing SEQ ID NO: 50 and 51 guide sequences were used to form CRISPR/zCas9 constructs to genetically modify the brachytic locus in tomato plants to produce brachytic plants. The locations of the guide sequences relative to the Solyc01g06680 region are illustrated in FIG. 7 panels C and D. All constructs were assembled as described by Xie et al. 2014 with minor modifications. pHSN401 vector (Addgene) was used to make the CRISPR/zCas9 constructs. *Agrobacterium tumefaciens*-mediated transformations of the standard fresh-market tomato (*Solanum lycopersicum*) variety Fla. 8059 were performed according to Van Eck et al. 2006 with minor modifications. Two different *A. tumefaciens* strains AGL1 (ATCC) and LBA4404 (Takara Bio USA), containing the indicted CRISPR/zCas9 constructs were used for transformations. After selecting regenerants on selecting media with hygromycin, regenerants were move to the greenhouse. Young leaf tissues were collected from each T0 plant, and genomic DNA was extracted using Qiagen DNeasy kit (Qiagen, USA). Each plant was genotyped for the presence of the CRISPR/zCas9 construct using Sanger method (PCR primers SEQ ID NO: 52-61) and T7 Endonuclease I assay (SEQ ID NO: 62 and 63). Plants positive for Cas9 T-DNA were further genotyped for brachytic genome modification using Sanger (SEQ ID NO: 62 and 63).

As shown in FIG. 7, tomato plants having CRISPR/zCas9-induced deletions in the brachytic genomic locus exhibited the brachytic phenotype, shortened height and decreased internode length (compare left (normal) and right (genetically modified) plants in FIG. 7 panels A, B, and E). The genetically modified plants contained with a 7 base pair or 2 base pair deletion in the Soly01g066980 (brachytic) region (see FIG. 7 panels C and D).

Example 12. Identification of Protospacer-Adjacent Motif (PAM) Sites on the Solyc01g066980 Gene for CRISPR/zCas9 Generation of Brachytic Plants In addition to the guide sequences described above (SEQ ID NO: 50 and 51), additional guide sequences are suitable for forming gRNAs (as used herein gRNA can include crRNA, gRNA, and sgRNA) for CRISPR/zCas9 mediated genetic modification of the br locus. Suitable guide sequences include 17-20 nucleotide sequences in SEQ ID NO: 49 (nucleotides 21742-22373 of SEQ ID NO: 64) or a complement thereof, SEQ ID NO: 64 or a complement thereof, nucleotides 19742-22373 of SEQ ID NO: 64 or a complement thereof, nucleotides 16742-22373 of SEQ ID NO: 64 or a complement thereof, nucleotides 11742-22373 of SEQ ID NO: 64 or a complement thereof, nucleotides 1-22373 of SEQ ID NO: 64 or a complement thereof, nucleotides 21742-24373 of SEQ ID NO: 64 or a complement thereof, nucleotides 21742-27373 of SEQ ID NO: 64 or a complement thereof, nucleotides 21742-29135 of SEQ ID NO: 64 or a complement thereof, nucleotides 19742-24373 of SEQ ID NO: 64 or a complement thereof, nucleotides 16742-27373 of SEQ ID NO: 64 or a complement thereof, or nucleotides 11742-27373 of SEQ ID NO: 64 or a complement thereof that are unique compared to the rest of the genome and immediately adjacent (5') to a protospacer-adjacent motif (PAM) site. For zCas9, a PAM site is NGG. Thus, any unique 17-20 nucleotide sequence immediately 5' of a 5'-NGG-3' in SEQ ID NO: 49 or a complement thereof, SEQ ID NO: 64 or a complement thereof nucleotides 19742-22373 of SEQ ID NO: 64 or a complement thereof, nucleotides 16742-22373 of SEQ ID NO: 64 or a complement thereof, nucleotides 11742-22373 of SEQ ID NO: 64 or a complement thereof, nucleotides 1-22373 of SEQ ID NO: 64 or a complement thereof, nucleotides 21742-24373 of SEQ ID NO: 64 or a complement thereof, nucleotides 21742-27373 of SEQ ID NO: 64 or a complement thereof, nucleotides 21742-29135 of SEQ ID NO: 64 or a complement thereof, nucleotides 19742-24373 of SEQ ID NO: 64 or a complement thereof, nucleotides 16742-27373 of SEQ ID NO: 64 or a complement thereof, or nucleotides 11742-27373 of SEQ ID NO: 64 or a complement thereof can be used in forming a gRNA. PAM sites in the brachytic gene and its 5' and 3' flanking regions are shown in (FIG. 10, SEQ ID NO: 64). GG and CC PAM sites are shown in capital letters (Table 10, SEQ ID NO. 49 and SEQ ID NO: 64). CC sequences in the listed strand correspond to GG sequences in the complement strand. SEQ ID NO: 64 contains the brachytic locus (underlined) and its 5' and 3' flanking regions. The 5' and 3' flanking regions are not predicted to encode any genes. Deletions or insertions in the flanking regions may alter expression of the brachytic gene leading to plants displaying a brachytic phenotype.

CRISPR modification of the brachytic locus is not limited to the CRISPR/zCas9 system. Other CRISPR systems using different nucleases and having different PAM sequence requirements are known in the art. PAM sequences vary by the species of RNA-guided DNA endonuclease. For example, Class 2 CRISPR-Cas type II endonuclease derived from *S. pyogenes* utilizes an NGG PAM sequence located on the immediate 3' end of the guide sequence. Other PAM sequences include, but are not limited to, NNNNGATT (*Neisseria meningitidis*), NNAGAA (*Streptococcus thermophilus*), and NAAAAC (*Treponema denticola*). Guide sequences for CRISPR systems having nucleases with different PAM sequence requirements are identified as described above for zCas9, substituting the different PAM sequences.

In some embodiments, two or more gRNAs can be used. The two or more gRNAs can used with the same RNA-guided DNA endonuclease (Cas nuclease) or different RNA-guided DNA endonucleases.

CRISPR mediated modification of the brachytic locus in other Solanaceae plants is accomplished in a similar manner by selecting target sequences as described above for Solyc01g066980 and the corresponding ortholog sequences in the other Solanaceae plants.

TABLE 10

CRISPR modification of tomato plants-sequences

SEQ ID NO: 49 (Solyc01g066980 brachytic gene, guide sequences underlined)
catctcatcataaactacaaacacatacaaaaaacattctcattcaCCtttCCtctacaaaaaacataacaacatc
ttcaacaatcatgtctGGagtttGGgtattcaagaatGGtgttgtCCgtctagtGGagaactCCgattgCCacGGG
GcgaacGGactCCgaaaagttcttgtcatcttCCtagtaatgaagtcatcacatcatatgcagtacttgaaaGGa
aactgtactctcttGGatGGgagaGGtactatgatgaaCCtgaacttcttcaataCCacaaaagatcaaCCgttca
tcttatttctctaCCaaaGGatttcaacaGGttcaaatCCatgcatatgttcgatatcgtcgtcaagaatcgcaat
gaatttgaGGttagagatatgtaaacaaaatatGGGGgaaaaaaGGgaaGGagttgatcatttgaatgtgtttttt
tttcttttttttgcttttttttGGtcaagtgtgttgtaattaagtttctatcgtttaatttgtgatttgtttcaca
atgttgctaaGGttgtaatttGGaaagttgtaagaGGGGaaatgttgtatattattacaagtgaatgtgttttatt
atatgatatatatatatataagag SEQ ID NO: 50 (guide sequence 1) 5'-TCTAGTGGAGAACTCCGAT-3'

SEQ ID NO: 51 (guide sequence 2) 5'-AAAAGTTCTTGTACATCTTC-3'

SEQ ID NO: 52 (Cas9_F11 primer sequence) 5'-CCAGATTCATCTCGGGGAGC-3'

SEQ ID NO: 53 (Cas9_R11 primer sequence) 5'-GAGCTGCTTAACCGTGACCT-3'

SEQ ID NO: 54 (Cas9_F12 primer sequence) 5'-GGACTTCCTGGACAACGAGG-3'

SEQ ID NO: 55 (Cas9_R12 primer sequence) 5'-CGTGAGTTCTTCTGGCCCTT-3'

SEQ ID NO: 56 (Hyg_F2 primer sequence) 5'-GAGGGCGTGGATATGTCCTG-3'

TABLE 10-continued

CRISPR modification of tomato plants-sequences

SEQ ID NO: 57 (Hyg_R2 primer sequence) 5'-GGCGACCTCGTATTGGGAAT-3'

SEQ ID NO: 58 (Hyg_F11 primer sequence) 5'-GCTCTCGATGAGCTGATGCT-3'

SEQ ID NO: 59 (Hyg_R11 primer sequence) 5'-ATTTGTGTACGCCCGACAGT-3'

SEQ ID NO: 60 (Hyg_F12 primer sequence) 5'-TAAATAGCTGCGCCGATGGT-3'

SEQ ID NO: 61 (Hyg_R12 primer sequence) 5'-GGCGACCTCGTATTGGGAAT-3'

SEQ ID NO: 62 (T7 Endonuclease I assay oligo) 5'-TTCCCCTCTTACAACTTTCCAA-3'

SEQ ID NO: 63 (T7 Endonuclease I assay oligo) 5'-CCAGAAACGGGGGAGACTAC-3'

SEQ ID NO: 64 (Solyc01g066980 gene (underlined) with flanking regions
ctataatgcttcaatCCctttagtaattagatagtatcaataagttcagtgtaattagaatacttcaataagttca
ttgaacaaattgaagataCCtGGataGGatttcattatcacattacaaattgctGGtCCttgaagcataatattta
atctagagaagatgaCCtcttgtttgttgaatgtgctaCCattgaaatttgattgtttGGtttaaatgtgctactt
ttgaaatctgagtagtctagtgaagcaaGGtttaagttgtGGctgCCtgtttatgttgttaagttactttacattt
tCCttgtttgttcagaaataatcgatgctgctagctttCCcattatgcttaaaaatatgtttattttctatttta
ctaCCtactcaattgttcagatctttctaatttcactctgaGGctttaagtttgtgttttaattttgttagtttgat
gatctgaaaagtctttctctattaaatatatttctctgttaattgttatatgacttgcattgttttttcaCCctat
tttaagtatgaactcatatctttctttttgaCCtaaagttatgtaacataatagtctatttcatgtgtataata
tgttttaaatgaatCCaaGGtcaGGgtatCCtgctacatatattgtgtcgatgacacttttttgtctttgaatCCagaa
aaaatgagtataacGGaagttctGGatgttgagattaactcatgagttgtgttgataacaatatattagttttta
attcaactcatatagttaacaattgataaaatttgtaaatcagtaatataagtattcttctgcaagaacttataaa
tttaatgtcagatactctatattacttttgatttatgatatCCctCCtaacaaCCtcttcaaatttatacaGGctaa
aaCCttctaaaatataacgtgatttctttgtatagactattgaaaaagtttgagattcaacatcaagtgatttat
atcgacatgttcatatgaaaaatcatttgttGGtgaacgttctcgaaatgtCCatgtaagtctaaaagttGGaGGt
gttttGGttctgtcatactgtagagtgtatctgtgactgttgtttGGtataactctaataattttttgagactttt
cgatgcaatttttagtgtcgtttagatgcgattctagtgtcgttttttgtgtgactctagtgcaattgtttttGGtgc
aattataatttttgttttagagagagaaactaatgctactgtttttgtgtaattcgattgttcttttaagacttatCCt
gtgcaatttttagtgttgtttagtgtgattctagtattgttttactttgaCCctagtgtagttaattttGGtgcaa
ctctagtCCtgttttagtgaaaatttgttgttgttgtttcagtgtactttaGGtgttgtttgaGGctcttcactcg
agcatgaacttcttcttattgctacatcgaCCacattcactCCattgCCtgtcatgcttacttgcaactagtacat
caaataacaagaagagattaatgagCCagaactctgaagataagtaatataattttgcatttgtaataCCtcaaaat
catgaataGGcaCCaataatgacatagcattcttgttatttgagttttgatagattacttacagtttttttcatat
agaagaaatgaatgatcGGtaaattttagtctttgtagttttctGGatgtgcattgtattgcagtattcatagaat
tgatttatactatctgcttgattagacagttattagtatacaCCctctGGttataaCCaactgaagaagtttgata
gtactCCtgtcaatatgcataagttagtattgtGGcatatatataaactacttagttGGtatggagtagaagaatg
acataaacttaataagttGGtaatcacacgtttCCtatatCCtCCaagagaatagacagattgtagctactaatt
ttGGGGacaagtttctgatctagaaaaatatcGGttatctttcagattattcgaaaagaGGCCgagaatatctcat
tatgcgtaaagtactgtagtctagcagttgctatactttgtgtcaGGcttttgttgcgattcttatgtcattttag
tgtgaatctagtgcagttgttttcatgtaattctgatgttGGttGGctaattttttgagtgttttctGGtgttgtttg
ataacagaaatcagtttgtttttgaGGttcatctattctagaaatgtgcgagttcaagtatgatctttattctgcaa
tacaaaGGagttcaaaattatatgtctaagttaattactacaacttataaatgacatttcatGGaCCaactaatat
aagttgcactgtcaCCatttcattgaattttCCttgcaacaattatcaactaatactatgcgctagagtattatat
gcacatGGaaatcagatagCCtatttttgctatagcaacacagttctttCCttGGaagataatagagatgtcttta
agcttaaaagctgtgtgtttttatgcattttCCttaaaaaattatttttgttCCctatctttttaatgcttttctcat
tttctctagttattataGGaaaaatatgaagaaatatacGGaaaaacagtgtatcaatctgatattgatattgat
caatgtgaagcatattatcaagttgcGGGGagagaaaagaaaagaagaatatacGGtcttGGatttgaagcaagaa
tttattaGGGGcaaaatcttttatGGttcataatcattaCCaCCttcattttctcaatcaacatcgataacaaatat
GGatgagtttgtaaagcaaatgatgtctgcactaactagtcatcttgttCCtattattgttgagcaGGtgcaagca
tcgattactCCatCCGGcaatCCatcgattgtgacaCCcatagtgCCtgttgttactaatgtGGacgaGGttgata
CCttaatttcaagtgaagatcgtatCCCcttagtctCCcacaactttagtttttgatgatgtcatattttttgaac
gaattgcgtagcaatatttgatgaacgtaGGttcatttaatagcacttgatatattctttGGatatatttaaca
aaaaaatatgtGGttttgaagttttctattatatattatgaattGGctatgagtattatattatatgaatgttta
gtcattgttatgaaagaatgttGGgatGGatcaacaacgaattattgaaGGCCtgatatgttgtatgttgtgacGG
aaatttcatcgcaaatttatCCaaaatgatgaaatgaattattaaattagcgacaaaactatataaatataatgac
aaattactCCgtttctaacatgtgtgaacgaaaatatttcgtcactatgacgtcgctaaacttgtgacGGaactta
tttttcatcgtagaatcatgaaattagcaacaaaattatataaatatgacgactgcgacgaaaatgtttcatc
actatgacgttgctaaacttgtgacGGaactcattttttcgtcactaagagcttactaacgagcgttatagcaacag
tcaatactCCattgctaatctgtcactaatcatgattagtgacgaattttcattatatagtgaGGgattgtgtCCg
ttgctaaacgttgttttttagtagtgttagtttGGCCacttttGGtaactaaacaactatataaaatacaaaacac
acataatatcataaaacttatgcatgtgcataatttttaaatatttttagtttgaCCacttttGGtgagtaacaaact
ataaaaaacattatatatgcatcaagtgatcataaacatgatgtgtgtagacgttaatttttctctagtttGGCCact
ttGGtgactaacaaactatatacatacaaagcacaCCtaatatcataaaattttgtgcatgtgcataatgttaaaa
attttagtttgtCCattttGGagactaacaaactatagaaacataatacatGGatcaagtgaacataaatatgata
tgtctagacattaatttttttttttaatttgaCCactttaatgactaacaaatatattttcactaaatacacata
ttatttattacataatgaCCacttttaatttattacacaatctaaaataaatataattattacattaGGaaaatatc
aagattgttcagaatttctgcatcaatttatgaaaaacaaCCtacataattatatatttacaatgttttttaataaa
gtcactaaaagaaaaaatctttttgtctagtctcaaacatcatcttgagttttCCcttcacttatatttcatttcttc
gagatatttttttaaatatCCtttgttaGGtcagaaaaacatatgctataatatgcaaacatatgttaataata
agttataacattagaaaatatttgtttcatacataattgataattaatgttactCCattatttaaataaatcaaca
gatttttgatacaataagaaaattaattgtataaagaatctgtGGtaagtttcgtcaCCaatacatgcaatcaagc
aataacataGGacgaaatagatatttttttttatctctctttatatacgaaGGttatCCgttcaaataattctcactC
CgatgCCacatgcaagattaaatattttataatataatattaGGatcttgaacacaataatcttacataaaaattg
ataGGgacacataCCtgattaagaaaacattatcagacagaaaagtGGaatcgttagtcgtaatatGGtttctaCC TABLE 10-continued CRISPR modification of tomato plants-sequences

```
ctacttaCCctgactttatgttaCCacaaCCgtcagcgatgaaattattgttgaaaatatgtaataaCCctgatGG
gtGGaGGgaGGaCCaatttatagaGGttatgatttaatctGGtatgtctatgaagtaatcaatctacGGacgagat
ctactatttgtGGtattacttgaattacaagtaaacttgaatcataaataaaaaataattaataataattaaataa
taattcttacatcttcaCCttcaagcttcaaattcaatgattttGGtatgtgagattttattaatgaatattcttt
caaCCattgagtCCttaaaaaaCCtatattttcatatattaaattatatagaaatctaGGattattatgatcatca
tagatttaatGGaaaaGGgtctaaaatagtctcgaagtattGGaaatGGtacaaaattaCCctCCatctaCCtatt
GGctCCaaaatgtCCttctcatctatctattGGctCCaaaatacttcttgtcatCCaCCtttgagttcaaaattgaC
CacttatttaactattttaaaattaaactatttaaatattttttaaaatacttGGcgctcaactattagttataat
ttaatttattaatataatttataaaCCaactcactagcgactcattattaactaaaCCCCaCCgaattaataaaCC
aattataatatcaaaattgtcataaacagtactactaaaacacgacgaaattatagattCCtgaaaatgacatCCa
aaattattcgactctgaatcaaagCCCCaattaaatttaGGttgaaCCcttatttaGGaGGaGaaactttttaataGGa
atttatatcaagcttgaaatcaaaatctatgattaaagttaaagaagtagtacatCCgaattaattcatgcacttt
tttaaatatattttatataaatatttatGGtttgttttaaaaCCttaatatattattttttaaaaaaattatctat
gaagtaacatcacataattgagacgaacgaataattaagatgaacatagtcatacttttaagtttatcattaattt
ttatttagacacttgaatgtatgataatttacttCCatagatattttcgCCtcaaattttcaaaaactctcattGG
aagtagctttcttgttgttgcattagtaacgtgacGGgtttattatttcGGtgaGGtttaattagtaatGGgtGGg
tagtgaattgatttataaattatattaataatttaaattataacaaatagttgagtgcaacgtatttaaaaaagta
tttaaatagtttaaatctaaaaCCgttaaataagtGGtcaattttgaatCCaaaGGtGGatgacaaGGgtattttG
GagacaataGGtGGtGGGGaGGgtattttGGagCCaataGGGatgaagtaattttataCCattttcaatac
ttcaaGGgtattttaGGCCctttCCgtagatttaaatGGtgatttatagtttctctttgttactaaCCtaaataca
tgtttCCCCttaaatattagcataaattatgtacGGagttaGGagtattatttgagactgagcaaatataaGGatg
aaGGgtcatCCgtcaatttaGGacaaaagcatttacactatgtttGGatcattttattcattgtattgtattgta
ttgtattgttactataCCtacaatgtttgttttaattgttacttaaaatgcattgtattgtattgttaaatttcgt
tgttacgaaacaatgcaaaCCCCtattttgtGGaacaaCCaattcgatgtgttCCcgttgttacttagtttctttt
tCCaattatatcttttacataatatttttaaaatactattttactctttaCCttaattatttaaacatagtcaaaCCt
CCtattctagaataattaaGGatatttaagtaaatttataaattacaatacagtacgatacaatcaaaCCaaacaa
ttaaaatgttactaaacaacaaacaatacaatctagCCaacattgtatctaCCatacaatacagtacaatac
attatgaaataatGGgtaacaatgatCCaaacaaagtgttaataacaatctctaagttgtagaacaaCCttcaCCa
gcaatcaaatttttttaagttgtttagataaagatttgacttgatgttcattaaaatCCgtcattgagaagtttgaa
aactcaaattttgatactcaatttaCCataaacgtgaatcatttcaaatgaataatatattgaaagaattgagaga
agctcatatctaaaatttgagtagtttagaagaaGGtttgagttgatgtacattgaaatctttcaacaaagagctt
GGaagctcaaatttaaaactcaCCctaCCaaatatgagttatttcgagagaataatatattaaaatattaaaacat
caatctcaaattgatcaagtGGgctttctaagagatCCgcattcgtattcactgcattattcgtattcactgcatt
GGaataGGctgaaCCCCctacaatctcgttaaattgttttaGGgcaaagtcatagtgctcaCCctgtttgtcttt
aaatgttctaaaatttctaagaGGagttcatatctataatttaGGactactaagaGGaatttgaattGGtcGGgat
tttaaaaaaagtcaacttattgaaaaaaatgtattgcttttaatgtataacaatgtatattatata
tatatgtgtgtgtgtgtgagtgtgtgtttttatatatttactagtaatatattattattttttctagagatagca
attttgtctctatatCCatacacacaaatatttaaatttgaaaaatcaatctaaatactgaatttgcagctataaa
tatttgaagcaatagattgaaGGtttGGagttttaaatgtttaaaagttcgaaaatttgacagtttgaaGGCCcga
aattttaaaatatttgaagatgcaatcaacaattgctattttttatcatacatgaacttctaagaaatagatgagca
catCCatatatgctgatatatatgcatcatataataatcttgaaactgtcatacagattgatagatattaatcatc
aaCCaaacacaaatacacaaatatatatatatatatatatatatatatatatgtatgtatgtatgtatgtat
gtatgtatgtatgtatgtatatataatctaatagaGGcagagttaGGtGGGGgttcgtGGgttcgaacgaaa
CCattagcttttctgaagatatcatagatcattaaaaaaattaaatcgaCCgttctaacaaaattagagttCCaa
actcttaattgtGGctcttCCCCGGtCCataaacattttcagactgagacatgaatgctacaaaactatagcttta
aataaatacatagatacttGGtataacaagagtataaaacagaactacaacacatgtatacttgtatatcatatac
tttaatgttactaaaatttgaacttgtaaaaaaataaacaagtatcatatctaaaactttaaaacacatataaaaa
tcttttGGttttttCCctcttcatagacgttaaaGGagagagagCCaattttttatgctctatttttttttattaga
aataGGtagtattctaaaaatgcacaatttatgatttcagcagttttgtatatgttgaaactatcaCCagactaGG
tgattcagCCctgtgatataatattcatttcgtttcaaaataaataaattacacagatgttagttcaatattactt
ttcatttcgtttcaaaataaataaattacacagatgttagttcaatattactttctgttttttagctttttaattgt
caatacttcaatgcaatcaaaaaacttcttaaattcataagacaaaaatttcaaatgaaGGataaaatagaagaaat
actaattattCCtatagattgactaattaattaatttgactatgaaaaaGGtcttactaagCCacttattttgaaa
tgatcGGagtaactatacaagtattttGGtaaactacacaaattGGatCCattaGGcaaagtgttttctcatatcG
GacgcaagCCaaactatttaCCctaattgaatCCCCGGtCCaaactattcaCCtgactatCCtttgttctattcat
tgaactattgcttcttcattcttgataCCgtcaaaagtgaattatgtatgttatatacatgttttataactatttt
aaaatatgttatgtttgtttGGtgagaaattaacacattttattaaaatgtgcgataaattatattatCCaCCaat
aaaacttgtattacatgtgtttatgaattgttctatttaatatgtatcaataataaatcataaatgtattaaaat
aatcaaataaaaaaaattgttatttctataaatgataaatattttcttgcttatgtaaatttCCcttttaagatt
gtataGGtattacataaagtattcataCCCCaatCCaatcatttgagCCcatGGactagagaaatGGgctgaGGat
CCtatgtgatgtcaaCCtttcttcttGGatttcgatagaCCagaaagagaaatattaGGCCtaaattcaCCatataa
tatcactttcgttttgatttatgtgaaaatatttgcttagacatagaatttttttCCCCtgaaatttatGGtctata
aGGaatcatactttttttttttgaaagattgtCCattctgttGGaaGGagaatatataaattatatgtgcaagaata
aatgagtttaaattattatattagtacgtagtgtatGGatgCCcatGGaatgaacaatttgaagatctttgttat
gaagaaactatttctgttgagatGGctatacgcttcaagatatcaactaaaacaactcgttacaaaagtatatata
tCCttttcttttaattGGatcgatattttaattgtgtaaataatatattatattgtatgcaattgagaGGactaat
agaaaaatgaaaaatgattgtgagaaattgcataaagcttttgtgatttgaataattaaaacttGGattttttat
atttttttttgcttctttacaaaaagtatgatttGGttcGGtagatataatctttGGtttgagtatGGttaataga
atgtatGGtttgattCCtttgCCacttttaactGGatcatattttgattGGatataaaatatgattttacgtaaat
gagttacaaaGGtctattatttgaagaaaaaaaagaattttcaatgacatgacatgtcttttattagagaataaca
cttttgacgtgtttagtagttgcatagtatgaaaataatttctatcaaaatataagtgatcatCCaGGaaacaagt
cgaatataaatgaaaaGGatttgtagtatcaacgtttagcttttataaCCactatataattcttttaaattaGGta
aagagttattttacgtaatataattctcatctCCacttttgttatgacataatcaagagagtcattatcaatatatt
aagaatgtaacGGatatgacaattCCagcttcttattgtgttcgtgtgtaatgaatGGaatagatCCttaattCCa
taattttaCCactttattctaaagttttatatacatatatgcatagttGGCCtaattCCatcaatttttttcatgac
atattttaGGagaataaaCCtaaGGCCctagaaaaaaaataatcatagtttagCCtttaaCCtaCCttattCCctt
ttatagCCaaacatacattacttttgcaaGGgaaaatctcaaataagtttattGGaaatataCCaatttgaagaagc
tagCCCctcacttttttgtatatCCaatgagatttatattgtataaacttaaataataattgtGGagaatagattcata
```

TABLE 10-continued

CRISPR modification of tomato plants-sequences

```
tttgtaaaaGGgaCCataattgataaattaatatgaatgataCCattctttaattaagatagactaaGGatgctta
aaaatgCCactttattagagaaattCCatatgataactaaaatagcataattGGctaaaaaaaagttcaagtattG
GGGatcgtaaaattcttttttacacaattcaaaaagtaattagcttgtgaatcaagCCttctaatatttgattagag
tatgtaatcatcatctttatactcaagaaCCatttagctgacgaaaaaaaatgtaaatattCCttcatttcaagaa
aCCatgcaaaataatttattgatcatttgttattctttattttacataatctactagttgcacaaCCttttttaaaa
gacaaagttttaCCaacttttgtgtgcatgtagttttCCaaaGGgtaCCaaaaatcttttttttttttttgataaaga
tGGattGGtCCttttgattagcatgcaaaagataaacttaatacaaaattttgaaGGcacaagtgtgacatatatat
gtagtgcaagaatattgtctagtttcacattgttGGgcttaGGgttttGGcttttCCttttttatGGgagaGGgtgt
tcttcacatGGgtgttCCGGaatataatatatgtaaaagagatGGaGGagagtgacaacttatatatttgctcgtG
Gagaaaaatatgttact CCctCCgttttcaaatttgtttgtctgattttgatttgatacatagtttctaataagtaa
aaaagattttttgaactatcaaaaactaaaaatatgaagaatataCCaagttaCCttgcatcttattgtattaaata
cgttttgtgaaaaaaaattaaaattaaagagtttgcagaaaagaagaagaacgagacattctttttgacacaGGtt
gaaGGaatcagtaagacaaataaattaaaatgaaatgagcatgttattctcattaatatgCCtcatgcattattgt
taaagcaaaGGatgtcttgaaataaGGtaattGGtaGGtataacattgttttcttgaacaaagtttgtatatGGat
CCtgcattgtatgaaGGaCCataaagaaaagaagcaagagagtgacaGGcatatagattatagtGGcaCCacata
aataataGGcgcatatgtatatatatatataaaataaagaatcaaaGGatcttcaaGGtGGcaaatgagaGGtttg
taaagaaaaaaCCagctcatgcaatatGGttCCacttgaaagtttgaacttttcacgtgtgcattgCCcatataCCa
tatgtcaactagtgcttagaagaatagtaagacacttctagcttgttcttttgattCCattCCaagaaagtttat
tcaattcatgCCaatGGactgatattgacttatCCaatcaatcttttaGGatcaagtctataaGGattagagaat
ttgaaagaGGcGGaattaaaatttaaaatttatagattcattatgtaagacatgatatagacatttaaactCCaaa
tgctaGGtgaactaattaaacataatactatctaataaaatagaacactcttaGGgataataGGaatcaatGGcat
tgtgaacagCCaaacaactcactattaatatCCtagagatGGattctacacactgatctaGGgcattttttgtatat
CCttttatCCatgttttgagaatcaattcacgtgcataatctcatatatgCCtcatgcgttattattaatgCCa
aGGttgtcttgaaaGGaGGtaattGGtaGGgttagcttgttttcttgaacaaacactgtatatagatCCtgcattg
catGGaCCataaaaGGaaagaagtagagagtgacatagagtGGcaCCacataaaatagtaGGcgcatatgtatatat
caaaatAaaagaatcaaaGGatgtCCaaGGtGGaaaatgagaGGtttgaaagaaaatcaactaatacaaatGGttCC
acttgaaattttgaacttttcacatgtgtattgCCtatataCCatatgacaatagtgctttcgaGGaatagaaaga
cacttctaagttgttcttttgattCCGGtCCaagtttgttcaattcatgCCaatGGattgatactgactcatCCat
atcaatttattctaaatattagagttGGaatCCacaaatttaatgttttgttttaCCattttcaaGGaattgttgt
tgtttacttgtagcaaGGagagaGGgCCtctaatctaCCtctaacatgatgtgattattaatCCaaCCagatGGca
tctaaGGaaaaatgacaatgttCCtattactttcatcaaaatcttgatcatctatatcaacaataatatatttagt
aaaatcttactaagcGGGGgtctagagagaatagagtgtatgcaaattttaCCactatctcgtGGacgtaaagaGG
ttatttatgaaagaaCCCCaatttaagtgtatcaaactcaaataaaaagaaaaaagaaaacaacgaagaaaatataaa
aaaaagaaaatcaatattaagtgtacaagatcaatagcaataataaaatagtgtgatgattaaaacacaataaaa
catatcactgttgaaagaaaGGaaagctaaagaCCaGGaacaagttgcgcaacatGGtacaatcaacgtgtacaac
tGGtatctgttaaagagagttaaagtcacactaaaaatgagctattgtgtttagttgatgtagacaagactctatgt
cttatgttagctcaagatgactaGGatAaaattataattgcattactagttaaCCtctactcttgtaagttgtgtaa
ttgtattgtagtataactctaagtgtagcaaGGtcGGaactctaaaattcactcatatataaaatcatgtgctcga
tagttctaatcatcaatataatctttgatttctctcattttttctacgtgagattctacatagtatcagagcatata
aactcttCCacacattaaatctaatatgacaacatgacaaattgcaaCCCCCgtaCCaatacttgtCCacgc
tttCCttcaCCaCCtcatttCCtcttgttacattaagcttaagCCtacaaactatctcatatgaagaacataaatg
atgcaattgattcaGGtgatataatttaCCtatgttattcaGGagaatgaaCCaattaaagataattgttCCattg
aaaaGGctactgaaaaagttacagctattaatgttgagaaaaatgcaaagatagtaacaacattgatgattGGgaG
GagataaatgtatttctaaaaagttGGatgatcaGGcgagcatgtaCCtgattgtGGattgataaaatgtcaaaaa
agatgtgaacttgcttaaaataaaCCtattttcaagcaagaaaagataaaaaatttcatcttaaacaacaataaa
aatgttaagttaGGaagcaagaagattgatgaatacattaagaaagtaaaaGGtatatGGcatGGtcttgcaaCCa
ttcataaacatatGGatgaagatagaagagtaatcaattttttataaaGGcttatgtctcaagtacaagaCCttcaa
tactatcatgctagataaaacaCCatatCCcaactttcaatcaattttttttaatgctctcagagattttgatataaG
GgaGGatgaagaaaaagtactataacaaaactctaacacgacattctCCgaacaaaaGGtaGGgaaagagaaaatt
attctcataaaagaagaaataacaactCCagagaaaaattctttaagcttgatagacaaaagaatgttctcaaaa
taatcaaagtttcttaagtGGcaataaGGaaaagaacattacaaaatcatgCCaaatctgtGGtagaaataatcat
aCCgttcttaaatatttttacaGGtGGGGctactcttatgaatttacaaatgaactaCCataagcattaGGtgttg
CCaatatgcaGGatacatctgctactgatgacattttgtatgtGGactcaGGatCCagtagtcatttgaaaagtaa
cttaGGtattCCatctaCCtttaaacactacgttaaaCCtaataaatcattattaaaaatGGttcacaattagacat
aatatatgttgaaaataaCCtacattaGGtctaaaattataaaaGGtcttcgtagtCCctaagattactaaaaCCt
actctcagttaatatacttgaaaaagacattgcactcttaaacttaatgaaactaattttgttgtaaaaaaagac
gacaaGGgcattactagacaaagaatctaagagaagtGGactctatgttttagaagatagtaattctatgctcta
actgttatacaagtcttgaagacatcagaaaacttttttaacattctagattatgacatcttagtttgacgttataaa
cttcatgaaataagcataatatCCaaatctaaCCaacatgcatgttatatcttcacattaGGacacaatcaacata
taaatcatttCCttcacattaagCCttcaCCtcaagtaaCCCtcaagctatactttgtgctatgtatgaatagcgt
ctcataCCaCCatCCcacacgtcatagaacttctcaagaaaCCattatttacatctcacatgataGGaataaacgtt
tataCCgacatagaCCatgaaagctagatcatgaaatCCgatgtcatataaCCCCacaCCgtaaaaaGGtGGttta
cttgCCtaaGGtagactagataatatcttagctttGGtagaaaaCCgttgtaacatatatCCtatgtagCCacata
GGtataGGataGGaagatgtttattGGaaCCctagCCtaacgttGGgagagttttcatcttactatattcactcGG
tgattagCCtacattCCcgtagagtagtCCattcatatattgtactagGGgctaCCtatactGGgtctaCCg
actctaaatacattacaaaagaaaGGttcaCCaatactaGGtctgacgatttaaGGtacattaaagataactcatt
gacttCCcaagaaGGgtaCCctcaacattGGgtctaCCgatacaaGGttcatcatgtaacacatGGaaGGgttaCC
aatacttgatctaCCGGtCCaaGGtttatcattcattagttttttacactcatcataaaGGgtgCCattaacatcGG
gtctaCCagttcaagacataaCCtagaatactttaCCatttattcatgaaaGGctaCCaacattaGGtctatcga
ttcataatcattacattcattcattcaagaagaGGatgCCtaaatttatcaattcaaagtgtacaatacattgaag
aacaaCCcttcacactctatcatcatcattaatgagtgtttaagtgagaataaaCCttcaatcacaacacaattac
attttaagcattatcattgtactttcattgagatcacacatacacttcacatttcgatcatagattgatCCttcat
gcatatagaGGtacaaagaaaatatttataaaaCCtaataCCtaatagtaagtaacaCCtcaatttttta
aagtGGatcaacatctaaatcacaattcaacattaacattcaatcaataacttgCCctatcaaaaCCataatcaaa
attcaCCaacaaaatCCtagaatacttcaattaGGcataatatacatgattaaatgaactagatcaatataagt
cttaatcaattcaacacacattcttcataatctatcaattCCaaatcacaaaatacaatatagaaatttGGGGaaa
gcatGGgttctagaagaaattcaCCataaaattcatctttaattCCacaattgatttataattcattgcaataaagC
CtttgaaaaactttagaatcaaaCCgatgctattgaaaagtaGGattttgatcaactttgaagacttgaaatcact
```

TABLE 10-continued

CRISPR modification of tomato plants-sequences

```
ttaaaattgactCCttaaatGGaaaattGGacaaGGatcaagactaCCatgcatttactataagagtCCcatgaaa
atCCcttgaaaaacttgaCCttgaCCttGGaagcttgaaatcttcaCCtCCaatGGaGGtttctagagagagaact
tttGGaGGGGaagagagatttgtattttGGgatttgaaataatgaattgtaaaataGGgtttagatactttatta
ctcttaaaatactttgattaaCCtaaaatgatcgCCtaaacacttaaaaGGtcgaaataGGaatttaCCactaagC
CcttaCCttGGctgagttttacaacgaCCacgacaaCCaaaCCacGGacaatgttctGGttgatgCCCCaaCCtGG
tcaagCCtGGttcGGGGatgcagcttGGcaataagtCCcttaacttacgaatcaagaCCagagtcgtGGtttgaC
CtatGGGGtgtGGtCCCCctCCttaGGtcaCCacattttttgcaactttctcattttGGGGcagcttGGgtttaGG
ctaaGGgtCCtactcaaGGaCCCCtaGGgtgatCCttGGGGGGtcacactttgacgtctctaaCCCCtcaaCCatG
GttcGGgacaatactctacacacacaaactCCaaagcaaactcaaacacacactagttaGGctctagtttcactaa
ttcattttatGGgtcgttgtactatgtctaaacaaGGtaaGGagaatcaaGGaactgactgaattctaGGgacttg
ctgcttattcttGGgaGGtttgtttgactttttCCtcttcttttttgctCCaagttGGgtgattttttgtagaatgaGG
gttttGGgtatgtctgactaGGttattaagctttagactaagcaaaacgtcatagtttaGGtattaacaacgtaat
ttaaattcgtaatgcataGGgaaaacaCCaagacgaCCctgacttaaagttGGcgaaGGgCCatCCacgaGGgcac
tgacgaaCCgttgatGGgaCCacgaCCcgtcaagtGGgtcgtGGtttttgtCCactgttactGGctcttGGtaCCt
CCattacagtCCacttcacagatcgtgtgaaGGaCCaGGGGCCatgcatGGGGtcaGGtcgacGGaC
CaagCCatgactcttcagtGGgaCCtctaCCcgtGGaGGgcttcgtGGtCCaCCacttttttgatGGgtgtgaaCCa
cgatgagtatgacGGgcgtGGttCCtttcacGGCCcgtgaaCCCCtCCatGGttcatcaaattttttGGttttcagt
cttagctaagttttgaGGtgttacaaGGgtaatttgatGGatagtatatatagtcttttagattatttcttgttag
cttctaCCaagatttgtagtgtttcaacttttGGttaataaagagaaatttgttcagtaaaaaaataatCCaaataa
actagaaactcatgaacaaatGGtCCaaatcactCCttagtaCCtcaaaattcgtgcaaagttataaatcaCCatg
caaaactaataaaatcaCCaaaacttaaatCCaaactcattaattcaaaatgttgacttttGGtcaaacttcttaa
ataCCaaacttgtaaaactagaattCCttcaattcaaagtcttttactaatcactcaaatgattgaatcaatatt
aCCatgatgagatGGagtaaaaaaactgCCaattgatgcacattagatgaagtgtagaattagtgaaaGGtatt
aattGGtGGaagaGGattatattctgaaaaagaagttagaaGGtGGtCCatatatattCCatattgaGGagattcG
GataaattatGGtgtatagagtaaaGGttaaaagaaatGGgaGGattttgagaagtGGtcGGgttaattcaagtca
caaGGaCCacatttcacgagaagaaaataaGGatgtttcattttttatttattttttCCtttcaagtttgagaCCat
cttgctaaGGaaaagagatttgtatgtCCaaaagcactacaacaaacaacaaatatacatttctaaCCtattaatt
ataaaagCCacgaatcttgcaatagctttattttcttttcaagatcgttctctttctcatcttgttacttgtttac
atacattgtatactagatttcactttttttttttgaaaaagaaaaaagaaaaaagaaatCCtttagacatactaatt
acatGGagtgtctactaatcattaatgcagaaatgtagttatttctattatctttGGttttGGaagagagcgaaga
aaacaataaaaagagaactcagacttGGgattGGactctagtgatatatacatactCCttgctaatcagcttatta
attcatctatCCtttgttgaagtatgtgtttatctgatactatattaaagtgtatgaCCatttcatctaaaGGttt
atttagagagaacaaacttttattagttaatcatattgtcaacatctttagttaGGgattttgaactcaagacttC
CtgaatatatgactCCcctttcGGgaaCCatttatatCCgatagtGGatatCCactgtacaacgtaagagaaatt
ttaatagcttagttgattGGttagctaaactctcgCCtcgttGGtgattgttaactatatacagtgacataagtgc
ttgttacttaGGctaacactctatGGtcatgaaaagtgattaaaaaagagatttaaagagtaaattaaaGGgtaga
gaaagatagtgcacttaatatcataatctactcatgcaatgtttaattatatatatttctcgtcattcttctaat
tttaattctaacttatcgactCCaaaatataattatagtagtacttataaataataCCgaCCataaagaagaattc
acGGcagattttgttctCCttaacatgaaatattctcttGGgtgtttttttttaattaaaaaaacatagactgag
attctttaattatataatacaaaaaaaGGttcagCCaaatcatatattgatttctatctatcataCCttttattGGcacaaa
acatgaaactaaaaCCaatatgtatttcacaagaaatacgacatatatgtagtacGGatgatttactttaatata
tatatatatatatgataattgtttattCCttatataatattatatgtgtgttaaagagaaactttaagtcaatatt
atatatcatGGcaaGGacatgcaaacttGGagaaaattttgaacagaataatactcaacatagtttaaagtttGGt
aaacatctactGGatgtgatctaaattctctagcttttttttttaaaacttttcttctttattataatattattataa
attcgtagtttaGGtgtttaGGGGgtctaaagcaattttcttttGGgaattcacgtgatgatatacatatattatt
taattttttttaatacatatatataaGGtctataaaaaagttagtaaattcgtCCgaattcatgaaCCtatcttgct
ttaCCtctgatcgcgttctCCttttctGGCCtaCCCCcaCCacaaaatctGGaaactcttatctagttcacacata
gatgacataaCCaagaaaagtatattgaacactCCatgtttctgaataattaattaaCCttatgtattttaagtat
GGtaatattaatgtaatattaattacatttaaattaaaatgtcagtGGaagagaaagtatatgcacattatttatt
aacttcttgttttttGGgttttttatcttCCtatcatatatttaactttgtataCCatcatgttatctttctactatt
gtattttcaaattctcaaattCCacattttaagaaagtttgtaGGtagatgttcttcGGagacttattaatacaat
ctcgtttcaatttgtttatCCtactaatttattaaaaagaatgtatcttttcttCCtaatagctCCgcaagtaaa
cacataactaaagagtattttattCCattatcatatctttaatttaagaCCgtaaattttttaaactCCatctcat
atcaaaataGGataaacaaattaaaacagaatgCCtcgtataaaacaatattttcattattataGGgtacaaaaCC
aaaactcaaattcaaatgtgtaattagcatgcaatgtCCtttgatCCcttagCCttttttttctagagaacactga
aaataaGGagtattttttcatctaaacaaaagattCCCtatgtGGGGttaaagattttGGattgataaagtaaaaatG
GattcttctcaatCCtattattCCactacaaCCtCCttttttctCCttttGGtcatgtaattagaagtatacacaa
aattCCaagaactcaaaatgttctcaaacacgtgtcaattctctacttgcatgatcaataatcaatatatatat
atatatacacttttttactCCaataatcttatttCCtttgatGGtaaaattttataattttaattttttgctttcat
gaacaacgtCCttataaagttGGgaaattttcatcacttatatatgcaaacaaaatgtcatattcgtCCactttga
taatagtaacaaGGgtatattatattcttaaGGgtacaagaatatgttctCCtacaatctctcgtacattagt
tgtaaaataCCCCtcaaaactttttcacttgctacacaattttgatacacacattctaaacgtaaagaattttcttc
actatcaacatatttaagtGGtaataattaaCCttaaaattattttcttttattttcaatttatgcaatataatttgt
ttttcagaaattaaactttttgattttttcttgtgtattcatacacacaaattttttgagataaaattagtatatata
gaaattatgtaaaaactgctataaaattactgtaacagattatttaaaataatacaaaatataattaatcgtgat
aaaaaaatactcgtttgaatctcgaaattctaaagatgCCagaaacGGGGgagacaCCCCactatCCactttaag
aCCtctatcaaactcacacaatataattgtaagcatCCaaaaCCctctatataaaCCCCtcacaCCctcttcatC
CaaaCCatctcatcataaactacaaacacatacaaaaaacattctcattcaCCtttCCtctacaaaaaacataaca
acatcttcaacaatcatgtctGGagtttGGgtattcaagaatGGtgttgtCCgtctagtGGagaactCCgattgCC
acGGGGcgaacGGactCCgaaaagttcttgtacatcttCCtagtaatgaagtcatcacatcatatgcagtacttga
aaGGaaactgtactctcttGGatGGgagaGGtactatgatgaaCCtgaacttcttcaataCCacaaaagatcaaCC
gttcatcttatttctctaCCaaaGGatttcaacaGGttcaaatCCatgcatatgttcgatatcgtcgtcaagaatc
gcaatgaattgaGGtagagatatgtaaacaaaatatGGGGgaaaaaGGgaaGGagttgatcatttgaatgtgt
ttttttttcttttttttttgcttttttttGGtcaagtgtgttgtaattaagtttctatcgtttaatttgtgatttgtt
tcacaatgttgctaaGGttgtaattttGGaaagttgtaagaGGGaaatgtttgtatattattacaagtgaatgtgtt
ttattatatgatatatatatataagagtgcttattCCacaaaatattttttCCttttgcgcttaaaatctatgta
cacatatttatatcattaagtcaatgaatcaaaatgtaattatagatatctaatttagtattgaCCttttataaat
gttgaattactctaatactataaaaattaatactctgaaacttataaCCtcaaaaactttttcgtagcttgttttta
```

TABLE 10-continued

CRISPR modification of tomato plants-sequences agaagaaacaaaatgacgaagatatttctttcttcttattcgactttaatgacttcgaaagtgcacgcatCCcaag
aaGGctcatCCttttttcaaaaataaaaaaataaaaaaaacaagaattCCttatatctCCttttagtactacaCCtt
attatattatgacGGttattatttgtatttcaatttatgtgacacattttattttttagtgttatatagtttaaa
tttaattgagaatttGGaaagaagctcatCCCCattattttttctctCCatttCCCCgagtttCCacttGGatGGa
agCCatgtgtcgtaactaaaaattaaGGcGGgagatttgaaataacaaatattattttttcaaatctCCaCCcttaa
tttttaattatgacacatGGcttCCatCCaagtGGgaactgtagtaaaaatgtaatGGagaGGagCCtcttCCaag
aattgtgcatgaaattttcaatttttttttttaaagaatatatatatttgtaaactatataaaaaatattataagtc
acactaattgacaattcaaaatatttaaaagacatgaaaaaattacgataaaaaatagatttatttaaatttcaaa
atttaaattgtatcacataaactgagacatatattatactaattttttttgctcagaactttacttaaaacttaaaa
gacgattatgtacacaatttatcttagctcgaatagtattaaaattagataataacttta CCgaaaacaaaaacga
aaaagctaGGaaagattattgatattactttgagcaattctttcttaaatactgaataatatttcacttgatttta
atatgttagtgaaattatttgcgcttcgcgcgactatataaaatatttataagataataatatgtaatatttaGGt
tagtattaaatatataaaaaatataaatatttctCCtcgtctgcaatattataGGtttcttttaaaacatataaaa
tatattattaattttgtatatgtatattttagaataaattatttagcgtGGtgaagtaaatgaaataagagatata
tgttgaaataacaatatattatattaGGttgcaaatattttatatgtctaattttctctatcttttgtaGGataac
taattttctattcaaattttgatttcgtcaaaacaaaattaatttttttaacttttatttttacatttgcttatta
taattatttaaacattaattaaatatttataagactaacgaaaaatgaaatataaaagttaaaaatgaaacatttc
ttaCCttcatgtacttctttttttgttacaaaCCaatactgtatgatgagaagagaaatgataattgtgaatgtga
atcttcatgaaactaatatgaattataGGcaaaataaaGGaataCCataaGGcatcataaacttacaaatttaat
ttGGaagttatGGacacaaaaattatgagagttatgaatatttaaaagtaaaaattaaagaGGGGcaagtcatcat
gagtagtaactCCtagtaaataaattaaaaaataaaaataaaaatacttaaaatataaaaaaagttttattatgat
ttcatGGttagaagtgagataaacaaataaaagaataataaGGgagttttttttaataaatatttctacattaat
aaaatattttatttgtataaaaaaCCatcaGGttttttcgaatgcgaatttGGagtaaaaagcaGGacaatttaacta
catgcaatCCgatctgaaataagtcaGGcaattatactacGGCCactCCataaatttgtcatGGatcactttcCGG
GGtgcaaaaGGattcgtagatcatatatatcaCCtgtatatcatgtatatcagctgtatataaaagaaattcagat
tttaaaacacacattttgagtttcttgtaatacttttcaCCctttattgaCCCCaacaaCCcttaaaagctctctt
caatCCtCCcaagtcttagtaagtatCCCCcatgaatttacaacttaaaagtcaatattcatacgattcttttaga
taaagtctctattatttcagtatcagatttttaatattcatgagtttgtttGGaaaaatattatgtatttcaaaaa
attatttatatCCtattatatttGGaagaGGttattactatgtcttaaatattttCCctCCataaataatCCttg
attgacaattactCCtaatCCaaatataacattagtttcatCCatttattcattcttgaatgagtaactaatgaga
atactgtttcttttaaCCaaaataaatGGtcttcaaatcttttgCCcttattGGctcattattGGcattaattctt
ttttaaCCgttGGagCCtttaGGcttatatatactttcatataaagtgttcttCCtctatcacaatgtgtgaaaa
aaaatatacattttgagtttataaatctttCCttctatattttattGGtgtgttGGatttcgttttttaaaaatctt
tgtcaatttctGGctctagtagaagaCCttgctgaatCCtGGggagatatCCatatcGGgtgaaatatCCttaaGGa
tattgtctctcgacacgCCtcaagctttgagaagttcttacaaaaatttgtGGtaaagtataagatttgataaatt
cagtacaagtattcgtcaaaaagatatttaGGtaaaatttacaacttttgaataatcagtatgatcaataatcgtc
aaattattagtataaCCagtcagtcaaacatttttttttattGGgagtattCCttatcatcaagcGGgtctataGGg
atgaaGGttcaCCcatcagcttaGGattgagacatctaatagaaattCCtaaaactattagaactacgtgCCaCCg
ttGGaaatcagcttagtGGtaataCCtcattagctcaaattaGGgtttataCCCCcaataaGGtctattgagattt
ttttgatGGGGattataGGttaaaattcatatttagttcactaGGtGGtgttGGttattagtattgtctcatat
attgcttgaCCttgttaatcacactaactgtCCgtttgaCCatgcgatatagtatcatgatatGGaatcatgagat
gaaattgctgttttgtttGGacataatgtgatatgaaattttGGtgttctatattcataaatataaaactCCataa
gttctaaaactattaaataaCCCCaattatttattcaatattatcaaataaacaaaaaatcataaaatcgtatag
taaattattgtaaagttattttttctCCacttaagtaatttgtaattgtttcatcaatatatttgagtaaaaataa
aacaCCtttcacatgctcttcaagattttattactcaacaatcgtgaagtgtgagttaaagtgattatatgttGGt
tagaataataatttttttttaaaaataattatgtgatcataattttttgttacatgtgaaacaaatGGttagtagat
ataaatgtGGGGttgttttaacaaaatataaatctgtgaatcaattttttctattaaaataattcaaatcatgatat
agtattCCcacatgatacaatatcattgttttttGGagaatatgatatcactgtataCCatatcatgaga
tgaaatcagcgtaaaatcacatatCCaaatgttGGtatcacatgaCCaaacaCCtaataaatatatgtatatgaca
tttcagatatattctgagatgaatatacgtaaaaacagaGGcgagcgaaaaaGGgagagagacaaacaagataGGa
aaaagacaagcaataaaGGaagagacaCCaacaagattcgattttgaagagCCctaaCCCCtaCCtaataaactca
aaGGtaaaatgttGGcGGattgtgaactGGgctaGGcaaCCaaCCCCttgtatagaaCCcGGCCtaaaattGGtgt
cgttaGGctcaaaCCgaactagCCagctaGGGGtatcatcaaattttgaagaatcgagaaactattgtgcaaattt
ttaCCaaattaaatcattatataaaaaaatttatcaaaataatatatttttctaaaattttacaaaactagtataa
cgtttttttacagtaacgttttaGGtatattttactttttaaaagctaacagtgtcagattgatatacgttactgta
agtaacgttttactCCtaaaacattattttgagtaacgttttactCCtaaaacattactatgagtaacgtatatca
atctaacgctgtcagcttttaaaaaataagatatatCCtaaaatgtcactgtgaaataagtttataataattttat
aaaattttatgaaaaaacatcttattttgatgaattgctttatataatgacttaatttGGttaaaactaattaatg
cataCCaatctttgacaaaagtgcaattGGtcaattGGgagCCctttacatgtgctcataagagCCttatcaacac
gtgcaCCatgaaaaagcgaaGGcaactacaacttGGctaatctCCtttgctcttcgacataaaGGctttgactcta
tgactatgattcaataattaatatattGGttctgaatttaatCCatacattaagtcgagCCaaaactttaact
tgaagaatttcaataagtaaatttcactactatttaatacatgattttgactaaagctgaaaGGttatgaGGaact
cataattttcttttctagctcGGttcttgaattacaatgaattatataatttattgataaattaactttatttcttt
ctataagttaattagtaGGtgagaaGGaaagagtaatgctttCCacactaatcttgtgagtttaaaCCtcactatt
aataaaagttttctcgttttCCttaaaaagaaagcatattttgtgttattttttttcttctgtctCtaaaatttaaaat
cgtcaaactcttaattctgcatctgCCtctatagCCtattaaaatCCctttgaatcatgtaactatgCCacttGGG
GtgtGGgttgacaaaGGgatcaataaactcatagtgatcatgaaaaaagtgtgtgtaaaaagagtagtaacaatta
agttatttgatattcttgtcagtaaaGGCCattCCtcaaatgaatGGgcatatagtgtgtgacttcttctttgtac
actgaaattgtgatatGGgaatGGgaGGGGaaagtgaaagagcagaagagaGGaagattgatttttacttttcac
tcattaaatCCtattCCtatCCaatCCaatatCCacaaaaaagtatGGgacatgagagatctCCatttctatcact
tttaattatttCCttcattttatctattCCtattCCttttttgtttcatgttatatatcttctattttttagaaagt
tattatatatttagaaacattcttttaatcactttaataaaCCctttaattttgtcatgttatgatagtaactagac
tacattattttGGttCCttacgtaatgaaagaaaactatatttctagtcaattCCaacgcttCCtataagC
CtaaagtgattataattgaagCCataatgaaattattcatgctaaataatactCCtgatCCcttttaatttctct
gtcttgtcttgaaaaagaatgttttttttttttataattcttttactttttcaattcttttacatgtgatctttaga
agacaagattaaataacatttgatactttctatatattttaattataaaatcacaagattcagaagtcttgttta
tttttttaaaacttcatgtcaaactaaaactagataaacaaattGGaacagacactatCCcattgaaattttCCtat
tgaaaaatgtCCagtGGctatactcacactaatgtttaaattacacaacaaaattaaaaaaaaaaaaactcttGGtat TABLE 10-continued CRISPR modification of tomato plants-sequences tttagtgagaatttgtttctcaCCatacgtttttattgaCCtagttaaataGGaaatGGgtGGgaatatcacgtat
cataacacaaatttctcattgatttGGagtaatttttttttaaaaaaaattgttattagacattaattaaGGatt
aaaagaaacatcatcaacatgagatGGGgacaaattaatcttCCCCgaaatatcttttaatttatttaattcttCCt
ttttgtgaaGGgctgatcaagcaatGGatataagaatagaagattgttcttagcactaaaaaaaattaaagaattat
gcttGGaaCCcattaaCCaaaagaattaGGttcatcttatgagcataagatcattaattagtgattgtttaGGaga
agattctaatttcagtaGGgcaaattaGGgcatcttgtGGCCatttaaatattctCCcttctttttctttaatct
taataaacgtacgataagttagtatatttctaaatCCtataagcagCCacattCCaaaatCCtaCCtattatcaat
tttattaaataagaaaaaagattacttttttgCCaCCttatgtatttttttattacacactacatagaaaCCCCtat
aaaaaCCcactcacacttatgttcaa SEQ ID NO: 65 (wild type sequence)
tgtccgTCTAGTGGAGAACTCCGATtgccacggggcgaacggactccgAAAAGTTCTTGTACATCTTCtagtaa SEQ ID NO: 66 (Mutant 1 sequence)
tgtccgTCTAACTCCGATtgccacggggcgaacggactccgAAAAGTTCTTGTACATCTTCtagtaa SEQ ID NO: 67 (Mutant 2 sequence)
tgtccgTCTAGTGGAGAACTCCGATtgccacggggcgaacggactccgAAAATCTTGTACATCTTCtagtaa

The invention claimed is:

1. A method of genetically modifying a brachytic locus in a tomato plant, the method comprising: introducing a CRISPR system into a tomato plant cell, wherein the CRISPR system comprises an RNA-guided DNA endonuclease or a nucleic acid encoding the RNA-guided DNA endonuclease and a guide RNA or a nucleic acid encoding the guide RNA into a plant cell, wherein the RNA-guided DNA endonuclease and the guide RNA form a complex that targets the brachytic locus.

2. The method of claim 1, wherein the CRISPR system is selected from the group consisting of: a CRISPR class 1 system, a CRISPR class 2 system, a CRISPR/Cas system, a CRISPR/Cas9 system, a CRISPR/zCas9 system and a CRISPR/Cas3 system.

3. The method of claim 1, wherein the RNA-guided DNA endonuclease comprises a zCas9 protein.

4. The method of claim 1, wherein the guide RNA comprises a CRISPR RNA (crRNA) and a trans-activating CRISPR RNA (tracrRNA) as separate molecules or as a single chimeric guide RNA (sgRNA).

5. The method of claim 1, wherein introducing a CRISPR system into a tomato plant cell comprises electroporation, microprojectile bombardment, biolistic transformation, microinjection, protoplast transformation, an *Agrobacterium tumefaciens* vector transformation or an *Agrobacterium rhizogenes* vector transformation.

6. The method of claim 1, wherein guide RNA comprises a 17-20 nucleotide sequence comprising 17-20 contiguous nucleotides present in SEQ ID NO: 64 or a complement thereof, wherein the 17-20 nucleotide sequence is unique compared to the rest of the genome of the tomato plant and is immediately adjacent (5') to a protospacer-adjacent motif (PAM) site.

7. The method of claim 6, wherein the guide RNA contains comprises 17-20 contiguous present in:
   (a) nucleotides 1-22373 of SEQ ID NO: 64 or a complement thereof;
   (b) nucleotides 11742-22373 of SEQ ID NO: 64 or a complement thereof;
   (c) nucleotides 16742-22373 of SEQ ID NO: 64 or a complement thereof;
   (d) nucleotides 19742-22373 of SEQ ID NO: 64 or a complement thereof;
   (e) SEQ ID NO: 49 or a complement thereof or an ortholog thereof;
   (f) nucleotides 19742-24373 of SEQ ID NO: 64 or a complement thereof;
   (g) nucleotides 21742-24373 of SEQ ID NO: 64 or a complement thereof;
   (h) nucleotides 11742-27373 of SEQ ID NO: 64 or a complement thereof;
   (i) nucleotides 16742-27373 of SEQ ID NO: 64 or a complement thereof;
   (j) nucleotides 21742-27373 of SEQ ID NO: 64 or a complement thereof; or
   (k) nucleotides 21742-29135 of SEQ ID NO: 64 or a complement thereof.

8. The method of claim 7, wherein the guide RNA contains comprises SEQ ID NO: 50 or SEQ ID NO: 51.

9. The method of claim 6, wherein the PAM site is selected from the group consisting of: 5'-NGG-3', 5'-NNNN-GATT-3', 5'-NNAGAA-3', and 5'-NAAAAC-3'.

10. The method of claim 1, wherein the CRISPR system further comprises a second guide RNA.

11. The method of claim 10, wherein CRISPR system comprises a single RNA-guided DNA endonuclease or two different RNA-guided DNA endonucleases.

12. The method of claim 10, wherein the guide RNA comprises sequence of SEQ ID NO: 50 and the second guide RNA contains the sequence of SEQ ID NO: 51.

13. The method of claim 1, wherein genetically modifying the brachytic locus in the tomato plant comprises introducing a tomato br allele into a wild-type brachytic locus in the tomato plant cell.

14. The method of claim 13, wherein the CRISPR system creates a deletion of one or more nucleotides in the brachytic gene.

15. The method of claim 14, wherein the deletion comprises a 7 base pair deletion or 2 base pair deletion.

16. The method of claim 1, wherein the method further comprises generating one or more regenerants following introducing the CRISPR system into a tomato plant cell.

17. The method of claim 16, wherein the method further comprises genotyping one or more regenerants for the presence of the nucleic acid encoding the RNA-guided DNA endonuclease and/or a brachytic gene modification.

18. The method of claim 16, wherein the method further comprises selecting one or more $T_0$ plants containing a genomic modification at a brachytic locus.

19. The method of claim 1, wherein genetically modifying a brachytic locus in a tomato plant results in the tomato plant having shortened height and/or decreased internode length.

* * * * *

UNITED STATES PATENT AND TRADEMARK OFFICE
CERTIFICATE OF CORRECTION

PATENT NO. : 11,268,102 B2
APPLICATION NO. : 16/412901
DATED : March 8, 2022
INVENTOR(S) : Lee et al.

Page 1 of 1

It is certified that error appears in the above-identified patent and that said Letters Patent is hereby corrected as shown below:

In the Claims

Column 120:
Line 36, "(e) SEQ ID NO: 49 or a complement thereof or an ortholog thereof;"

Should read:
--(e ) SEQ ID NO.: 49 or a complement thereof;--

Signed and Sealed this
Seventh Day of June, 2022

Katherine Kelly Vidal
*Director of the United States Patent and Trademark Office*